US010501525B2

United States Patent
Jungbauer et al.

(10) Patent No.: US 10,501,525 B2
(45) Date of Patent: Dec. 10, 2019

(54) METHODS FOR PURIFICATION OF ANTIBODIES USING ALIPHATIC ALCOHOLS

(71) Applicants: Alois Jungbauer, Vienna (AT); Peter Satzer, Vienna (AT); Anne-Luise Tscheliessnig, Ledenitzen (AT)

(72) Inventors: Alois Jungbauer, Vienna (AT); Peter Satzer, Vienna (AT); Anne-Luise Tscheliessnig, Ledenitzen (AT)

(73) Assignee: Novartis AG, Basel (CH)

( * ) Notice: Subject to any disclaimer, the term of this patent is extended or adjusted under 35 U.S.C. 154(b) by 614 days.

(21) Appl. No.: 14/423,802

(22) PCT Filed: Aug. 27, 2013

(86) PCT No.: PCT/EP2013/067723
§ 371 (c)(1),
(2) Date: Feb. 25, 2015

(87) PCT Pub. No.: WO2014/033126
PCT Pub. Date: Mar. 6, 2014

(65) Prior Publication Data
US 2015/0225473 A1 Aug. 13, 2015

Related U.S. Application Data

(60) Provisional application No. 61/693,957, filed on Aug. 28, 2012.

(51) Int. Cl.
*C07K 16/06* (2006.01)
*C07K 16/00* (2006.01)
*C07K 1/30* (2006.01)

(52) U.S. Cl.
CPC .............. *C07K 16/00* (2013.01); *C07K 1/30* (2013.01); *C07K 16/065* (2013.01)

(58) Field of Classification Search
None
See application file for complete search history.

(56) References Cited

U.S. PATENT DOCUMENTS

| 3,138,542 A * | 6/1964 | Von Polnitz | C07K 14/3153 435/216 |
| 4,929,548 A * | 5/1990 | Wakayama | C07K 7/56 435/252.5 |
| 7,855,280 B2 * | 12/2010 | Coffman | C07K 1/30 530/412 |

FOREIGN PATENT DOCUMENTS

| WO | WO 2006082527 A2 * | 8/2006 | ......... C08B 37/0003 |
| WO | 2008/091740 A2 | 7/2008 | |

OTHER PUBLICATIONS

Liu et al. "Recovery and purification process development for monoclonal antibody production" mAbs 2: 5, 480-499, 2010.*
Embery "A sulphated glycopeptide in human supragingival calculus extracts" Calc Tiss Res 23, 13-17 (1977).*
Yumioka et al. "Screening of effective column rinse solvent for Protein-A chromatography" Protein Expression and Purification, 70(2), 2010, pp. 218-223.*
Brooks D A et al: "An improved method for the purification of IgG monclonal antibodies for culture supernatants", Journal of Immunological methods, Elsevier Science Publishers B.V., Amsterdam, NL, vol. 155, No. 1 Oct. 19, 1992 (Oct. 19, 1992), pp. 129-132.
Cohn E J et al: "Preparation and properties of serum and plasma proteins. IV. a system for the separation into fractions of the protein and lipoprotein components of biological tissues and fluids", Journal of the American Chemical Society, ACS Publications, US vol. 68, Mar. 1, 1946 (Mar. 1, 1946), pp. 495-475.
Phillips A P et al: "The choice of methods for immunoglobulin IgG purification: yield and purity of antibody activity", Journal of Immunological Methods, Elsevier Science Publishers B.V., Amsterdam, NL, vol. 74, No. 2, Nov. 30, 1984 (Nov. 30, 1984), pp. 385-393.
Deutsch et al: "Preparation of immunoglobin", Methods in Immunology and Immunochemistry, vol. 1, Jan. 1, 1967 (Jan. 1, 1967), pp. 315-321.

* cited by examiner

*Primary Examiner* — Daniel E Kolker
*Assistant Examiner* — James L Rogers
(74) *Attorney, Agent, or Firm* — Jason J. Derry

(57) ABSTRACT

This disclosure relates to methods for isolating antibodies from cell-free culture supernatant.

20 Claims, 80 Drawing Sheets

METHODS FOR PURIFICATION OF ANTIBODIES USING ALIPHATIC ALCOHOLS

FIELD OF THE DISCLOSURE

This disclosure relates to methods for isolating proteins using organic solvents and/or other reagents.

BACKGROUND OF THE DISCLOSURE

This disclosure relates to the purification of proteins by precipitation. Ethanol precipitation is a potential alternative technology to chromatography for the purification of monoclonal antibodies (mAbs) from cell culture supernatants. This technology, first established by Cohn and co-workers (Cohn et al. 1946) for the production of plasma-derived intravenous immunoglobulin, is based on the variation of pH, conductivity, ethanol concentration, protein concentration and temperature. These new methods provide many advantages including, for example, antibody preparations suitable for formulation into pharmaceutical products as well as significant time and cost benefits.

SUMMARY OF THE DISCLOSURE

Figure 1:
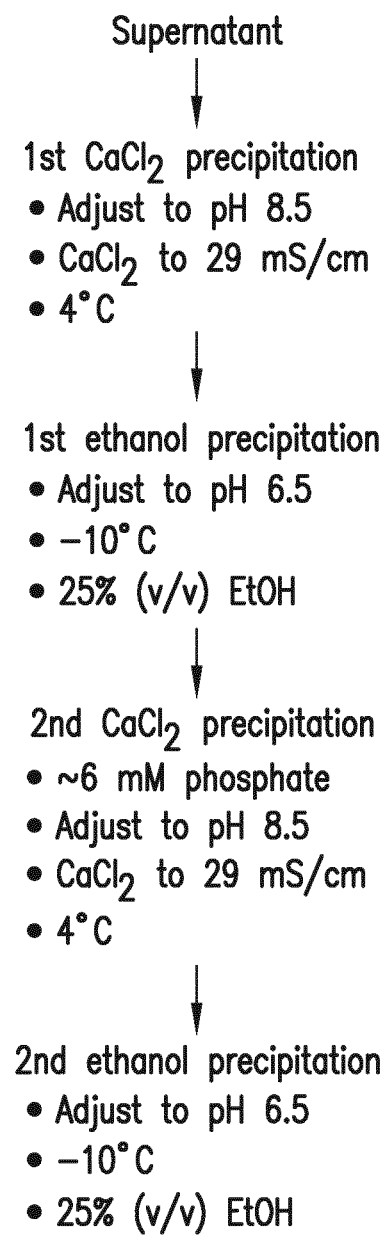
FIG. 1. First exemplary method.

This disclosure relates to methods that solve problems typically encountered during the purification of proteins such as antibodies. The methods described herein surprisingly provide for the isolation of high purity proteins (e.g., monoclonal antibodies) in high yield. In some embodiments, methods for isolating such proteins may include, for example: a) combining a cell culture supernatant with a divalent cation salt (e.g. $CaCl_2$) under conditions suitable for the precipitation of impurities in the supernatant to produce a primary supernatant; b) combining the primary supernatant with an aliphatic alcohol under conditions suitable for forming an antibody-containing precipitate and isolating the antibody-containing precipitate; c) re-suspending the antibody-containing precipitate in a buffer comprising a divalent cation salt under conditions suitable for the precipitation of impurities therefrom to produce an antibody-containing solution; and, d) combining the antibody-containing solution with an aliphatic alcohol under conditions suitable for forming a purified antibody-containing precipitate and isolating the purified antibody-containing precipitate.

In some embodiments, step a) above is not included (e.g., the first precipitation step uses an aliphatic alcohol). In some embodiments, the aliphatic alcohol may be selected from the group consisting of ethanol, methanol and isopropanol. In certain embodiments, one or both of steps a) and c) may be performed in less time than one or both of steps b) and d). In some embodiments, step a) may be performed in about ten minutes or less and the conditions thereof may include a phosphate concentration of less than or equal to about 6 mM (e.g., about 0.1 to about 5.9 mM). In some embodiments, the aliphatic alcohol of steps b) and d) may be combined with the supernatant or solution, respectively, over a time period of about 30-60 minutes or at a feeding rate of about 10-30 μl/min.

The aliphatic alcohol of steps b) and d) may be introduced from a stock solution comprising less than about 50% (v/v) (e.g., 35% v/v) of the aliphatic alcohol (e.g., the slow addition of highly dilute ethanol). A suitable pH (e.g., about 6.5 to about 8.5) should also be used in each of the steps, which may be the same or different between the various steps. In some embodiments, the conditions of step a) and c) comprise a pH of about 8.5. In some embodiments, the conditions of step b) and d) comprise a pH of about 6.5. The conditions of steps a) and c) may also comprise the presence of a divalent cation salt (e.g., CaCl$_2$). The conditions of these steps may also comprise an appropriate conductivity (e.g., about 8-80 mS/cm). The conditions also typically comprise a suitable temperature (e.g., a temperature of from about −10° C. to about 4° C.). Thus, the conditions of steps b) and d) may be selected from the group consisting of a pH of about 6.5, a final concentration (v/v) of aliphatic alcohol of about 25%, and a temperature of about −10° C.

In some embodiments, a protein (e.g., an antibody) may be isolated from a cell culture supernatant using a method of combining a cell culture supernatant with CaCl$_2$ at about pH 8.5 and removing any resulting precipitate to produce a primary supernatant; combining the primary supernatant with ethanol from a stock solution of less than about 50% over a time period of about 60 minutes (and/or a feeding rate of about 30 μl/min or less) at about pH 6.5 and isolating the antibody-containing precipitate; re-suspending the antibody-containing precipitate in a buffer comprising CaCl$_2$ at about pH 8.5 and removing any resulting precipitate to produce an antibody-containing solution; and, combining the antibody-containing solution with ethanol from a stock solution of less than about 50% over a time period of about 60 minutes (and/or a feeding rate of about 30 μl/min or less) at about pH 6.5 and isolating the purified antibody-containing precipitate. The antibody-containing precipitate is typically isolated after the last step (e.g., step d) and may be washed (e.g., with aliphatic alcohol). Certain exemplary methods are illustrated in, for example, FIGS. 1, 10 and 17. Methods for using the proteins and compositions comprising the same are also provided and described below.

DETAILED DESCRIPTION

As described briefly above and in more detail below, this disclosure relates to methods that solve problems typically encountered during the purification of proteins. The comparison of the purification strategies for the monoclonal antibody-containing supernatants A, B and C surprisingly showed that the purification strategies presented here may be used to selectively separate IgG from protein impurities and DNA directly from cell culture supernatant with exceptional purity and yield.

The methods described herein are generally suitable for use in purifying recombinant protein from a cell-free culture supernatant. It is also preferred that the yield of protein, including antibody, isolated from the cell-free culture supernatant is high, being about any of greater than about 30% to about 100% (e.g., about any of 30%, 35%, 40%, 45%, 50%, 55%, 60%, 65%, 70%, 75%, 77%, 80%, 85%, 90%, 90.5%, 95%, 95.8%, 98.2%, or 99%; e.g., "high yield"). Surprisingly, the methods described and illustrated herein provide such high yield directly from cell-free culture supernatant without requiring an initial purification of the monoclonal antibodies therein and/or the use of additives such as polyethylene glycol. Thus, in some embodiments, the methods described herein provide monoclonal antibodies in high yield directly from cell-free culture supernatant (e.g., without chromatographic purification) using a precipitation solution that does not include polyethylene glycol. The antibodies typically provide acceptable long-term storage characteristics (e.g., low aggregation and fragments).

In some embodiments, the cell culture supernatant may be clarified by, for example, centrifugation and/or filtration. In some embodiments, it may be necessary to adjust the phosphate concentration of the cell culture supernatant to less than about 6 mM (e.g., from about 0.1 to about 5.9 mM, such as about <5 mM, or about 1 to 5 mM). The supernatant may also be diluted (e.g., 1:4, 1:5, or 1:10) using a solution such as, for example, water. The protein concentration of the supernatant (e.g., clarified and/or diluted, or not clarified and/or diluted) may be adjusted to an appropriate level (e.g, to an appropriate "mass balance").

In some embodiments, an initial step involves combining a cell culture supernatant (e.g., clarified and/or diluted, or not clarified and/or diluted) comprising the protein (e.g., antibody) with a divalent cation salt under conditions suitable for the precipitation of impurities in the supernatant to produce a primary supernatant comprising the protein (e.g., antibody). Other embodiments, however, may not include this initial precipitation using a divalent cation salt (e.g., the first step is an alphatic alcohol precipitation). A primary supernatant may thereby be "derived from" or result from treatment of a cell and/or cell-free culture supernatant in any of these manners (e.g., treatment with or without a divalent cation salt). In some embodiments, however, and regardless of whether the primary supernatant is produced using a divalent cation, a divalent cation precipitation step is typically included between the first and second aliphatic alcohol precipitation steps. Suitable divalent cations may include, for example, Ca$^{++}$, Mg$^{++}$, Ba$^{++}$, and Sr$^{++}$. A sufficient amount (e.g., about 25-500 mM, about 50-400 mM, about 150-250 mM, or about any of 25, 30, 35, 40, 45, 50, 55, 60, 65, 70, 75, 80, 85, 90, 95, 100, 125, 150, 175, 200, 225, 250, 275, 300, 325, 350, 400, 425, 450, 475, or 500 mM (more particularly about 150 mM)) of divalent cation may then added to the supernatant. A sufficient amount may also be that amount required to achieve a particular conductivity (e.g., about 10-30 mS/cm such as about any of 10, 15, 20, 25, 30 (e.g., 29), or 35 mS/cm). An aliphatic alcohol may also be included at an appropriate amount (e.g., about 1-40% v/v such as about 1%, 2%, 3%, 4%, 5%, 6%, 7%, 8%, 9%, 10%, 12.5%, 15%, 17.5%, 20%, 22.5%, 25%, 27.5%, 30%, 32.5%, 35%, 37.5%, or 40% (v/v) (more particularly 5% v/v or 30% v/v)). Other conditions suitable for precipitation may include, for example, a suitable pH (e.g., pH 7.0 to 9.0, such as 7.0, 7.25, 7.5, 7.75, 8.0, 8.25, or 8.5 (more particularly 7.5 or 8.5)) and temperature (e.g., 4° C. or −10° C.). Exemplary conditions may include, for example, the inclusion of CaCl$_2$ to a conductivity of 20 mS/cm; pH of about any of 6.5, 7.5 or 8.5; without ethanol, or including about any of 5%, 25%, or 30% ethanol (v/v); and a temperature of about 4° C. or about −10° C. After a suitable amount of time, a precipitate may form and be removed, leaving a "primary supernatant" comprising the protein (e.g., antibody).

The primary supernatant may then be combined with an aliphatic alcohol under conditions suitable for forming an antibody-containing precipitate, followed by isolation of the antibody-containing precipitate. The aliphatic alcohol may be, for example, ethanol, methanol and isopropanol. The amount of aliphatic alcohol introduced may be, for example, about any of 15%, 20%, 25%, 30%, or 35% v/v. Other conditions suitable for precipitation of the antibody may include, for example, a suitable pH (e.g., 6.5), temperature (e.g., about any of 4° C., 0° C. −5° C., −10° C., −15° C., −20° C., −25° C., −30° C., or −40° C.), and speed of addition to the reaction. For instance, the aliphatic alcohol (e.g., ethanol) may be introduced from a stock solution of less than about 50% over a time period of about 60 minutes (and/or a feeding rate of about 30 μl/min or less) at about pH 6.5, and optionally at about 4° C. or −10° C. (stock solution may or may not be pre-adjusted to the same temperature). A lower conductivity of the solution may also be preferable. After a suitable amount of time, a precipitate containing the protein (e.g., monoclonal antibody) may form and be isolated (e.g., an initial protein (e.g., antibody)-containing precipitate).

The initial antibody-containing precipitate may then be re-suspended in a buffer comprising a divalent cation salt (e.g., $CaCl_2$) under conditions suitable for the precipitation of impurities therefrom to produce an antibody-containing solution. Before introducing the divalent cation salt to the initial antibody-containing solution, it may be necessary to adjust the phosphate concentration of the solution to less than about 6 mM (e.g., from about 0.1 to about 5.9 mM, such as less than 0.5 mM or about 1 to 5 mM). Suitable divalent cations may include, for example, those comprising calcium (e.g., $CaCl_2$, $Mg^{++}$, $Ba^{++}$, $Sr^{++}$). Provided the phosphate concentration of the antibody-containing solution is appropriate (e.g., 3-5 mM), a sufficient amount (e.g., 50-400 mM $CaCl_2$) of divalent cation may then added to the supernatant. The sufficient amount of divalent cation may be determined relative to conductivity (e.g., about e.g., 29 mS/cm). Other conditions suitable for precipitation may include, for example, a suitable pH (e.g., 8.5) and temperature (e.g., 4° C.). After a suitable amount of time, a precipitate may form and be removed, leaving a secondary supernatant comprising the protein (e.g., antibody).

The secondary supernatant may then be combined with an aliphatic alcohol under conditions suitable for forming a purified antibody-containing precipitate (e.g., as described above for precipitation of antibodies from the primary supernatant) and isolating the purified antibody-containing precipitate. The aliphatic alcohol may be, for example, ethanol, methanol and isopropanol. The amount of aliphatic alcohol introduced may be, for example, 15-40% v/v (e.g., about any of 15%, 20%, 25%, 30%, or 35% (v/v)). Other conditions suitable for precipitation of the antibody may include, for example, a suitable pH (e.g., 6.5) and temperature (e.g., –10° C.). A salt such as NaCl may also be introduced at this point. After a suitable amount of time, a precipitate containing the protein (e.g., monoclonal antibody) may form and be isolated (e.g., a purified protein (e.g., antibody)-containing precipitate).

Exemplary combinations of conditions that may be suitable for isolation of proteins (e.g., monoclonal antibodies) from a cell-free culture supernatant may therefore include, for example: 1) $CaCl_2$ at 20 mS/cm, pH 8.5, 5% ethanol, 4° C., followed by $CaCl_2$ at 20 mS/cm, pH 8.5, 5% ethanol, –10° C. (see Examples, strategy A); 2) $CaCl_2$ at 20 mS/cm, pH 7.5, 5% ethanol, 4° C., followed by $CaCl_2$ at 20 mS/cm, pH 7.5, 30% ethanol, –10° C. (see Examples, strategy B); 3) $CaCl_2$ at 20 mS/cm, pH 8.5, 4° C., followed by $CaCl_2$ at 20 mS/cm, pH 6.5, 25% ethanol, –10° C. (see Examples, strategy C); 4) NaCl at 10 mS/cm, pH 6.5, 25% ethanol, –10° C. (see Examples, strategy D); 5) $CaCl_2$ at 20 mS/cm, pH 6.5, 5% ethanol, –0.5° C., followed by $CaCl_2$ at 70 mS/cm, pH 6.5, 10% ethanol, –3.4° C., followed by $CaCl_2$ at 70 mS/cm, pH 6.5, 40% ethanol, –10° C. (see Examples, strategy G); 6) $CaCl_2$ at 28 mS/cm, pH 7.5, 5% ethanol, 4° C., followed by $CaCl_2$ at 28 mS/cm, pH 7.5, 5% ethanol, –5.3° C., followed by $CaCl_2$ at 28 mS/cm, pH 7.5, 40% ethanol, –10° C. (see Examples, strategy H); 7) NaCl at 20 mS/cm, pH 7.5, 40% ethanol, –10° C. (see Examples, strategy I); 8) $CaCl_2$ at 10 mS/cm, pH 6.5, 10% ethanol, –5.3° C., followed by $CaCl_2$ at 40 mS/cm, pH 6.5, 20% ethanol, –10° C. (see Examples, strategy L); 9) $CaCl_2$ at 10 mS/cm, pH 7.5, 5% ethanol, –2.4° C., followed by $CaCl_2$ at 20 mS/cm, pH 7.5, 40% ethanol, –2.4° C. (see Examples, strategy M); 10) NaCl at 40 mS/cm, pH 6.5, 15% ethanol, –5.3° C. (see Examples, strategy N). Other conditions may also be suitable as would be understood by one of ordinary skill in the art.

Any of the steps described above may be repeated as desired to achieve a particular yield and/or purity of the protein (e.g., antibody). For example, the purified antibody-containing precipitate may be subjected to one or more additional precipitations in the presence of the divalent cation salt to remove additional impurities, and one or more additional precipitations using an aliphatic alcohol (to precipitate the protein (e.g., antibody). One of ordinary skill in the art would understand that variations to these steps may be suitable for use.

Suitable divalent cations may be, for example, $CaCl_2$, $Mg^{++}$, $Ba^{++}$, and/or $Sr^{++}$. A sufficient amount of divalent cation may be determined by reference to conductivity where, for example, a suitable conductivity is about 10-30 mS/cm (e.g., about any of 10, 15, 20, 25, 30 (e.g., 29), or 35 mS/cm).

Suitable aliphatic alcohols may include, for example, methanol, ethanol, 1-propanol, or isopropanol. Other alcohols may also be suitable as would be understood by one of ordinary skill in the art. The alcohols may be utilized at any appropriate temperature. Typically, an appropriate temperature of a stock solution of the alcohol may be about the same as the temperature of the reaction (e.g., if the precipitation reaction occurs at 4° C., the alcohol stock solution may be maintained at about 4° C.).

In some embodiments, the equipment and reagents utilized in the methods described herein may be conditioned for optimal performance. For instance, the various components (e.g., aliphatic alcohol(s), buffer(s)), syringes, filters, and/or the like may warmed or cooled to a suitable temperature prior to use. A suitable temperature may be, for example, about 4° C. to about –10° C. (e.g., 4° C. or –10° C.). Other suitable temperatures may also be used as may be determined by those of ordinary skill in the art.

The various steps in the methods described herein may also be performed while stirring or otherwise providing motion thereto. For instance, precipitation (e.g., to remove impurities or antibody-containing precipitates) may be enhanced by stirring the precipitation reactants at an appropriate speed (e.g., about 400 to 800 rpm such as about 600 rpm).

A variety of filters and the like may also be suitable. For example, a "planar filter" may be used (e.g., PVDF Durapore with a 0.22 µm cutoff (Millex GV 0.2 µm) and filtration are of 2.9 $cm^2$). A "depth filter" comprising multiple layers (e.g., four layers) comprising glass microfiber layers of different cutoffs (e.g., 1 µm, 0.7 µm, and/or 0.2 µm). An appropriate depth filter may be a Whatman GD/X 0.2 µm filter. An advantage of using a depth filter is the easier filterability of the precipitate particles (e.g., about 1-30 µm) such that larger volumes may be filtered without clogging. Higher hold-up volume of depth filters as compared to planar filters may result in sample dilution and/or less than optimal recovery, although either and/or both may be used.

Certain post-filtration steps may also effect purity and/or yield. For example, the purified antibody-containing precipitate may be washed with a particular solution, which may be advantageous. A washing step may increase purity but may also result in decreased yield. Storage at room temperature may also result in a lower yield as compared to storage at a colder temperature (e.g., 4° C., or –20° C.).

Dissolution of the purified antibody-containing precipitate may also be optimized by adjusting the flow of the dissolution solution to be in the same direction as used for filtration ("in-flow direction of dissolution") or in a different direction as used for filtration ("against-flow direction of dissolution"). For example, in-flow direction of dissolution may cause any undissolved particle to be retained in the filter while against-flow direction of dissolution may cause undissolved particles to be washed out and collected with dissolved particles. These strategies may result in decreased purity and/or higher yield, or increased purity and/or lower yield.

The methods described herein surprisingly provide for the isolation of high purity proteins (e.g., monoclonal antibodies) in high yield. Some embodiments surprisingly provide a product comprising at least about any of 50%, 55%, 60%, 65%, 70%, 75%, 80%, 85%, 90%, 95%, or 99% of the antibody present in the initial cell-free culture supernatant (e.g., a high yield). In some embodiments, high yield may mean that at least about 70%, 75%, 80%, 85%, 90%, 95%, or 99% of the antibody present in the initial cell-free culture supernatant is recovered in the product.

The methods described herein typically begin with a cell culture supernatant containing the protein to be isolated (e.g., a monoclonal antibody contained with the cell culture supernatant of a hybridoma). It should be understood that other starting materials (e.g., ascites, a semi-purified, or purified preparation containing the antibody) may also be used. These methods may also be suitable for isolation of "purified" polyclonal antibodies from sera and the like. Regarding a cell-free culture supernatant, it may be used direct from culture, concentrated, and/or diluted prior to processing. The cell-free culture supertant may be concentrated by a factor of, for example, any of about 2, 3, 4, 5, 6, 7, 8, 9, 10, 11, 12, 13, 14, 15, 16, 17, 18, 19 or 20 to provide a lesser volume and, therefore, a higher concentration of proteins (and other components) (e.g., 100 ml to 10 ml being a factor of 10, or 10:1). The cell-free culture supernatant may also be diluted by a factor of, for example, 1, 2, 3, 4, 5, 6, 7, 8, 9 or 10. The protein concentration of the cell-free supernatant may be, for example, about 1-100 g/L, such as any of about 10 g/L, 25 g/L, or 50 g/L. Concentration may be achieved using any of several widely available technique such as, for example, centrifugation, ammonium sulphate concentration, spin centrufugation and/or ultrafiltration (e.g., Amicon Ultra-15 Centrifugal Filter Unit with Ultracel-10 membrane), as would be understood by one of ordinary skill in the art. These and other suitable starting materials would be understood by one of ordinary skill in the art.

The term "antibody" or "antibodies" may refer to whole or fragmented antibodies in unpurified or partially purified form (e.g., hybridoma supernatant, ascites, polyclonal antisera) or in purified form. Antibodies may be of any suitable origin or form including, for example, murine (e.g., produced by murine hybridoma cells), or expressed as humanized antibodies, chimeric antibodies, human antibodies, and the like. Antibodies may include, for example, human IgM, IgG, IgE, IgG (IgG1, IgG2, IgG3 or IgG4) and IgA (with subclasses IgA1 and IgA2). Derivatives may also be used and/or isolated and/or purified. Derivatives may include, for example, any fragment or modified version of an antibody such as, for example, an Fab, $Fab_2$, Fab' single chain antibody, Fv, single domain antibody, mono-specific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized, CDR-grafted antibody, shark antibody, nanobody (e.g., antibody consisting of a single monomeric variable domain), camelid antibody (e.g., antibodies of members of the Camelidae family), microbody, intrabody (e.g., intracellular antibody), and/or derivative thereof. A "purified" antibody may be one that is separated from at least about 50% of the proteins with which it is initially found (e.g., as part of a hybridoma supernatant or ascites preparation). A purified antibody may be one that is separated from at least about 60%, 75%, 90%, or 95% of the proteins with which it is initially found (e.g., in a cell culture sample). Methods of preparing and utilizing various types of antibodies are well-known to those of skill in the art and would be suitable in practicing the present invention (see, for example, Harlow, et al. Antibodies: A Laboratory Manual, Cold Spring Harbor Laboratory, 1988; Harlow, et al., Using Antibodies: A Laboratory Manual, Portable Protocol No. 1, 1998; Kohler and Milstein, Nature, 256:495, 1975; Jones et al., Nature, 321:522-525, 1986; Riechmann et al., Nature, 332: 323-329, 1988; Presta, Curr. Op. Struct. Biol. 2:593-596, 1992; Verhoeyen et al., Science, 239:1534-1536, 1988; Hoogenboom et al., J. Mol. Biol., 227:381, 1991; Marks et al., J. Mol. Biol., 222:581, 1991; Cole et al., Monoclonal Antibodies and Cancer Therapy, Alan R. Liss, p. 77, 1985; Boerner et al., J. Immunol., 147(1):86-95, 1991; Marks et al., Bio/Technology 10, 779-783, 1992; Lonberg et al., Nature 368:856-859, 1994; Morrison, Nature 368:812-13, 1994; Fishwild et al., Nature Biotechnology 14, 845-51, 1996; Neuberger, Nature Biotechnology 14, 826, 1996; Lonberg and Huszar, Intern. Rev. Immunol. 13:65-93, 1995; as well as U.S. Pat. Nos. 4,816,567; 5,545,807; 5,545,806; 5,569,825; 5,625,126; 5,633,425; and 5,661,016). In certain applications, the antibodies may be contained within hybridoma supernatant (e.g., a cell-free cell culture supernatant) or ascites, for instance, and may be utilized either directly as such or following concentration or dilution using standard techniques.

In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques prior to processing using the methods described herein. The antibodies may be stored in any suitable format, including as a frozen preparation (e.g., −20° C. or −70° C.), in lyophilized form, or under normal refrigeration conditions (e.g., 4° C.). When stored in liquid form, a suitable buffer such as Tris-buffered saline (TBS) or phosphate buffered saline (PBS) may be utilized. Other types of antibodies and derivatives thereof may also be suitable as would be understood by one of ordinary skill in the art.

The monoclonal antibodies produced using the processes described herein may be formulated into compositions, some of which may be pharmaceutical compositions. Such compositions described herein may take any form suitable for use in research and/or administration to a host (e.g., a mammal such as a human being). Suitable forms include, for example, liquids, capsules, emulsions, granules, films, implants, liquid solutions, lozenges, multi-particulates, sachets, solids, tablets, troches, pellets, powders, and/or suspensions. Liquid formulations may include diluents, such as water and alcohols, for example, ethanol, benzyl alcohol, and the polyethylene alcohols, either with or without the addition of a pharmaceutically acceptable surfactant. Capsule forms may formed of gelatin (e.g., hard- or soft-shelled). Any of such compositions may include, for example, surfactants, lubricants, and inert fillers, such as lactose, sucrose, calcium phosphate, corn starch, and/or the like. Tablet forms may include, for example, excipients and/or other agents such as lactose, sucrose, mannitol, corn starch, potato starch, alginic acid, microcrystalline cellulose, acacia, gelatin, guar gum, colloidal silicon dioxide, disintegrants (e.g., croscarmellose sodium), talc, magnesium stearate, calcium stearate, zinc stearate, stearic acid, colorants, diluents, buffering agents, disintegrating agents, moistening agents, preservatives, and/or flavoring agents. Lozenge forms may also be used, typically with an inert base, such as gelatin and glycerin, or sucrose and acacia, emulsions, gels, and the like. The compositions may also prepared in lyophilized form. Other forms may also be suitable, as would be understood by one of skill in the art.

Pharmaceutical compositions may take any of the forms described above, or as may be known in the art. Pharmaceutical compositions may be prepared using one or more pharmaceutically acceptable carriers prior to use in research and/or administration to a host (e.g., an animal such as a human being). A pharmaceutically acceptable carrier is a material that is not biologically or otherwise undesirable, e.g., the material may be used in research and/or administered to a subject, without causing any undesirable biological effects or interacting in a deleterious manner with any of the other components of the pharmaceutical composition in which it is contained and/or reaction in which the same is used. The carrier would naturally be selected to minimize any degradation of the active agent and to minimize any adverse side effects in the subject, as would be well known to one of skill in the art. Suitable pharmaceutical carriers and their formulations are described in, for example, *Remington's: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those of skill in the art that certain carriers may be more preferable depending upon, for instance, the route of administration and concentration of composition being administered. Also provided are methods for treating disease by administering the composition (e.g., as a pharmaceutical composition) to a host in need of treatment. Suitable routes of administration include, for example, oral, buccal, rectal, transmucosal, topical, transdermal, intradermal, intestinal, and/or parenteral routes. Other routes of administration and/or forms of the compositions described herein may also be suitable as would be understood by those of skill in the art.

The compositions described herein may be used to treat various diseases, including but not limited to cancer and non-cancer conditions. Cancer- and/or cell growth-related conditions that may be treated include, for example, benign tumors, malignant tumors, warts, polyps, and the like. Examples of cancers that may be treated using the compositions described herein may include, but are not limited to bladder cancer, breast cancer, cervical carcinoma, colorectal cancer, esophageal cancer, lymphoma (e.g., Burkitt's, non-Hodgkin's), endometrial carcinoma, head and neck cancer, leukemia, liver cancer, lung cancer, nonpolyposis, melanoma, ovarian cancer, prostate cancer, and the like. Other cancer- and/or cell growth-associated diseases may also be treated as would be understood by one of skill in the art.

Typical diseases other than cancer that may be treated with the compositions described herein may include, for example, gastrointestinal disorders such as chronic diarrhea, diseases of the small intestine (e.g., enteritis including but not limited to duodenitis, jejunitis, ileitis), peptic/duodenal ulcer (e.g., Curling's ulcer), and malabsorption (e.g., coeliac's disease, tropical sprue, blind loop syndrome, Whipple's, short bowel syndrome, steatorrhea, Milroy disease)), diseases of the large intestine (e.g., appendicitis, colitis (e.g., pseudomembranous, ulcerative, ischemic, microscopic, collagenous, lymphocytic), functional colonic disease (IBS, intestinal pseudoobstruction/Ogilvie syndrome), megacolon/toxic megacolon, diverticulitis/diverticulosis), enterocolitis (e.g., necrotizing), inflammatory bowel disease ("IBD"), Crohn's disease, diarrhea (e.g., infectious, chronic), abdominal angina, mesenteric ischemia, angiodysplasia, proctitis (e.g., radiation proctitis), proctalgia fugax, anal fissure/anal fistula, anal abscess, arthritis, and the like. Other non-cancerous or cell-growth related diseases may also be treated as would be understood by one of skill in the art.

The monoclonal antibodies produced as described herein, and/or compositions comprising the same, may be used in research to detect proteins and/or nucleic acid function/expression in cells, tissues, and the like in vivo and/or in vitro. For example, the monoclonal antibodies may be used to stain cells to identify those expressing a particular protein. The monoclonal antibodies may also be conjugated to a detectable label and/or cytotoxic moiety. Other uses for the monoclonal antibodies produced as described herein are also contemplated as would be readily ascertainable by one of ordinary skill in the art.

Kits comprising the reagents required to isolate a protein (e.g., a monoclonal antibody) from a cell culture supernatant (e.g., a cell-free culture supernatant) are also provided. An exemplary kit may contain one or more salts, solutions and/or buffers (e.g., one or more divalent cation salts and/or one or more aliphatic alcohols). The kit may also include various types of equipment (e.g., filters or the like) that may be necessary to carry out the methods described herein. The kit may also include positive and/or negative controls that may be used to confirm the method is functioning as desired. Instructions for use may also be included. In some embodiments, the kits comprise one or more containers comprising a composition described herein, or mixtures thereof, and instructions for in vitro or in vivo use. For example, the kit may include a container comprising salts, solutions and/or buffers, and/or compositions described herein along with instructions for using the same. The compositions comprising the proteins isolated using the methods described herein may be used to introduce the same to a cell in vitro, such as by adding the composition to a cell culture in bulk or to single cells and/or a composition of the protein and instructions for administering the same to an animal (such as a human being) to prevent or treat a disease condition. Other embodiments of kits are also provided as would be understood by one of ordinary skill in the art.

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

It must be noted that, as used in the specification and the appended claims, the singular forms "a", "an", and "the" include plural referents unless the context clearly dictates otherwise. Thus, for example, reference to a fragment may include mixtures of fragments and reference to a pharmaceutical carrier or adjuvant may include mixtures of two or more such carriers or adjuvants. The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

All references cited herein are hereby incorporated in their entirety by reference into this disclosure. A better understanding of the present invention and of its many advantages will be had from the following examples, given by way of illustration.

EXAMPLES

Example 1

A. Materials and Methods

1. Screening of Precipitation Recovery at 4° C.

To measure monoclonal antibody purity and yield, the monoclonal antibody-containing supernatant was diluted 1:5 with HQ-$H_2O$ before 96% (v/v) ethanol was added to a final concentration of 33% (v/v). The solution was incubated overnight in the cold room (4° C.) under slight stirring (400 rpm). Aliquots of 10 ml were collected and filtered using either a planar filter (Millex GV, Sartorius, Bedford, USA) or a depth filter (GD/X, Whatman, Little Chalfont, UK). The planar filter uses a PVDF Durapore membrane with a cut-off of 0.22 µm while the depth filter uses four layers of different filtration material (layer 1+2: glass microfiber 10 to 1 µm; layer 3: glass microfiber prefilter 0.7 µm; layer 4: PDVDF 0.2 µm). Following a factorial design plan, the precipitates were then washed or not washed, dissolved immediately or after a delay in histidine buffer (20 mM histidine, 100 mM NaCl, pH 6.0), and the flow direction for dissolving of the precipitate was identical or opposing to the flow direction of precipitate collection. All dissolved precipitates were analyzed by analytical protein A chromatography. The purity was calculated as area of IgG peak divided by the sum of the areas of the flow-through and the IgG peak.

2. Evaluation of the Purification Strategies for Monoclonal Antibody-containing Supernatant A and B.

The respective supernatant was transferred into the reactor vessels of an Integrity 10 (Thermo Fisher Scientific, Rochford, UK) and equilibrated at 20° C. (~room temperature). For all experiments, the starting volumes were selected so that the last precipitation step started with 10 ml of adjusted cell culture supernatant. Three different methodologies were used: (1) initial precipitation of the impurities such as DNA and protein impurities; (2) selective precipitation of IgG; and, (3) precipitation out of clarified cell culture supernatant or only diluted clarified cell culture supernatant. For the initial precipitation of impurities, two or three precipitation steps may be required. The first precipitation steps (1 and/or 2) aim at the removal of the impurities by precipitation. In this case, the precipitates are discarded and the remaining precipitation supernatant is used to proceed. The precipitate was only collected using depth filters (GD/X, Whatman) after the final step. It is then washed using a tempered ethanol solution of respective concentration and dissolved in histidine buffer (20 mM histidine, 100 mM NaCl, pH 6.0). For the selective precipitation of IgG, only one precipitation step may be required. The precipitate may then be collected, washed and dissolved. For the precipitation of IgG from the clarified cell culture supernatant and diluted (1:4 with HQ-$H_2O$) cell culture supernatant no adjustment besides temperature control is required. Again the precipitates are collected, washed and dissolved as described before. Adjustments were performed as follows: (a) adjustment of pH using HCl or NaOH; (b) adjustment of the conductivity using either saturated NaCl or $CaCl_2$; (c) control and if required further adjustment of pH; (d) simultaneous adjustment of temperature and ethanol addition. The ethanol was pre-cooled at −10° C. and added at 2-4 µl/min. After addition of ethanol the suspension was incubated for at least two hours. For each precipitation step, the required adjustments were performed in this given sequence. All handling was performed at room temperature unless otherwise indicated. Syringes and filters were also stored at room temperature unless otherwise indicated. The dissolved precipitates were analysed for IgG concentration (analytical protein A chromatography), protein impurity concentration (Bradford assay, excluding IgG) and DNA concentration (Picogreen assay). Additionally the dissolved precipitates were analysed by SEC. Screening of precipitation recovery at −10° C. Aliquots of 5 ml of cell culture supernatant of monoclonal antibody A were transferred into the reactor vessels of the Integrity 10 (Thermo Fisher Scientific) and tempered to 4° C. Upon addition of 96% (v/v) ethanol to a final concentration of 40% (v/v) over 30 minutes while the temperature was linearly decreased to −10° C. The suspension was then mixed at 400 rpm or 1000 rpm and after two hours collected by filtration using a depth filter (GD/X, Whatman). The filters and syringes used were tempered at room temperature, 4° C. in the laboratory fridge or ~−20° C. in the laboratory freezer. The precipitates were washed using a tempered ethanol solution (−10° C., 40% (v/v) ethanol) and then dissolved in 10 ml histidine buffer (20 mM histidine, 100 mM NaCl, pH 6.0). All handling was performed at room temperature unless otherwise indicated. The precipitation supernatants, the washing solution and the dissolved precipitates were collected and analysed by analytical protein A chromatography. The respective purity was calculated again as area of IgG peak divided by the sum of the areas of the flow-through and the IgG peak. A detailed description of the experimental set-up is provided below. All experiments were performed in triplicates unless otherwise indicated.

3. Elution Profile of Dissolved Precipitate—Recovery and Purity

The same experimental set-up as for the screening of precipitation recovery at −10° C. was used for aliquots of 5 ml of monoclonal antibody-containing cell culture supernatant. The obtained precipitate was not washed. The dissolved precipitate was collected in aliquots of 1 ml and each aliquot analysed by analytical protein A chromatography. The respective purity was calculated again as area of IgG peak divided by the sum of the areas of the flow-through and the IgG peak.

4. Comparison of Different Alcohols for Precipitation

The alcohols used were methanol (Methanol LCMS Chromasolv, Fluka), ethanol (Ethanol 96% Emprove exp, Merck), isopropanol (Isorpopanol LiChrosolv, Merck), acetone (Aceton p.a., Merck) or 1,2-propandiol (Acros Organics). Aliquots of 10 ml of the cell culture supernatant C were transferred into the reactor vessels of an Integrity 10 (Thermo Fisher Scientific) and tempered to 4° C. During addition of the respective alcohol to a final concentration of either 10% (v/v) or 30% (v/v) over 1 h the temperature was linearly decreased to either 0° C. or −5° C. No precipitation was observed for acetone or 1,2-propandiol. The precipitates were collected by depth filtration (GD/X, Whatman) and dissolved without prior washing using 10 ml of histidine buffer (20 mM histidine, 100 mM NaCl, pH 6.0). All experiments were performed in triplicates. The concentration of IgG in the precipitation supernatant and the analysis of the composition of the dissolved precipitates were performed using SEC (Bio-SEC3, Agilent).

B. Isolation of Proteins

1. Influence of Filter Type and Conditions on Recovery and Purity after Precipitation at 4° C.

Additional parameters of precipitate collection and dissolution were also evaluated (Table 1). All experiments were performed with the clarified culture monoclonal antibody-containing supernatant (e.g., supernatant B). The "planar filter" corresponds to the Millex GV 0.22 μm. It uses a PVDF Durapore membrane with a cut-off of 0.22 nm and a filtration area of 3.9 cm². The "depth filter" corresponds to the GD/X 0.2 μm from Whatman. Its filtration material consists of 4 layers: layer 1+layer 2 consist of glass microfiber with a cut-off of 10 to 1 μm; layer 3 consists of a glass microfiber with a cut-off of 0.7 μm; layer 4 consists of a PVDF membrane with 0.2 μm cut-off. The advantage of the "depth filter" is the easier filterability of the precipitate particles (1-30 μm). Compared to a "planar filter" larger volumes of precipitation suspension can be filtrated before clogging of the membrane is observed. However, dissolution of the collected precipitate is not so trivial. The higher hold-up volume (1 ml or 250 μl with air purge) compared to the hold-up volume of the "planar filter" (100 μl) results in sample dilution and even incomplete recovery. Additionally other post-filtration steps such as washing or drying of the pellet might have an effect on purity and/or yield. Washing of the precipitate using a pure precipitant solution of correct concentration and temperature can help in increasing purity. However, washing puts additional stress on the particle and might result in non-specific wash-out, in particular if the particles are small. The impact of drying is of interest to evaluate if the precipitate could be stored in the syringe filter or if it should be dissolved and collected immediately.

The direction of the flow during dissolution of the pellet may also have an effect on the efficiency of dissolution. Therefore, the pellet was dissolved using the same flow direction as for filtration ("in-flow direction of dissolution") or a flow direction contrary to the flow for filtration ("against-flow direction of dissolution"). Undissolved particles were retained in the filter using "in-flow direction of dissolution" but washed out and collected together with the dissolved particles using against-flow direction of dissolution. This might result in a decreased purity but also a higher yield. Using the factors given in Table 1 a four-factorial design plan, similar to the design plans described previously, was set up:

TABLE 1

| Factor | Description | Levels |
|---|---|---|
| A | Filter type | "−1" or "planar filter" "+1 or "depth filter" |
| B | Flow direction for dissolution of precipitate | "−1" or "in-flow direction" +1 or "against-flow direction" |
| C | Washing of the precipitate in the filter | " "−1" or "wash" "+1" or "no wash" |
| D | Drying of the precipitate in the filter | "−1" or "drying" "+1" or "no drying" |

The clarified cell culture supernatant monoclonal was diluted 1:5 with RO-water and ethanol added to a final concentration of ~33% (v/v) and incubated the suspension o/n at 4° C. under mild stirring (400 rpm). The taken samples were then processed as given in Table 2. Precipitation yield was low (40-50%) due to the low antibody concentration in the starting material.

TABLE 2

| Run # | Term | A | B | C | D |
|---|---|---|---|---|---|
| 1 | 0 | −1 "planar filter" | −1 "in-flow" | −1 "wash" | −1 "drying" |
| 2 | A | +1 "depth filter" | −1 "in-flow" | −1 "wash" | −1 "drying" |
| 3 | B | −1 "planar filter" | +1 "against flow" | −1 "wash" | −1 "drying" |
| 4 | C | +1 "depth filter" | +1 "against flow" | −1 "wash" | −1 "drying" |
| 5 | D | −1 "planar filter" | −1 "in-flow" | +1 "no wash" | −1 "drying" |
| 6 | AB | +1 "depth filter" | −1 "in-flow" | +1 "no wash" | −1 "drying" |
| 7 | AC | −1 "planar filter" | +1 "against flow" | +1 "no wash" | −1 "drying" |
| 8 | AD | +1 "depth filter" | +1 "against flow" | +1 "no wash" | −1 "drying" |
| 9 | BC | −1 "planar filter" | −1 "in-flow" | −1 "wash" | +1 "no drying" |
| 10 | BD | +1 "depth filter" | −1 "in-flow" | −1 "wash" | +1 "no drying" |
| 11 | CD | −1 "planar filter" | +1 "against flow" | −1 "wash" | +1 "no drying" |
| 12 | ABC | +1 "depth filter" | +1 "against flow" | −1 "wash" | +1 "no drying" |
| 13 | ABD | −1 "planar filter" | −1 "in-flow" | +1 "no wash" | +1 "no drying" |
| 14 | ACD | +1 "depth filter" | −1 "in-flow" | +1 "no wash" | +1 "no drying" |
| 15 | BCD | −1 "planar filter" | +1 "against flow" | +1 "no wash" | +1 "no drying" |
| 16 | ABCD | +1 "depth filter" | +1 "against flow" | +1 "no wash" | +1 "no drying" |

The IgG concentration of all samples was analysed by analytical protein A chromatography. Purity was calculated using the relation of the area of the flowthrough peak to the area of the IgG peak as determined by analytical protein A chromatography. This served as a sufficient and fast approximation when only differences within a sample set need to be evaluated. The effect on yield, mass balance and purity were calculated to isolate the main factors and interacting factors with significant impact (Table 3). As shown therein, factor D as well as the interacting factors AB and CD had significant impact on yield and mass balance, while for purity only factor C had a significant impact.

TABLE 3

| Model term | For yield | Percent Contribution for mass balance | For purity |
| --- | --- | --- | --- |
| A (filter type) | 1.9% | 1.8% | 0.2% |
| B (flow direction) | 3.0% | 3.0% | 0.8% |
| C (washing) | 0.1% | 0.2% | 87.5% |
| D (drying) | 24.0% | 24.1% | 2.3% |
| AB | 16.5% | 16.6% | 1.5% |
| AC | 1.0% | 1.0% | 0.9% |
| AD | 0.0% | 0.0% | 0.1% |
| BC | 1.0% | 1.0% | 0.0% |
| BD | 1.4% | 1.4% | 0.1% |
| CD | 21.7% | 21.8% | 3.3% |
| ABC | 0.6% | 0.5% | 0.0% |
| ABD | 0.8% | 0.7% | 0.0% |
| ACD | 0.2% | 0.2% | 0.0% |
| BCD | 0.4% | 0.4% | 0.0% |
| ABCD | 0.8% | 0.8% | 0.0% |

Figure 2:
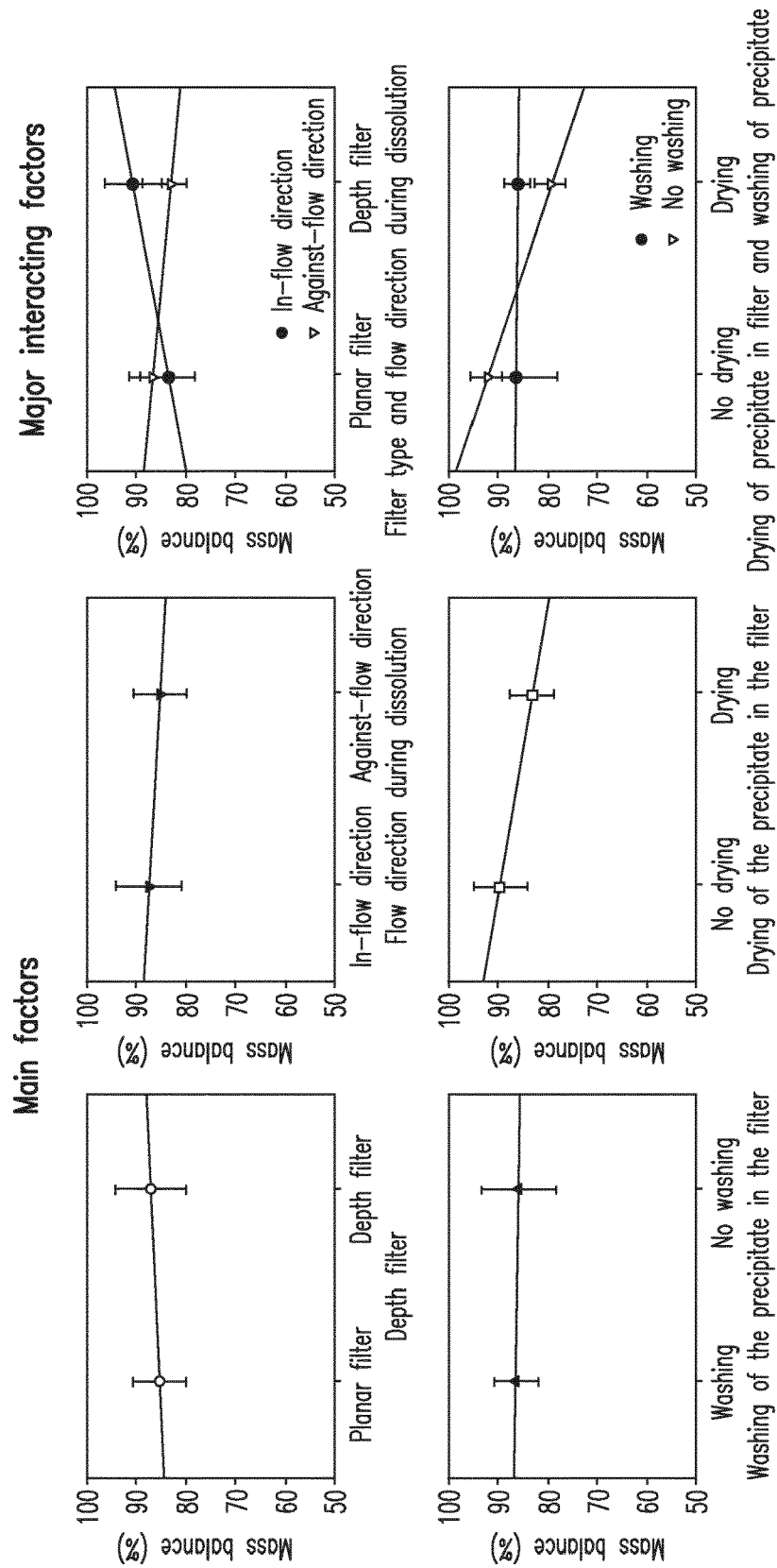
FIG. 2. Influence of main factors and major interacting factors on mass balance.
Figure 3:
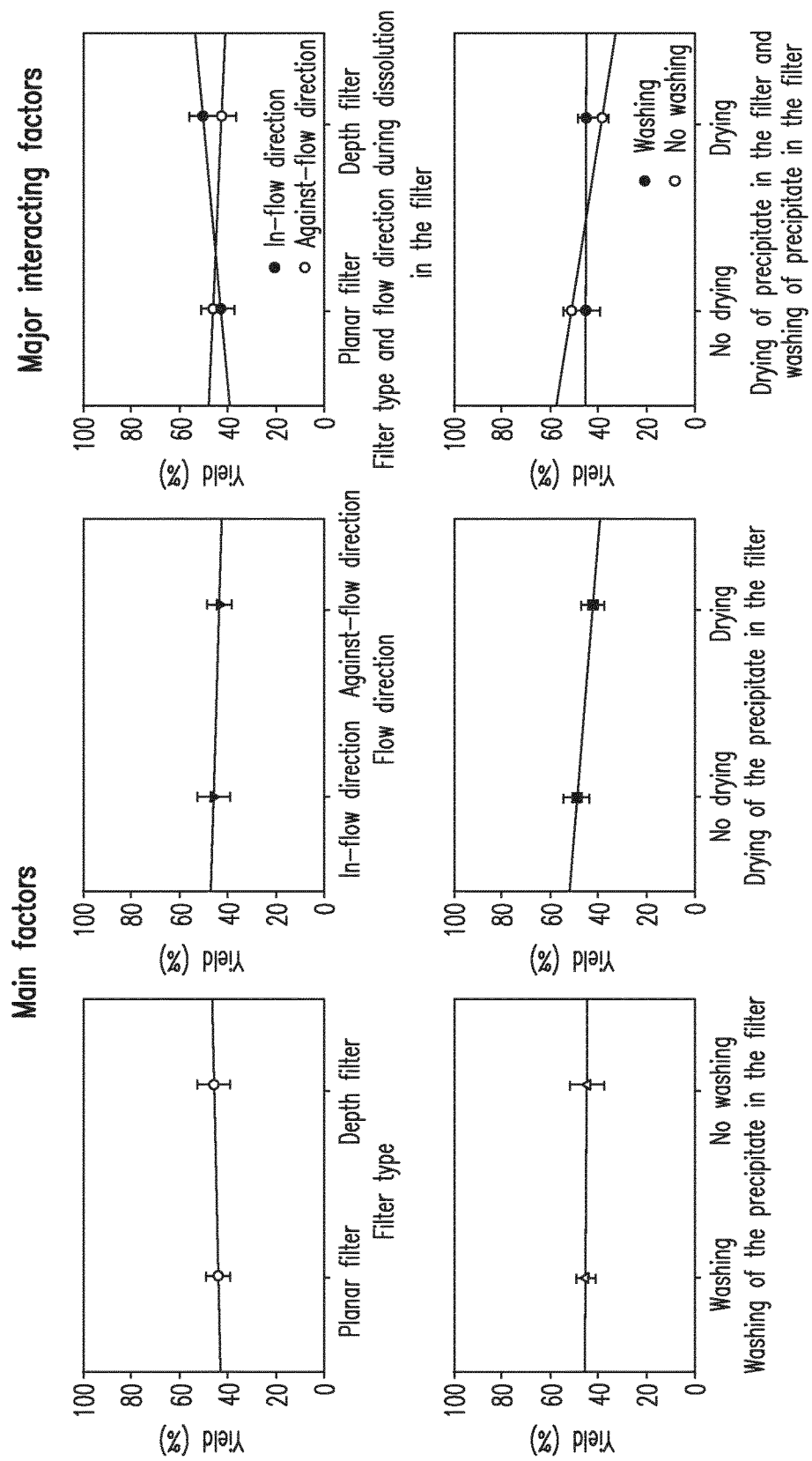
FIG. 3. Influence of main factors on IgG yield of precipitate.
Figure 4:
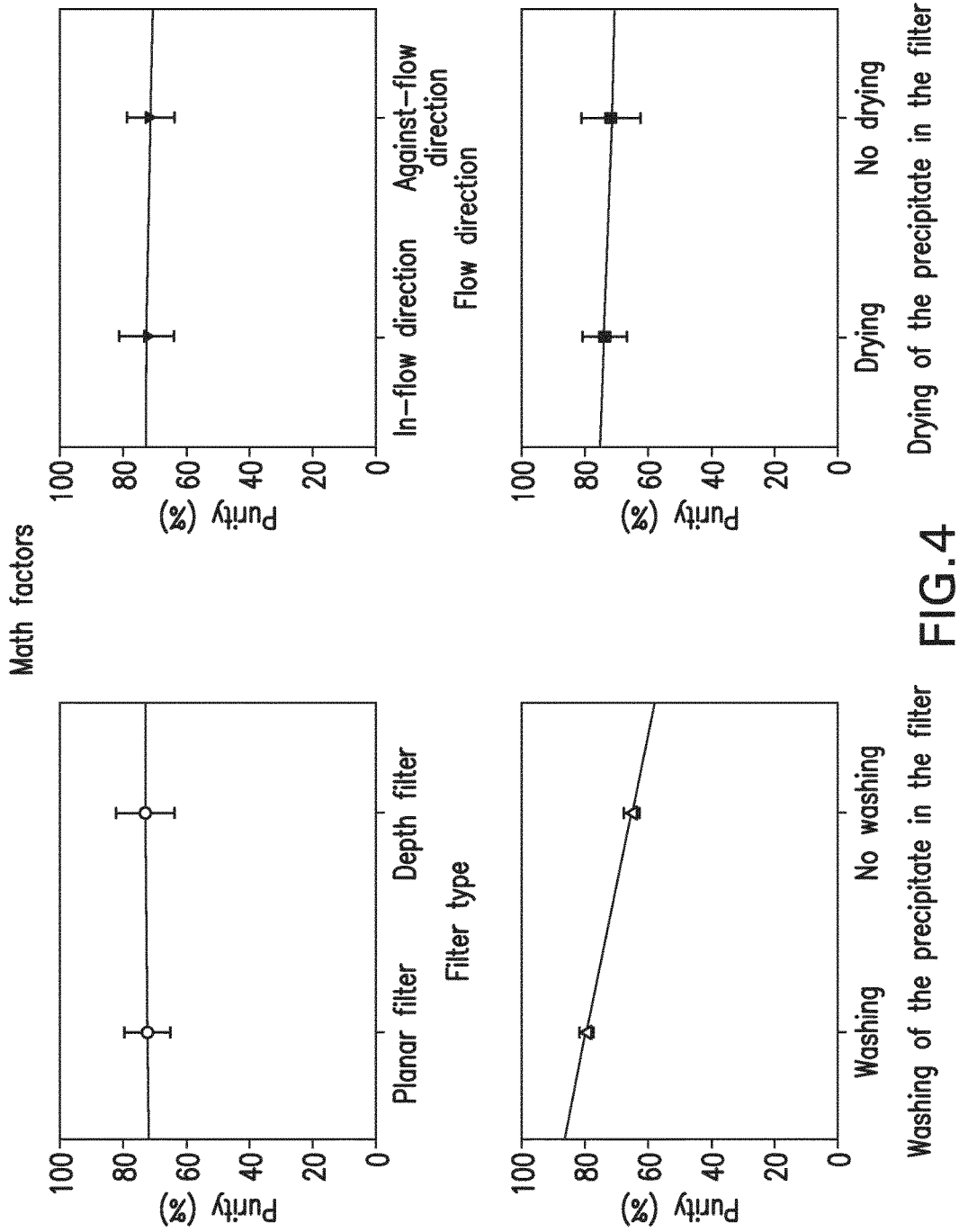
FIG. 4. Influence of main factors on purity of precipitate.
Figure 5A:
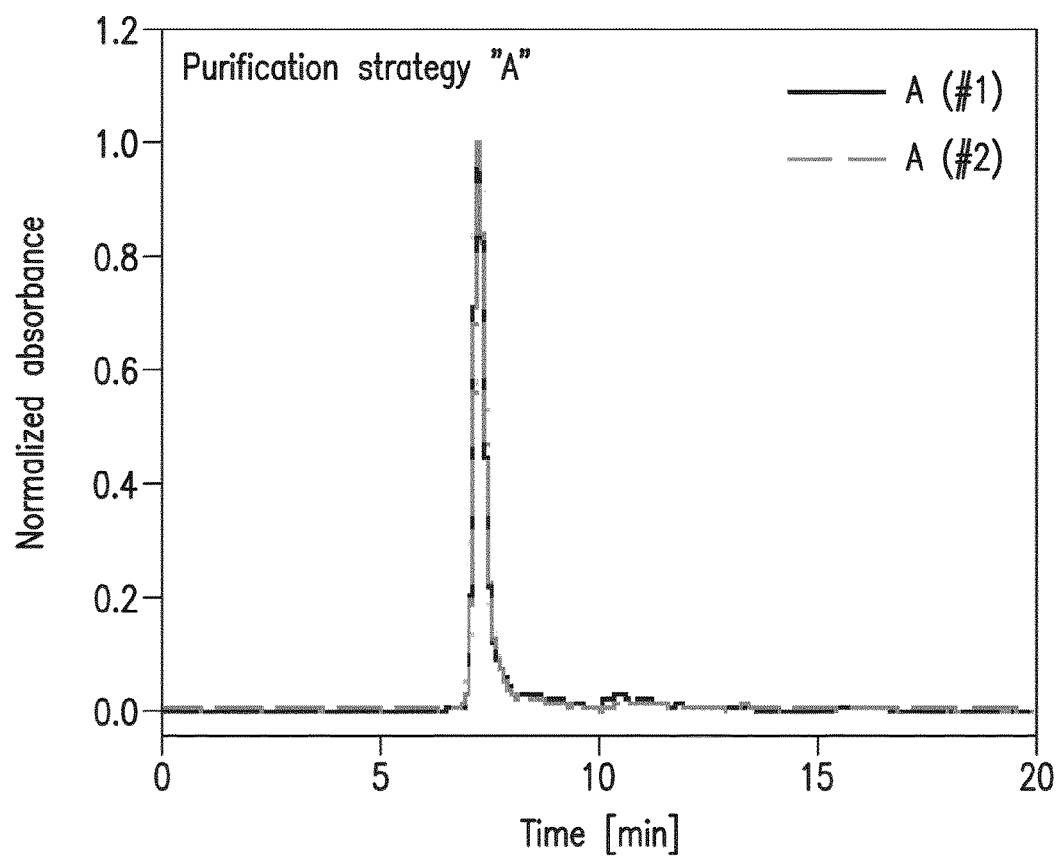
FIG. 5. SEC chromatograms for dissolved precipitates resulting from purification strategies A-F (supernatant A).
Figure 5B:
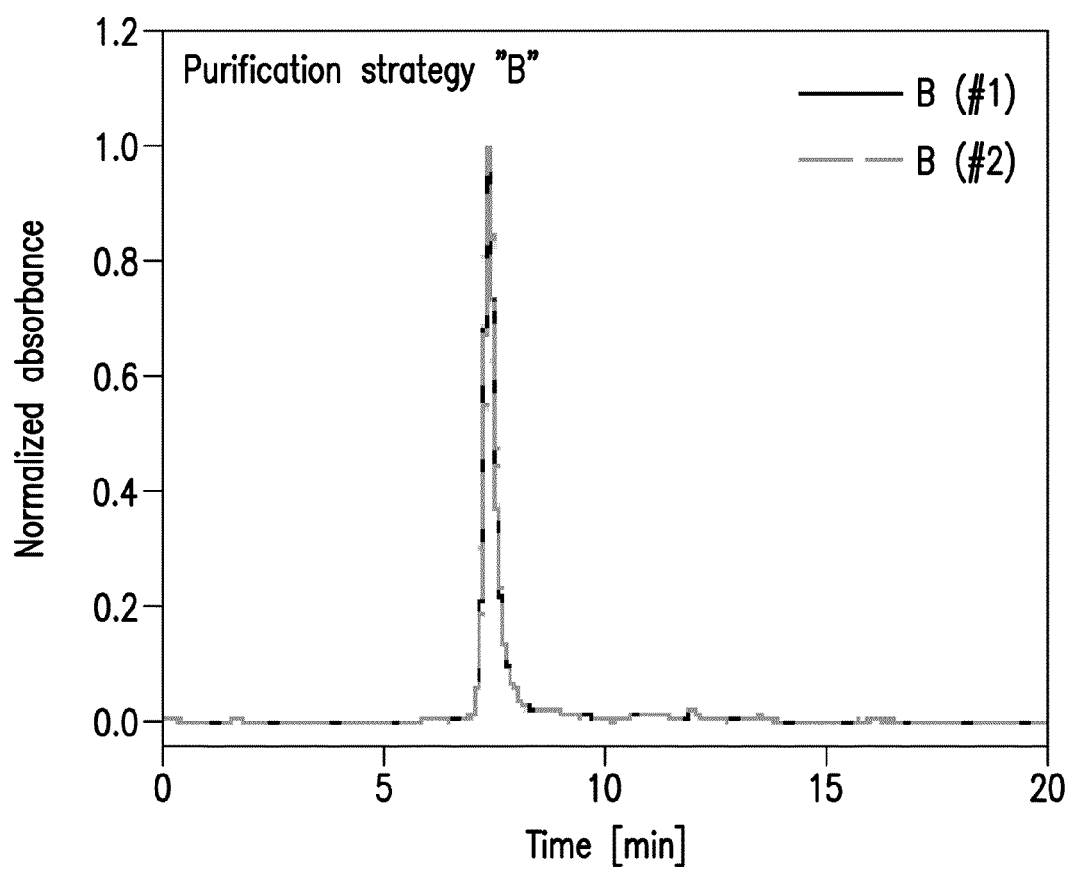
Figure 5C:
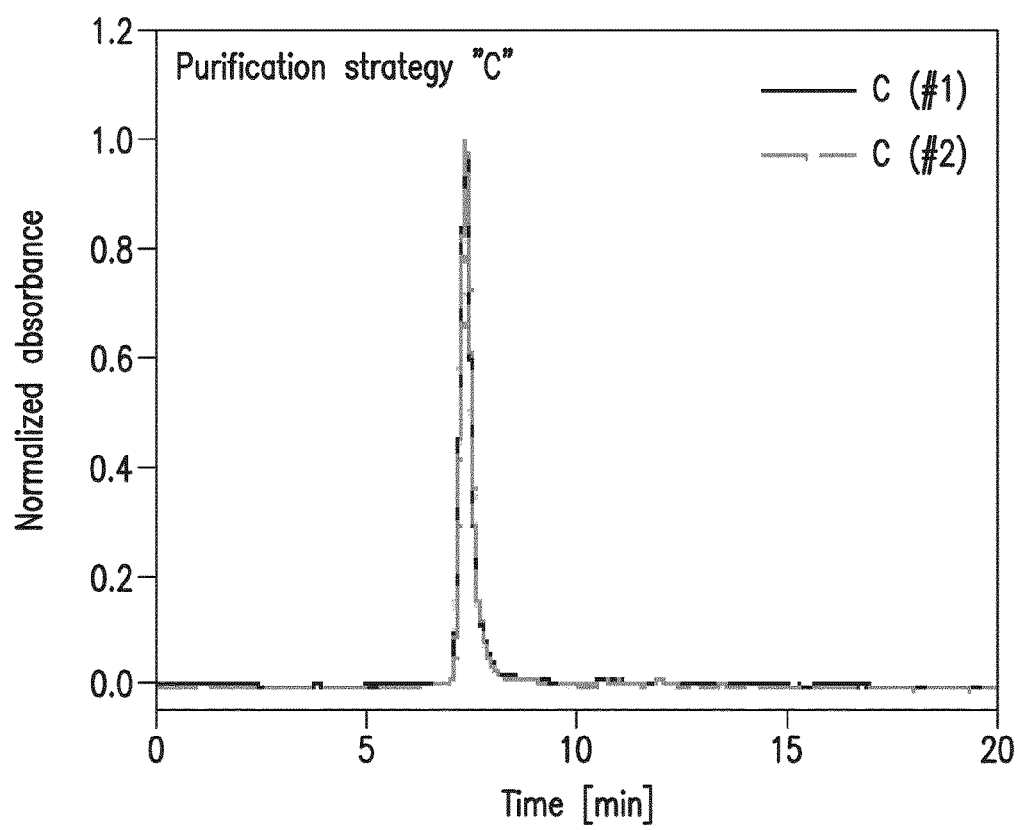
Figure 5D:
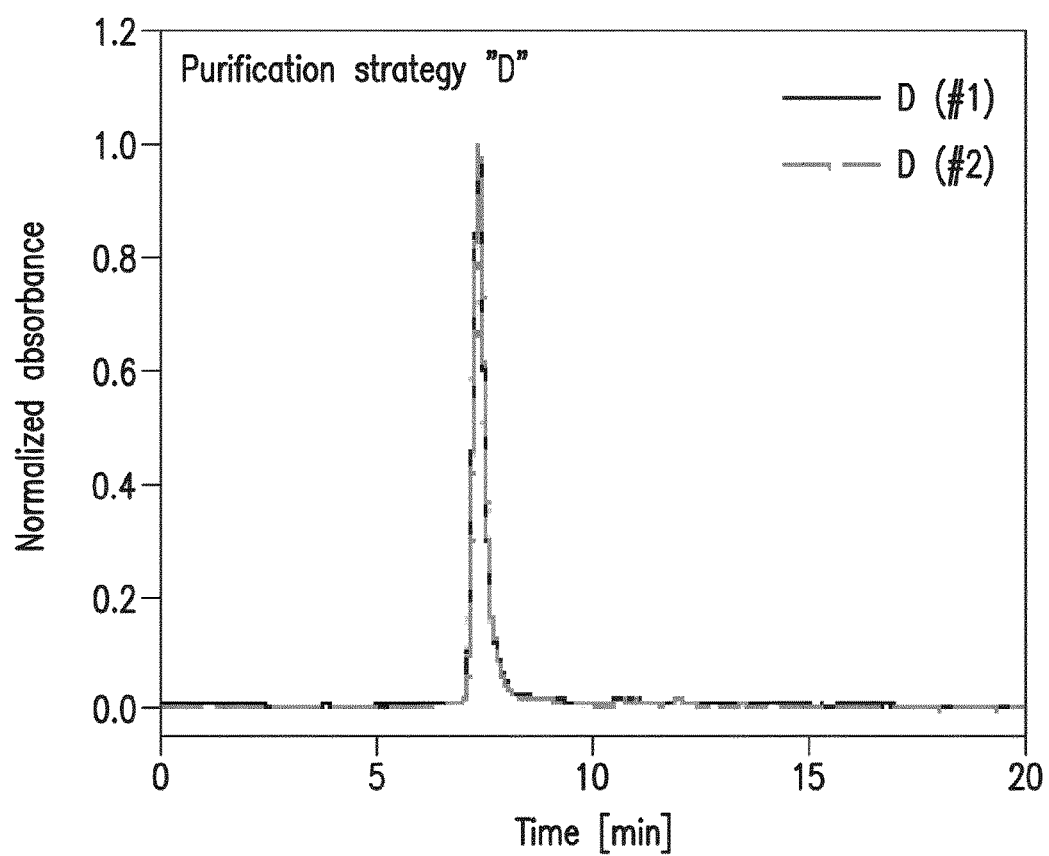
Figure 5E:
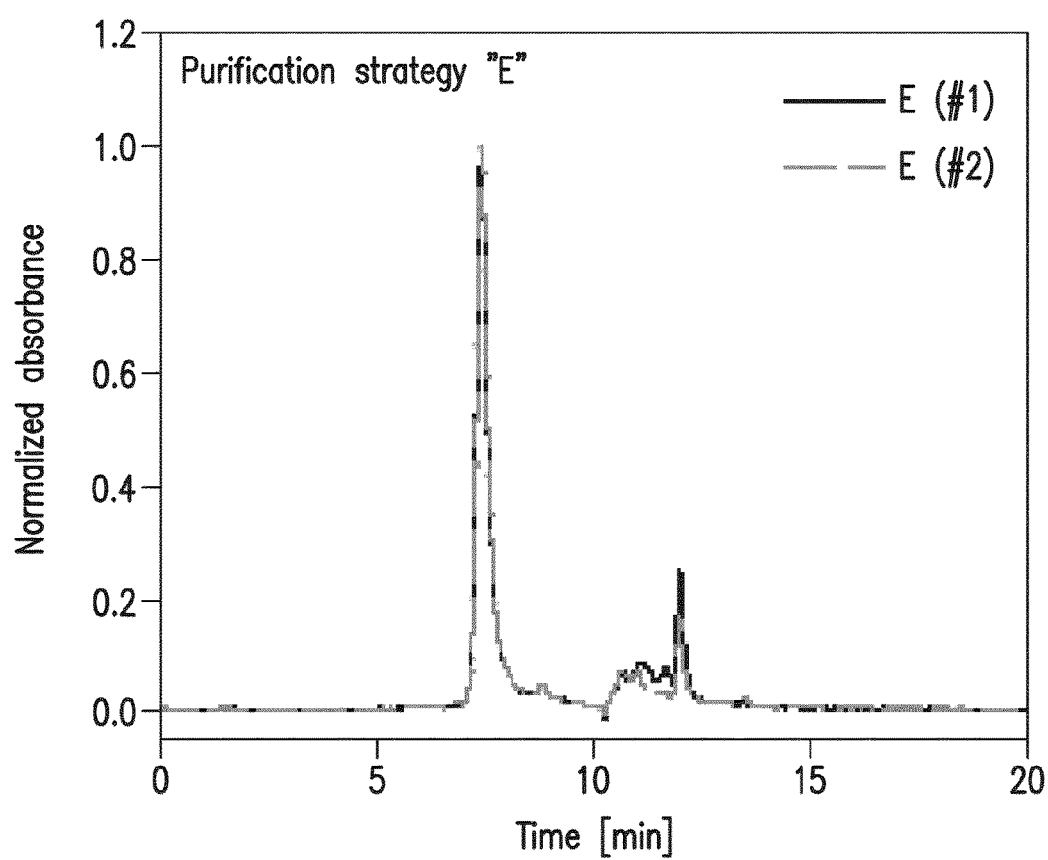
Figure 5F:
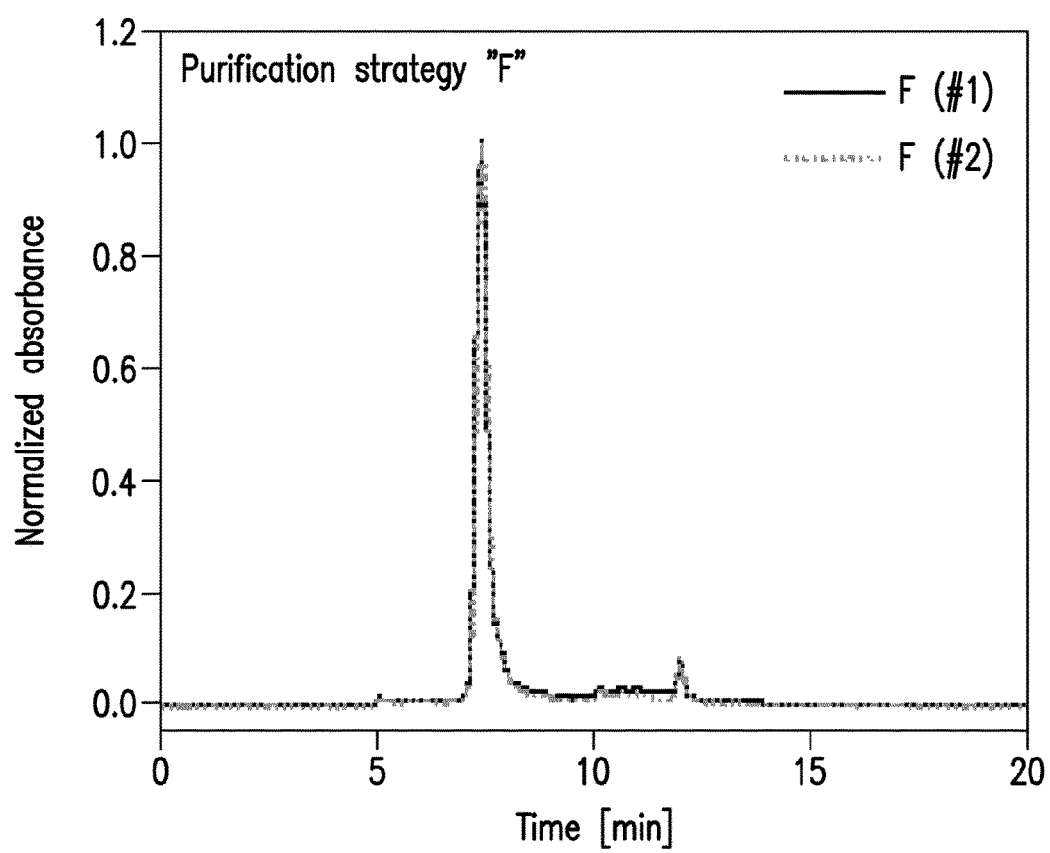
Figure 6A:
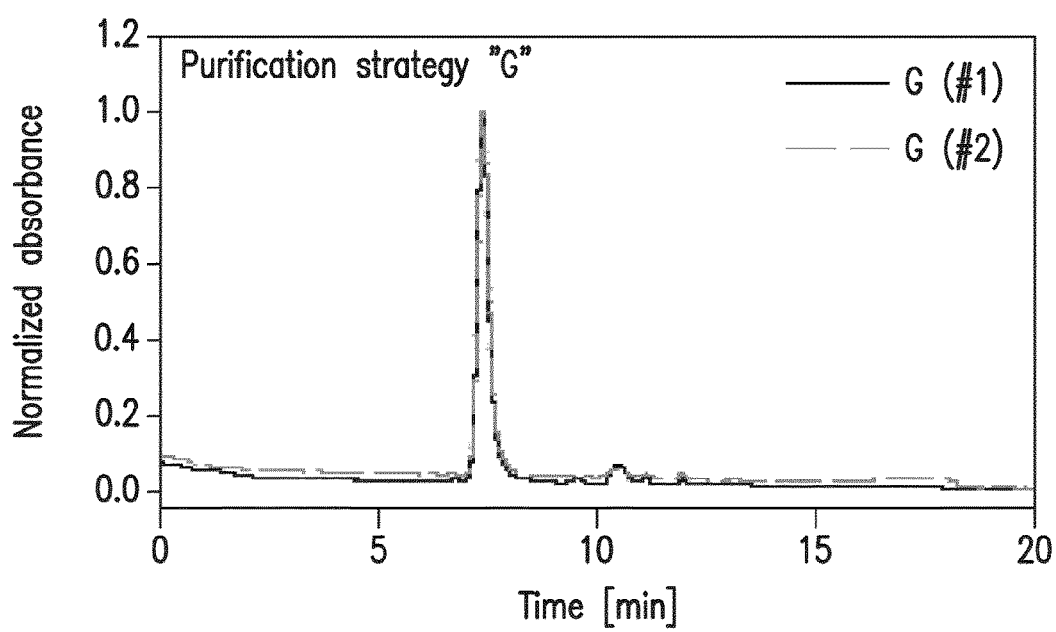
FIG. 6. SEC chromatograms for dissolved precipitates resulting from purification strategies F-K (supernatant B).
Figure 6B:
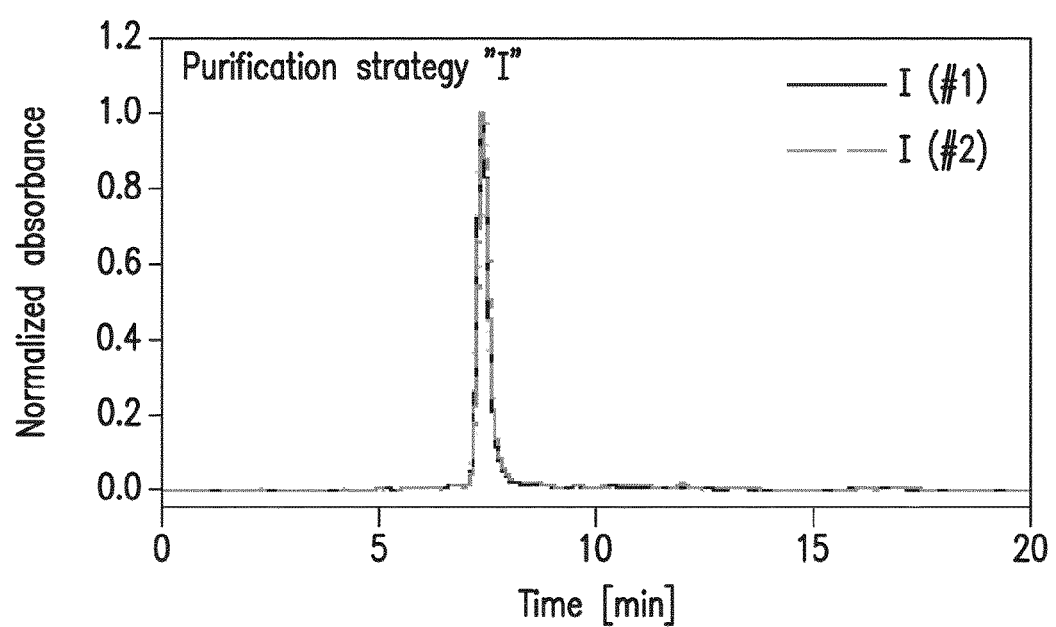
Figure 6C:
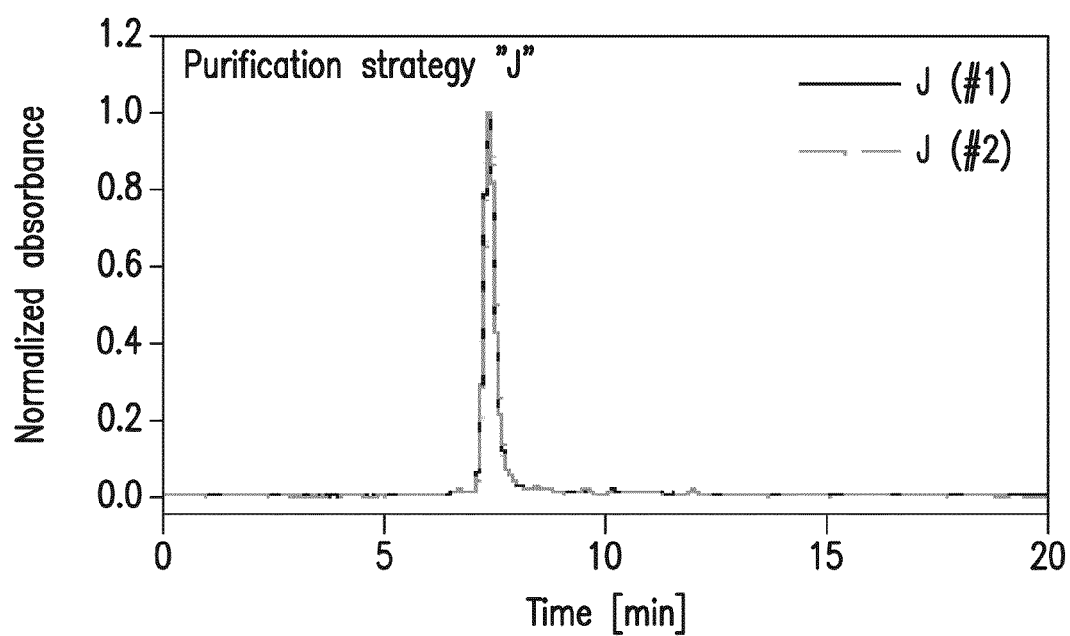
Figure 6D:
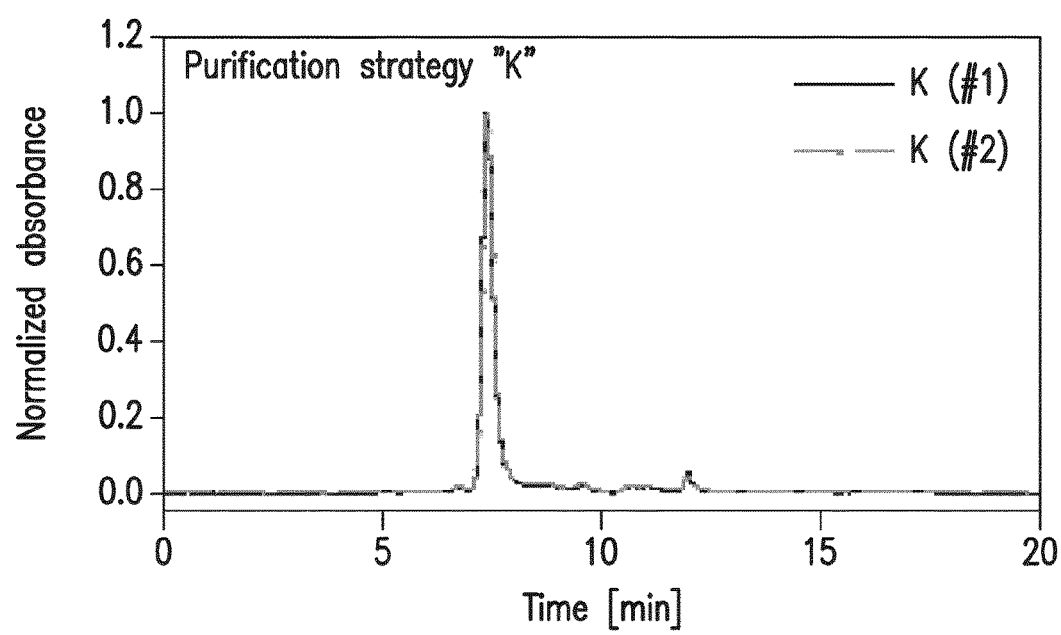
Figure 7A:
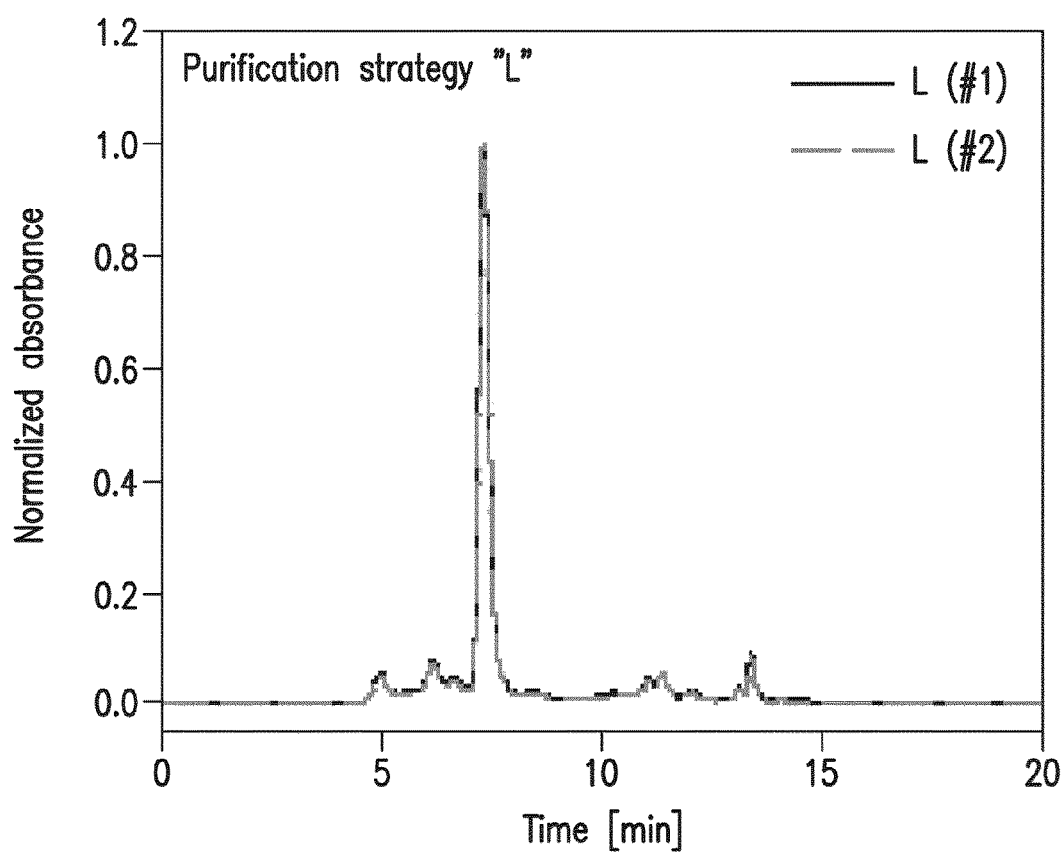
FIG. 7. SEC chromatograms for dissolved precipitates resulting from purification strategies L-P (supernatant C). All purification strategies, except M, were run in duplicate. The dissolved precipitate of strategy L is the first precipitate obtained.
Figure 7B:
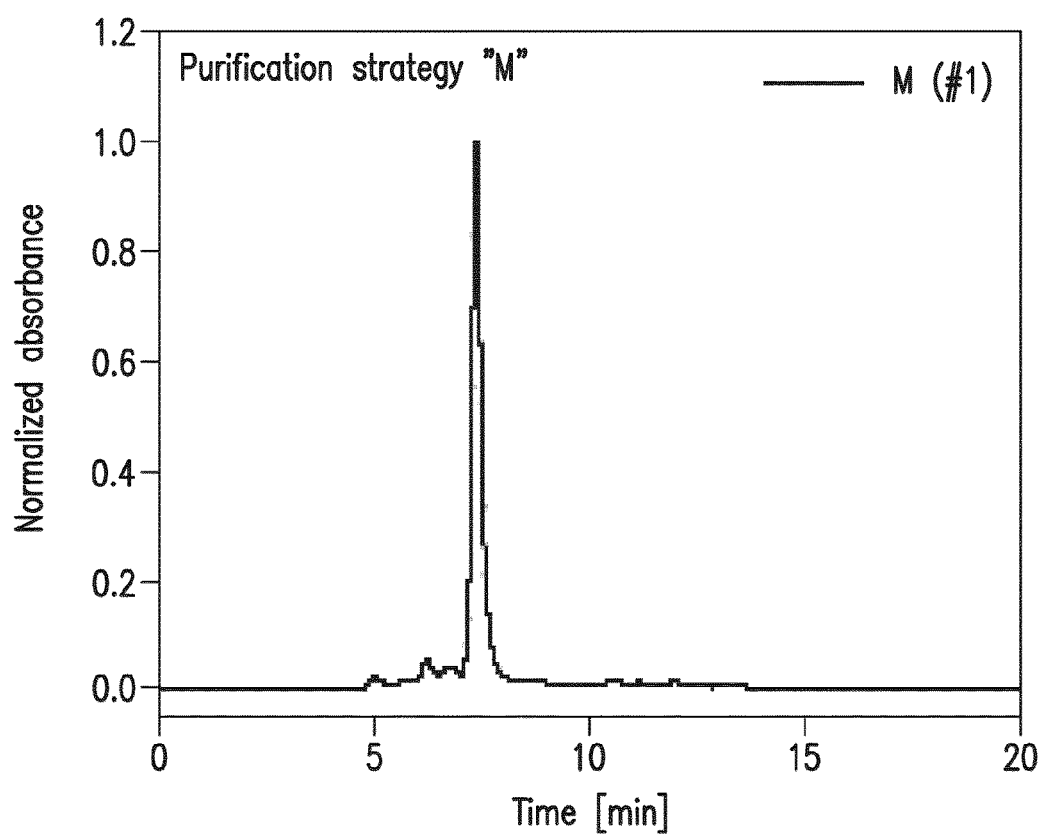
Figure 7C:
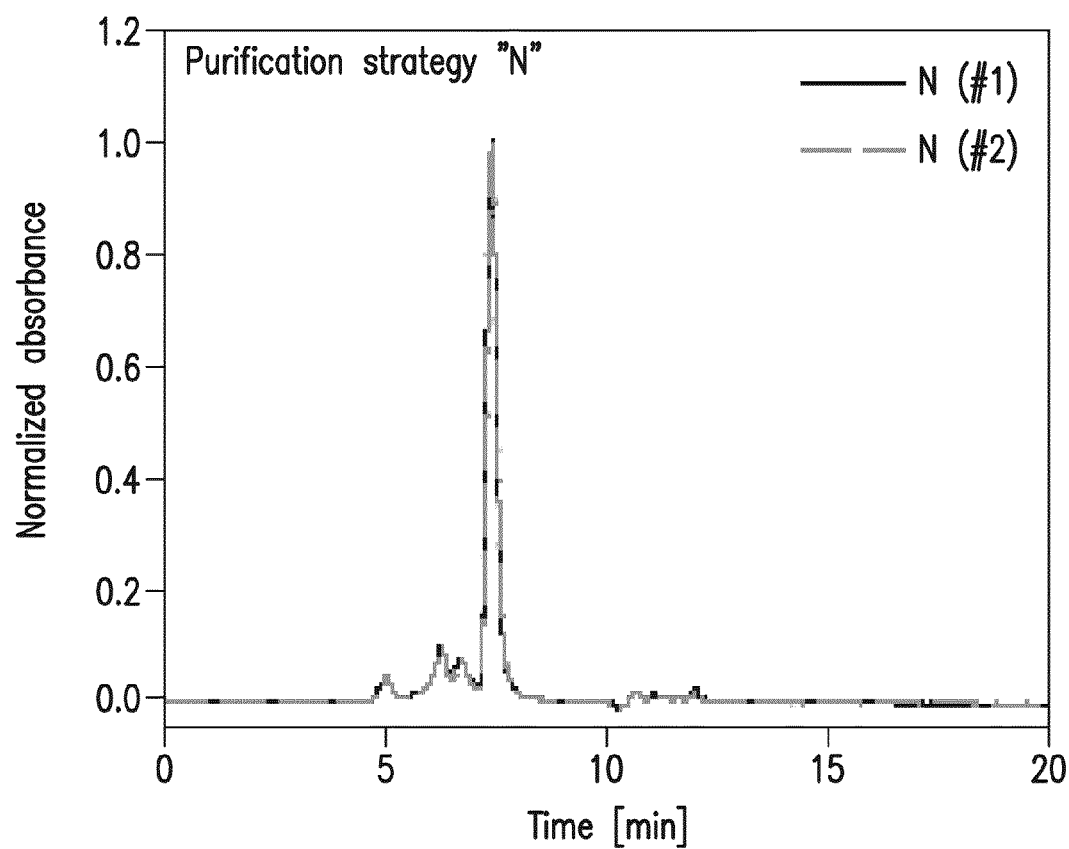
Figure 7D:
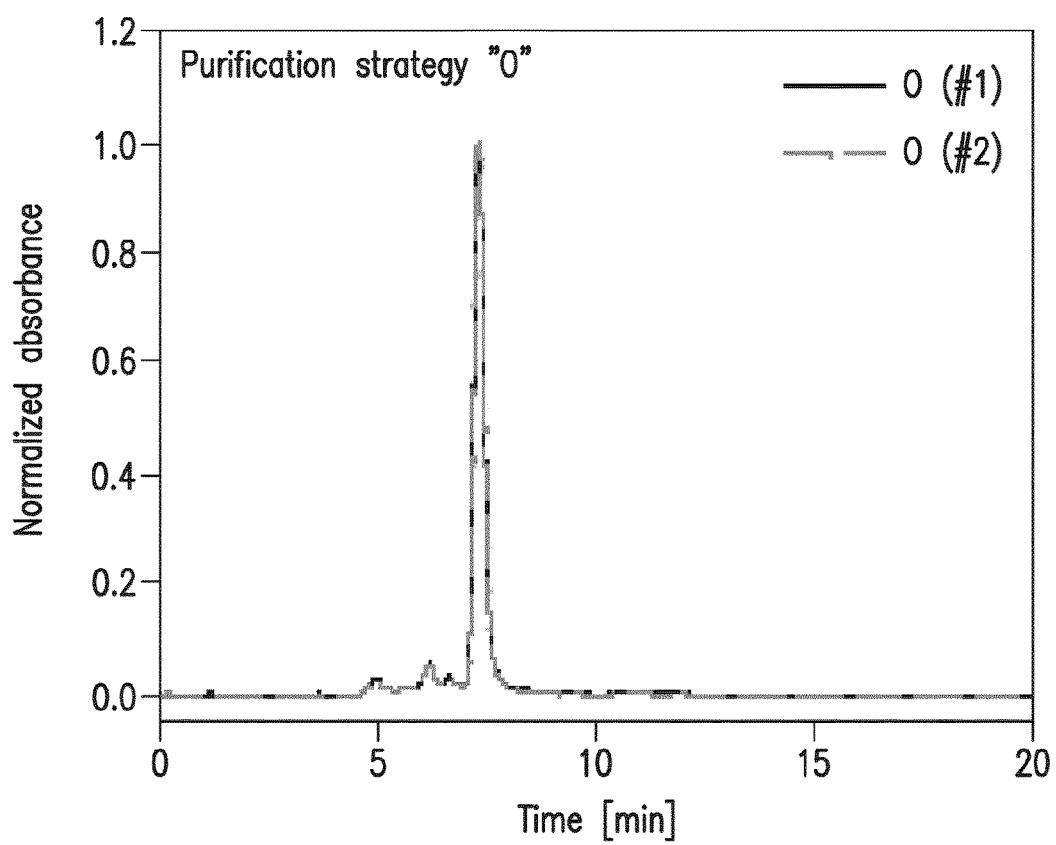
Figure 7E:
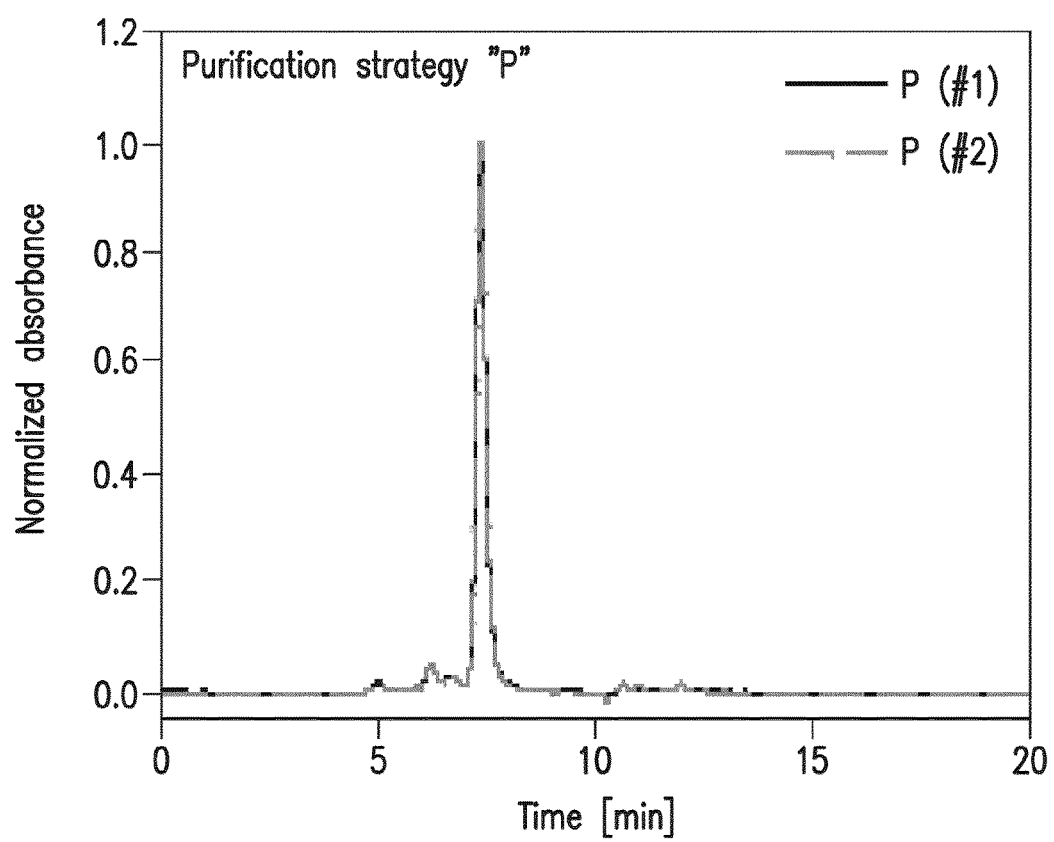
Figure 8A:
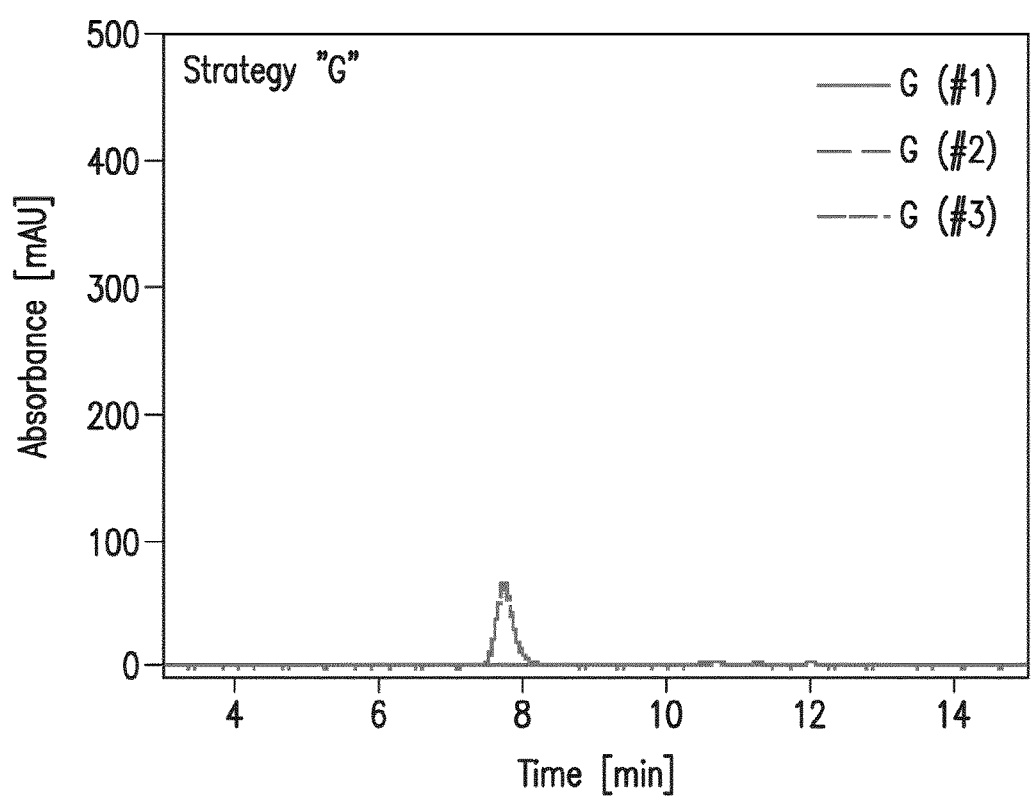
FIG. 8. SEC chromatograms for dissolved precipitates resulting from purification strategies G, I, C, J and K.
Figure 8B:
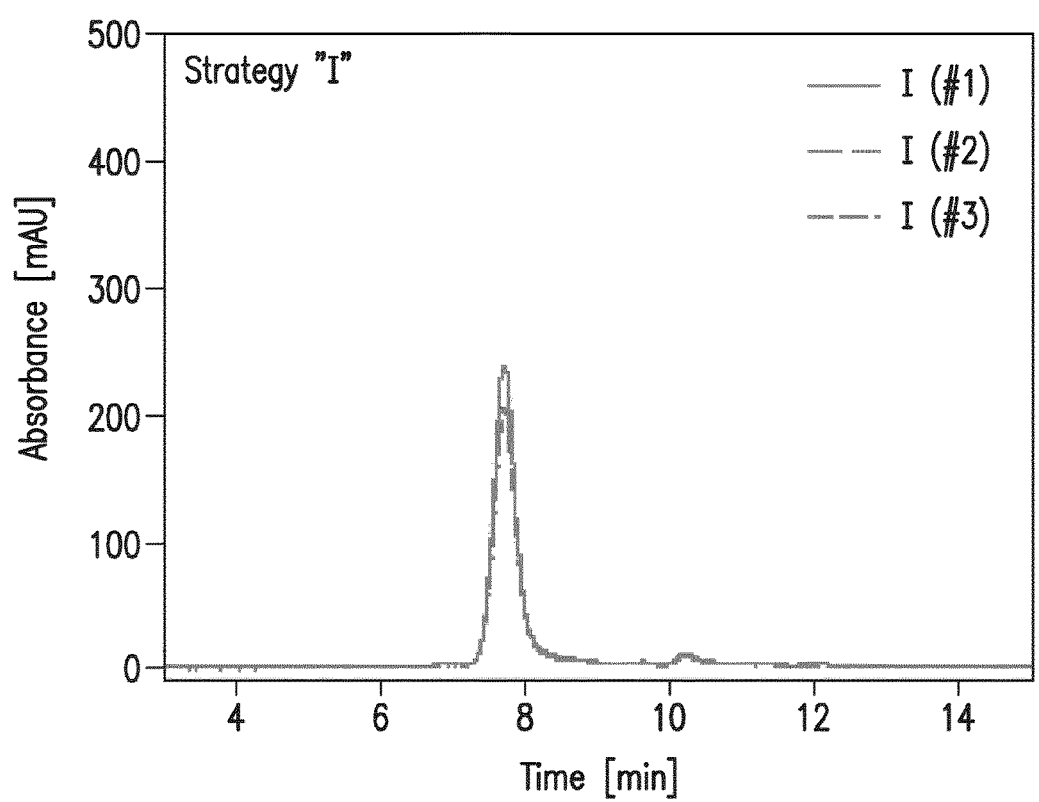
Figure 8C:
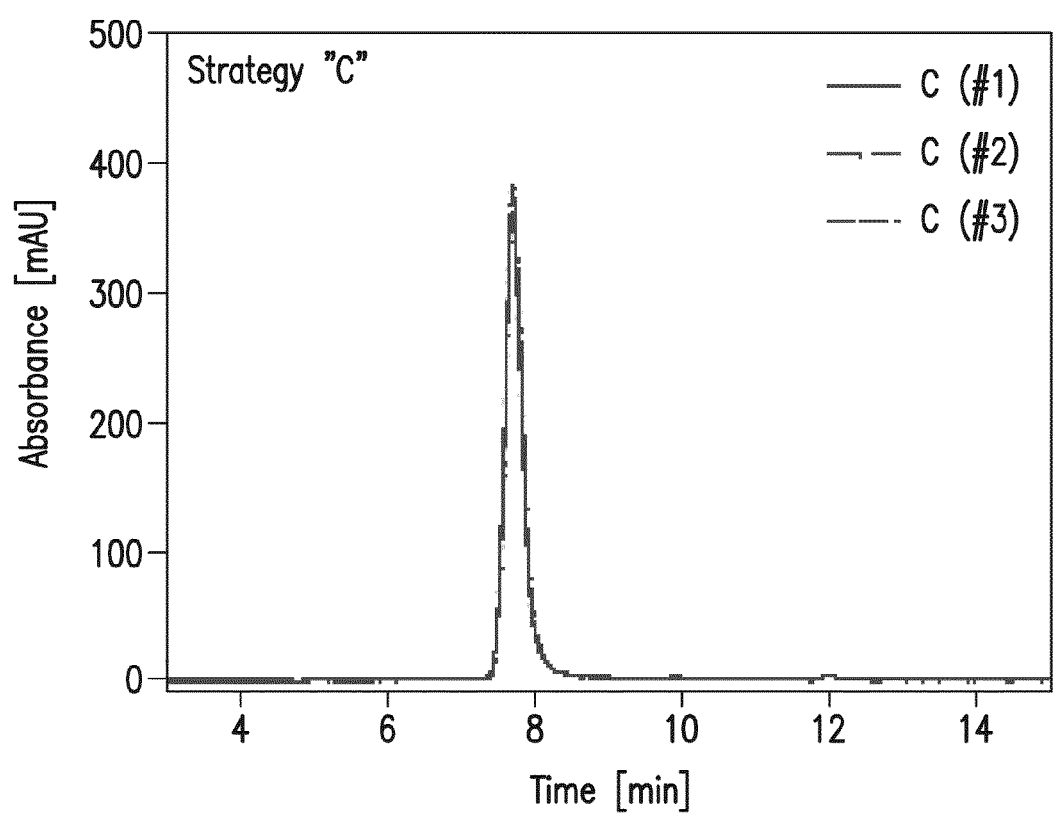
Figure 8D:
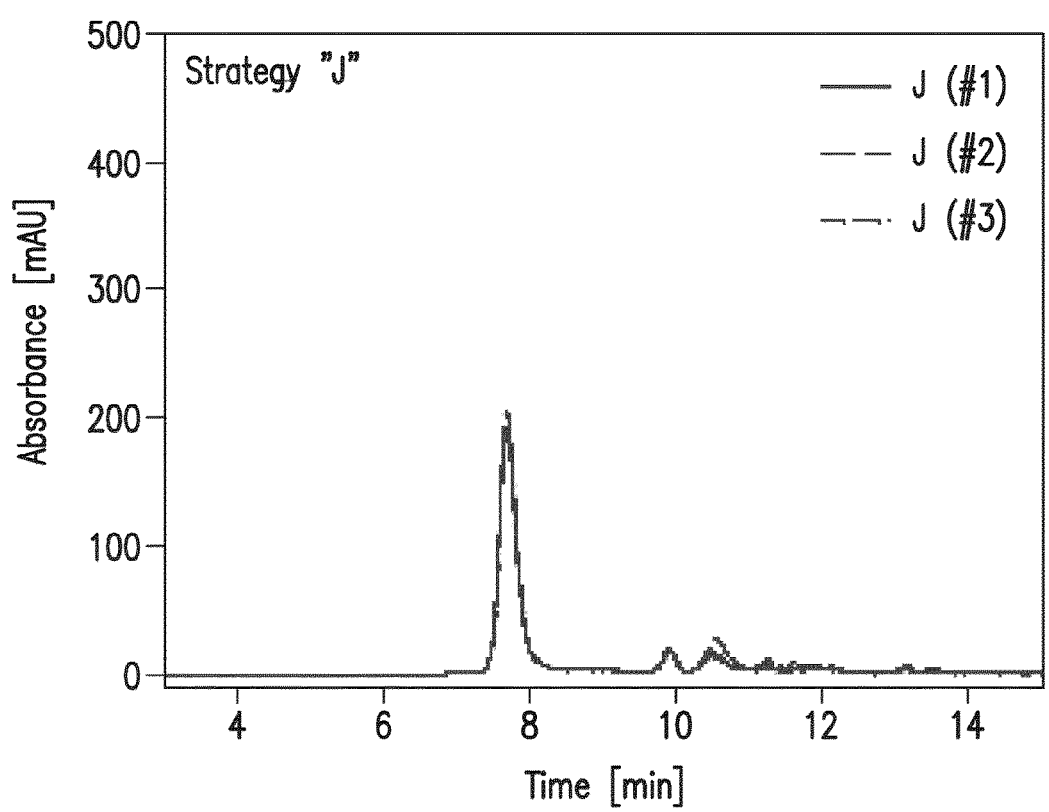
Figure 8E:
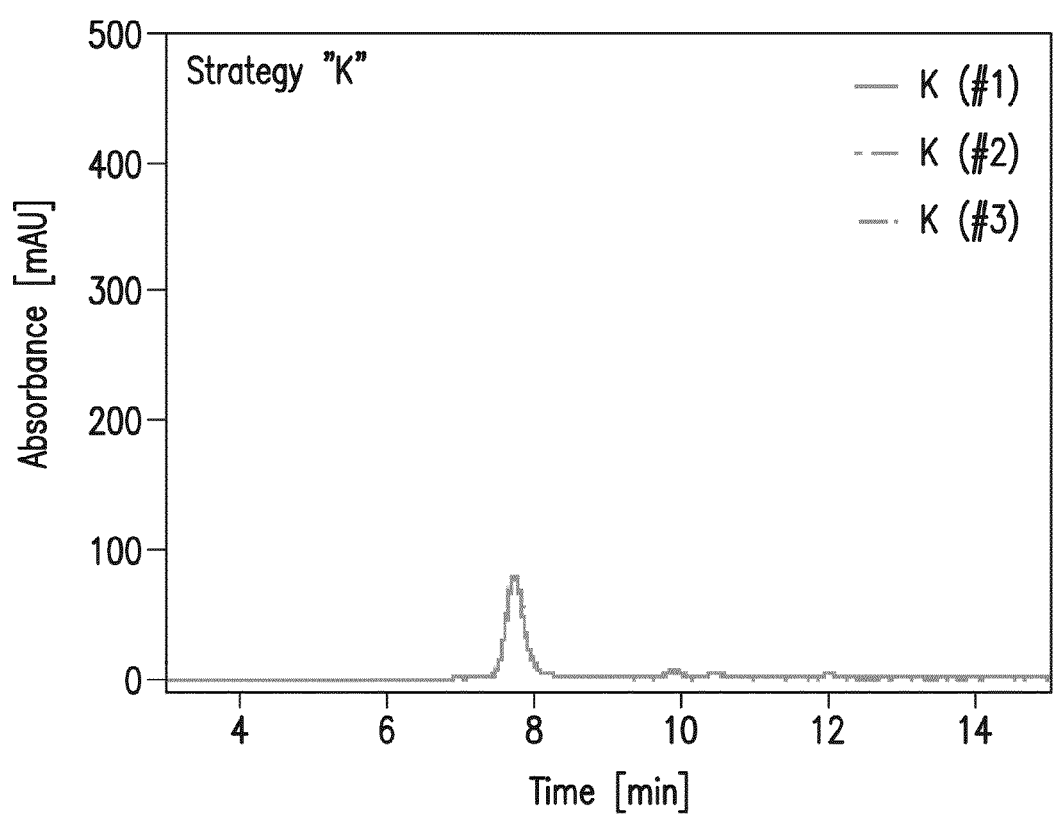
Figure 9A:
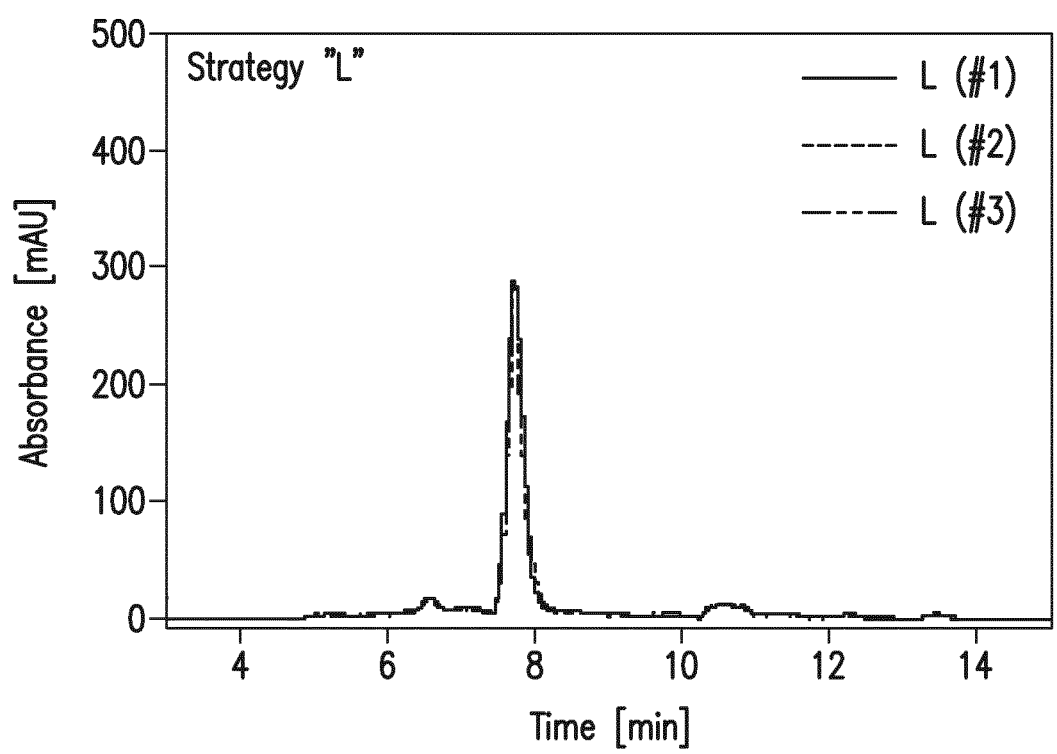
FIG. 9. SEC chromatograms for dissolved precipitates resulting from purification strategies L, M, P, N, O, and C.
Figure 9B:
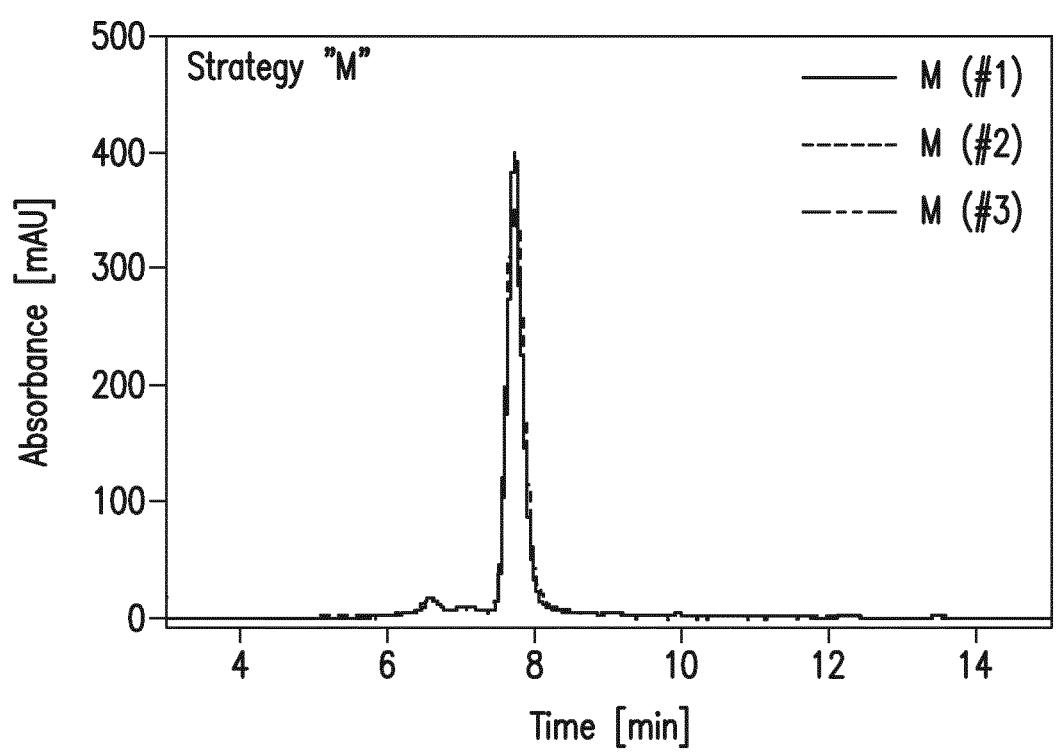
Figure 9C:
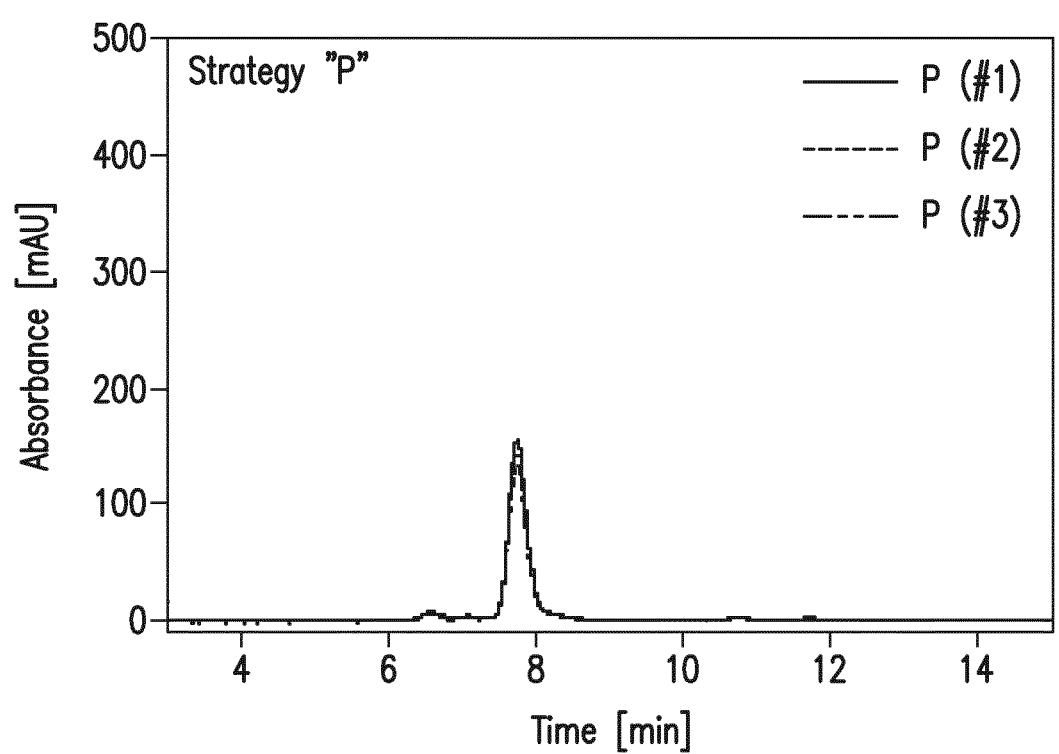
Figure 9D:
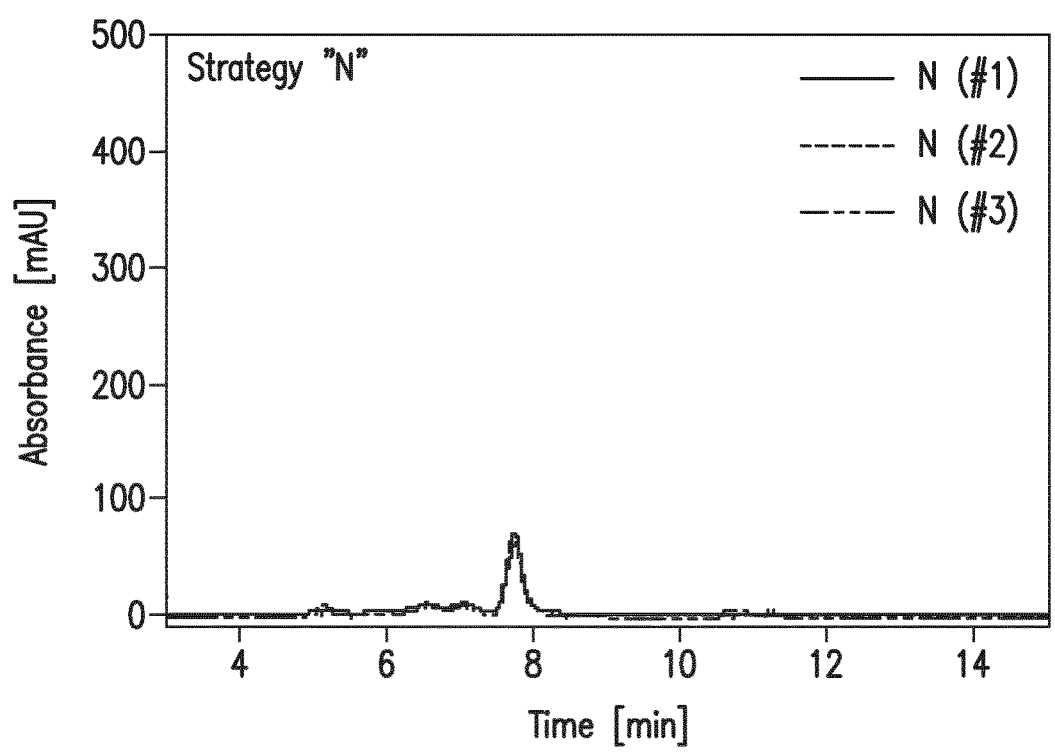
Figure 9E:
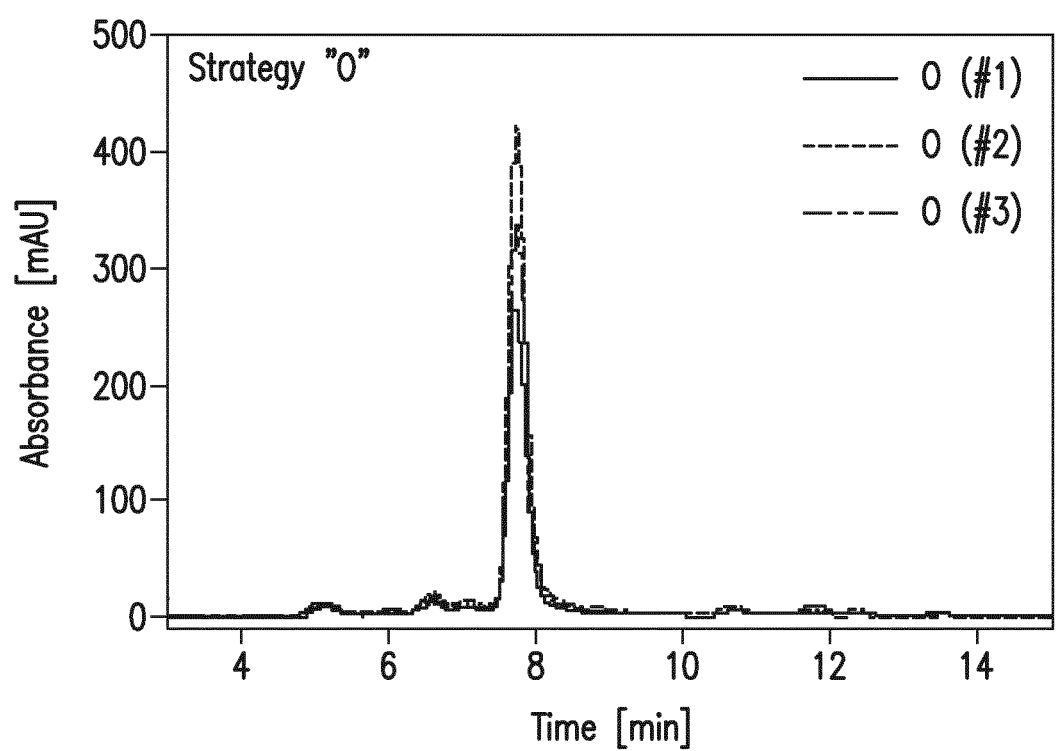
Figure 9F:
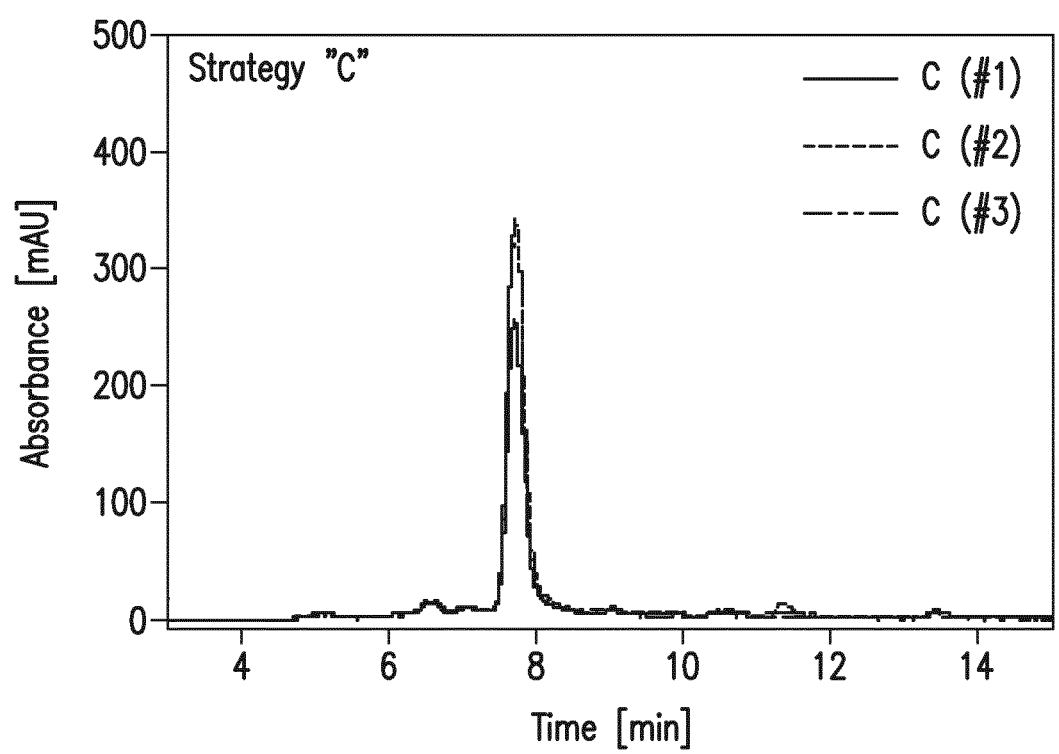

The plots of the main factors and selected interacting factors are provided in FIGS. 2 and 3. FIG. 2 illustrates the main and the interacting plots with the mass balance as the response function. On average, the mass balance was about 86%±6%. Considering the rather small scale (10 ml) of the reactions, this is not unexpected. Filter type and flow direction also displayed a slight impact. This correlates well with the minute percent contribution observed (Table 3). Washing of the precipitate had no effect on the mass balance. The most significant impact among the main factors is the factor of "drying of the precipitate in the filter" ("D"). It was determined that storage of the precipitate in the filter over longer periods (="drying") may not be advisable as it may lead to a decrease in yield (only 83% as compared to 89%).

The selection of the flow direction for dissolution (B) of the pellet should be selected depending on the filter (A) used (FIG. 2). While the planar filter resulted in only slightly better results when operated against flow, the depth filter is typically only applicable if the pellet is dissolved in flow. This was probably due to the difference in their structure. The planar filter is a symmetric filter while the depth filter is an asymmetric filter. Also, the evaluation of the interacting factors showed that drying of the precipitate when not washed leads to a significant decrease in mass balance (FIG. 2) while for the washed pellet no influence of drying was found. The mass balance for the unwashed pellet is typically higher than that of the washed pellet. As the mass balance and the yield are correlated, the same observations as for the mass balance are also true for the yield (FIG. 3). As mentioned previously, the yield may be low (40-50%) due to the low concentration of the antibody in the diluted cell culture supernatant. The washed, dissolved precipitate has a significantly higher purity (80%±2%) than the unwashed, dissolved precipitate (65%±3%).

Based on this data, a depth filter was tested for filtration as it allows a fast collection of the precipitate. The dilution during dissolution of the pellet due to the washing-out effect of the depth filter is at this scale acceptable. As given before, the depth filter is an asymmetric filter and the same flow direction need to be used throughout the experiment. Despite the loss of material, the effect of washing on purity is significant (~20% higher purity). A delay in dissolution of the precipitate results in material loss and will therefore also be avoided. Any precipitate recovered should typically be immediately dissolved after washing.

2. Comparison of Different Alcohols for Precipitation

The use of various alcohols to precipitate antibodies from cell culture supernatants was also tested. A list of alcohols tested in these experiments are shown in Table 4.

TABLE 4

| Alcohol | Properties | Comments |
| --- | --- | --- |
| Methanol | water soluble melting point: −98° C. | Toxic. Precipitation experiment. |
| Ethanol | water soluble melting point: −114° C. | Precipitation experiment. |
| 1-propanol | water soluble melting point: −127° C. | Not available. Precipitation experiment delayed. |
| Isopropanol | water soluble melting point: −88° C. | Precipitation experiment. |
| 1-Butanol | water soluble to ~11% (v/v) melting point: −89° C. | Not miscible with water. |
| Isobutanol | water soluble to ~11% (v/v) melting point: −108° C. | Not miscible with water. |
| Secondary butanol | water soluble ~11% (v/v) melting point: −114° C. | Not miscible with water. |
| Tertiary butanol | water soluble melting point: 26° C. | Too low melting point. |
| 1,2 Propandiol | water soluble melting point: −68° C. | No precipitation observed. |
| Acetone | water soluble melting point: −95° C. | No precipitation observed |

Figure 27A:
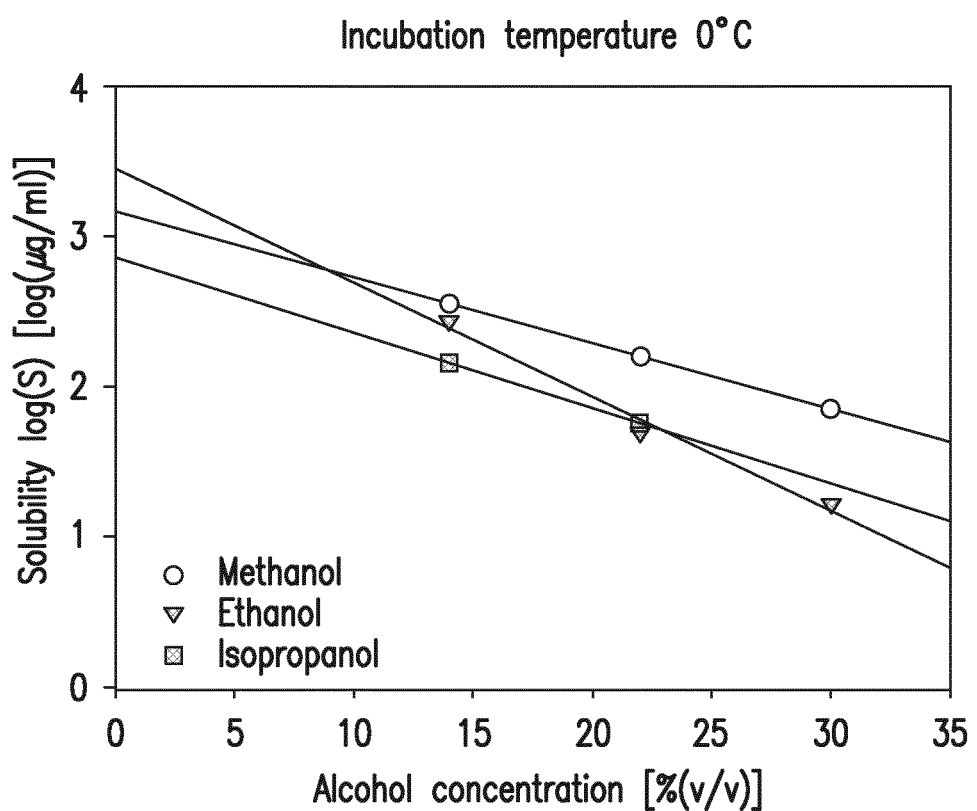
FIG. 27. Solubility curves of antibody for monoclonal antibody A supernatant using different alcohols at 0° C. (a) or −5° C. (b).
Figure 27B:
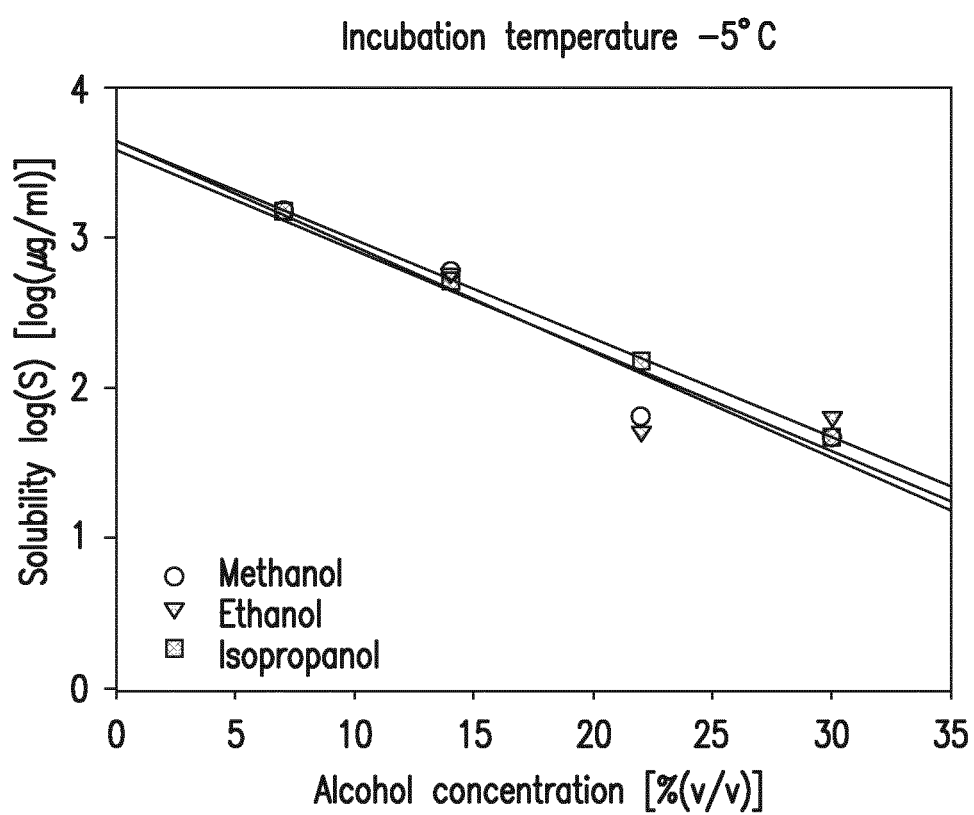
Figure 28A:
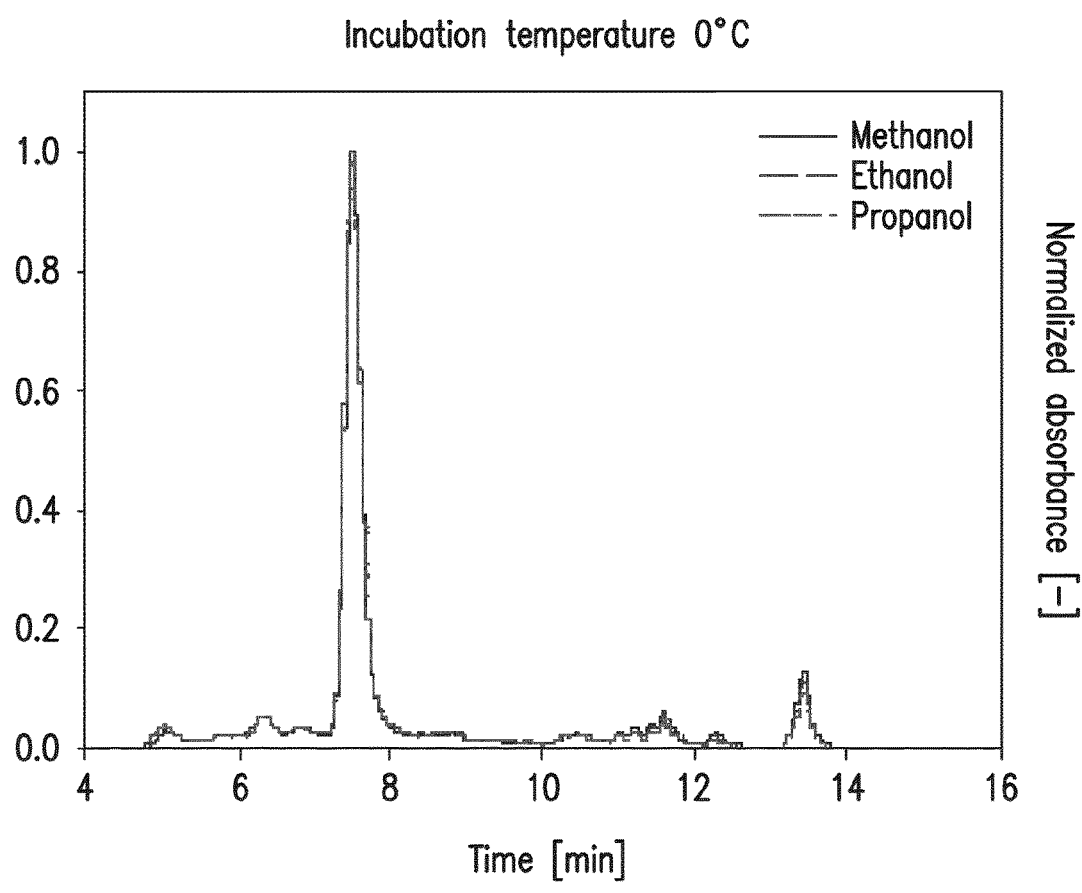
FIG. 28. SEC chromatogram of the dissolved precipitate prepared using methanol, ethanol, or isopropanol at 0° C. (a, b) or −5° C. (c, d).
Figure 28B:
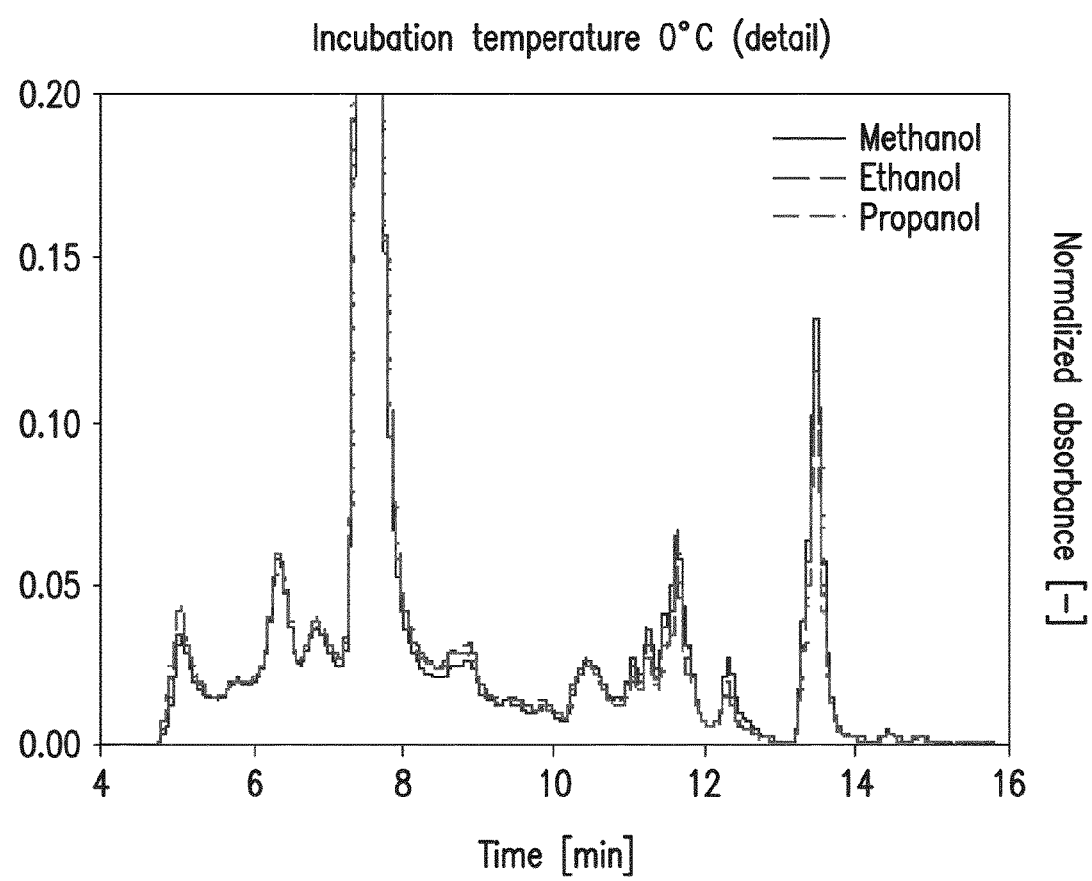
Figure 28C:
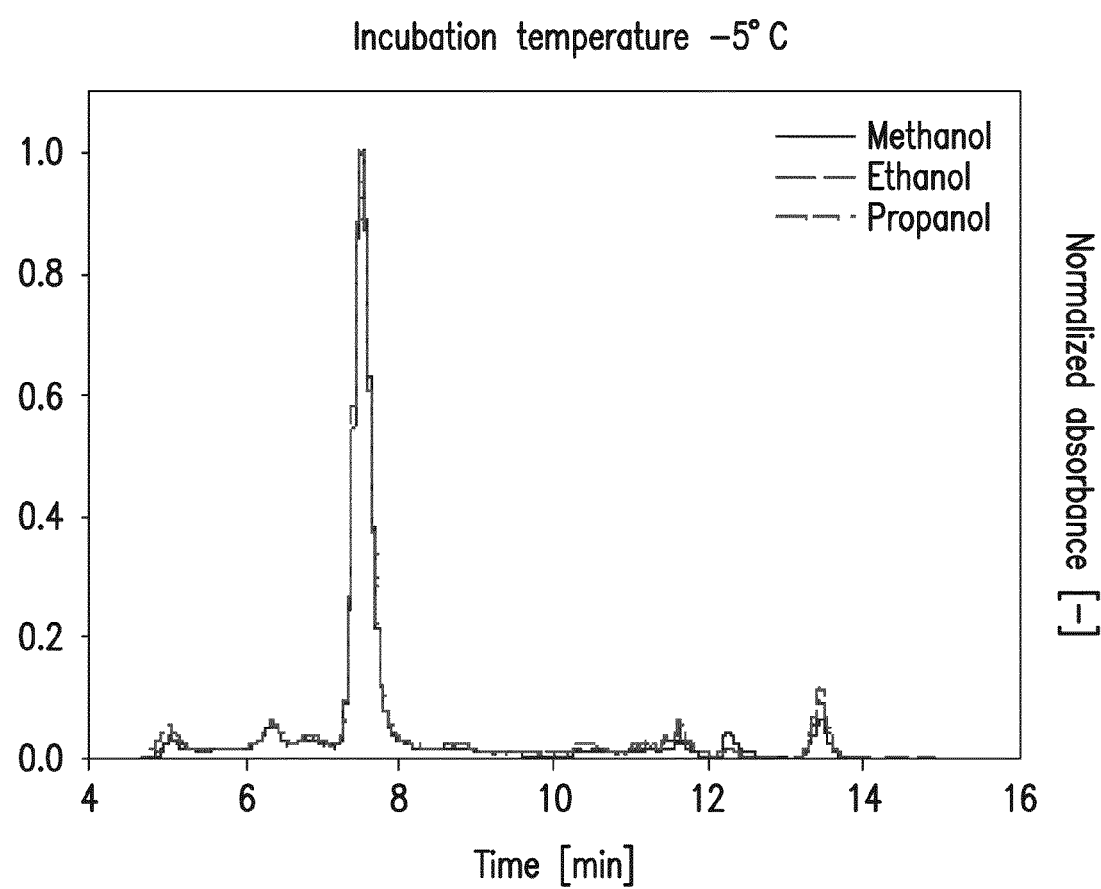
Figure 28D:
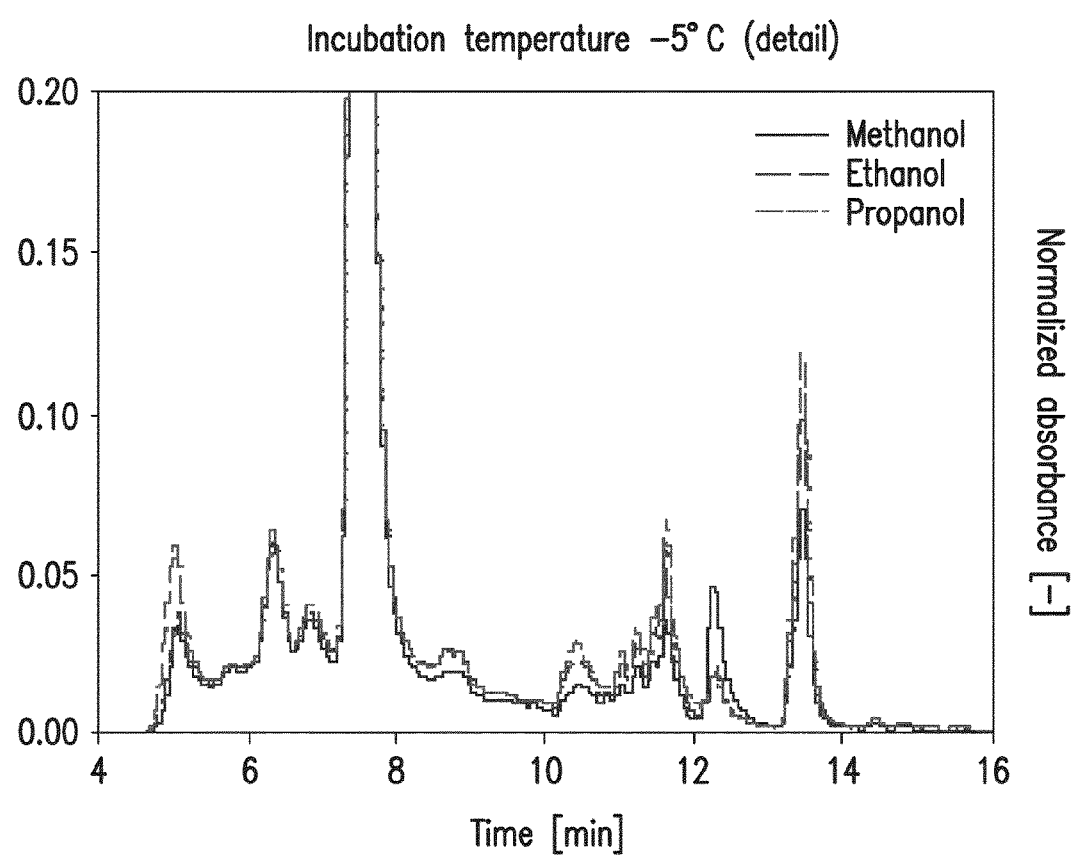

Methanol, similar to ethanol, is known to exhibit a low melting point and good water solubility. Ethanol was also tested. 1-propanol may also be suitable but was not tested in these experiments. Butanols are, with the exception of tertiary butanol, are only water soluble to a concentration of about 11% (v/v). Tertiary butanol is water-soluble and has a melting point of only 26° C. (making room temperature handling difficult). Acetone and 1,2-propandiol were also tested (both being water soluble and having relatively low melting points). However, precipitation was not observed using acetone or 1,2-propandiol precipitation under the conditions tested (5-30% (v/v) at 0° C. or −5° C.) (FIG. 27).

FIG. 28 illustrates the solubility curves of monoclonal antibody following precipitation using methanol, ethanol or isopropanol at 0° C. or −5° C. At −5° C., the solubility of monoclonal antibody A was very similar to precipitation at 0° C., although differences in slope and intercept were observed. Three data points are presented for each alcohol at 0° C. The data suggest that the behavior of the different alcohols is, at least at low temperatures, similar and that ethanol could be replaced by either methanol or isopropanol.

3. Optimization of $CaCl_2$ Precipitation

Figure 29A:
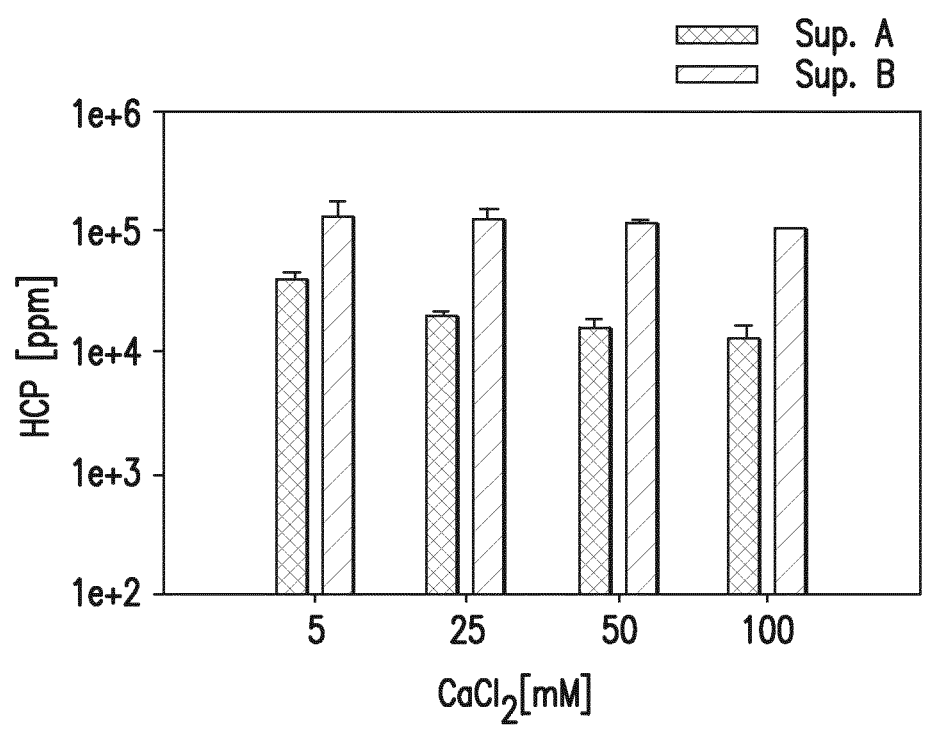
FIG. 29. Effects of $CaCl_2$ levels on impurities (A) and IgG purity (B).
Figure 29B:
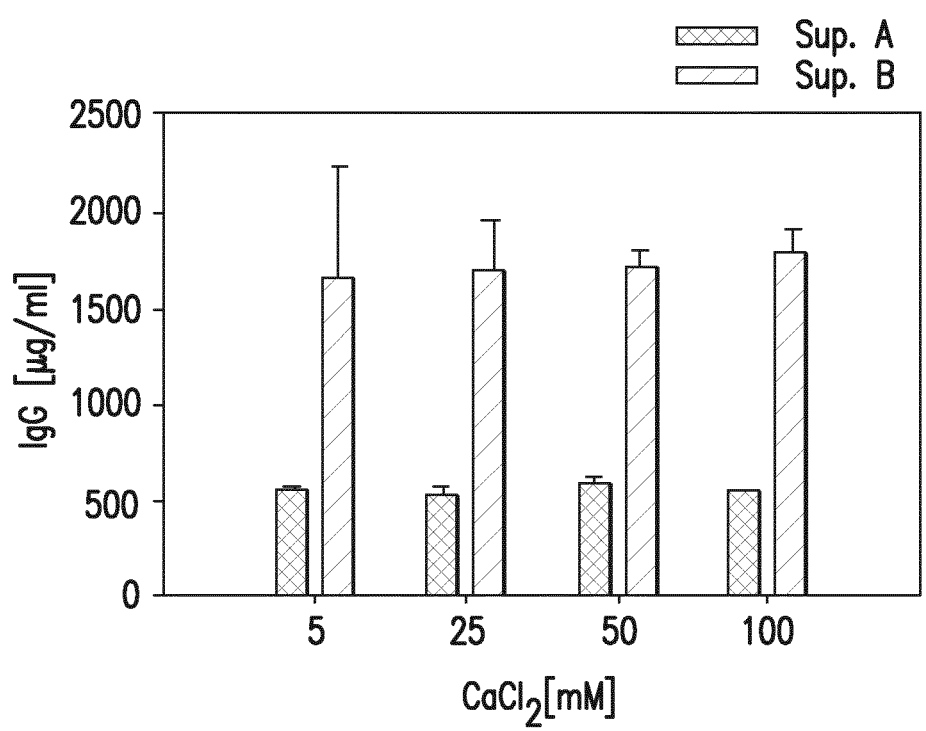

For the monoclonal antibody-containing cell culture supernatants A and C, $CaCl_2$ precipitation with varying concentrations of $CaCl_2$ (5-100 mM) and a subsequent ethanol precipitation (25% (v/v), −10° C.) were tested. As supernatant A has a higher phosphate concentration (~3.1 mM) than supernatant C (0.2 mM), $CaCl_2$ precipitation was expected to be more pronounced for supernatant A. $CaCl_2$ precipitation was performed at room temperature and pH 8.5 (adjusted using NaOH). The $CaCl_2$ precipitate was removed from the supernatant by centrifugation (4000 g, 15 min) and the pH of the supernatant brought to pH 6.5 using HCl. As shown in FIG. 29, the impurity (HCP) concentration of supernatant A is lower than for supernatant C, which is in agreement with the initial HCP concentration in the supernatants (supernatant A: 54212 ppm; supernatant C: 180099 ppm). FIG. 29 also shows that the $CaCl_2$ concentration in the first step has a significant influence on the final HCP level for supernatant A and a marginal influence for supernatant C. The IgG concentration is almost independent of $CaCl_2$ concentration used in the first step for both of the tested supernatants. A larger standard deviation can be found at lower $CaCl_2$ concentrations for supernatant A.

Figure 30A:
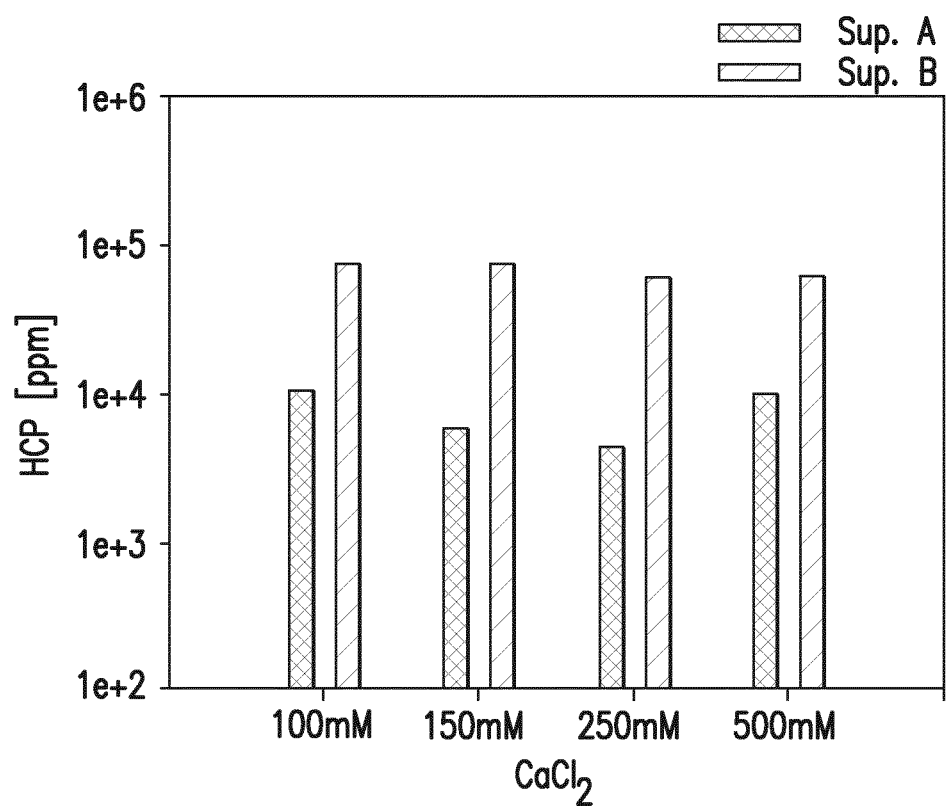
FIG. 30. Effects of $CaCl_2$ levels on impurities (A) and IgG purity (B).
Figure 30B:
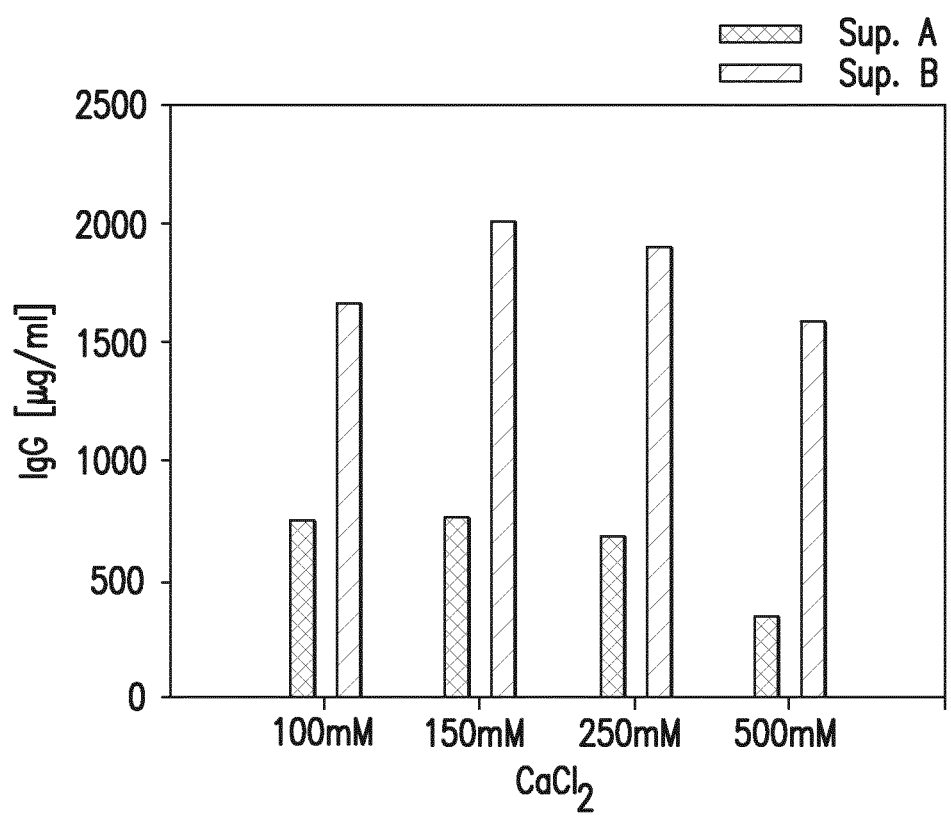

Higher $CaCl_2$ concentrations were also test (500 mM; FIG. 30). As shown in FIG. 2-11B, impurity (HCP) concentration decreases further for supernatant A to 250 mM $CaCl_2$ while it remains almost constant for supernatant C. The increase of HCP concentration for supernatant A at 500 mM $CaCl_2$ is due to the significant loss of IgG. The optimum $CaCl_2$ concentration for HCP removal was therefore determined to be about 150-250 mM.

Figure 31:
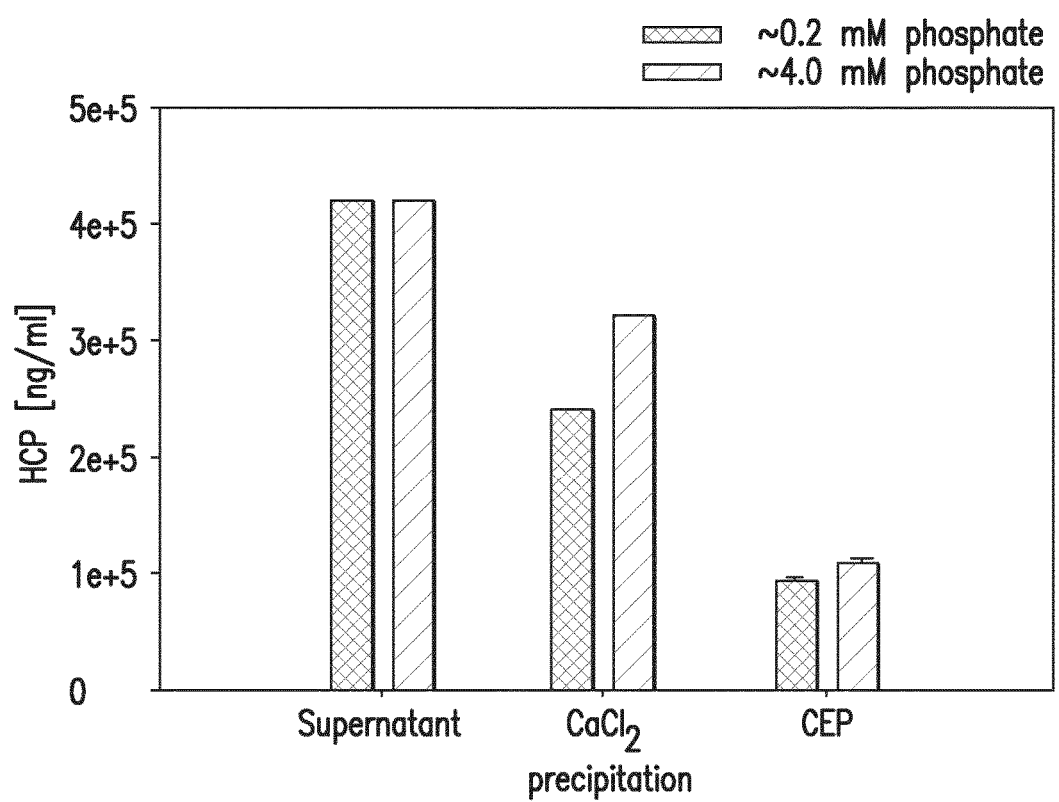
FIG. 31. Effects of $CaCl_2$ levels on impurities.
Figure 32A:
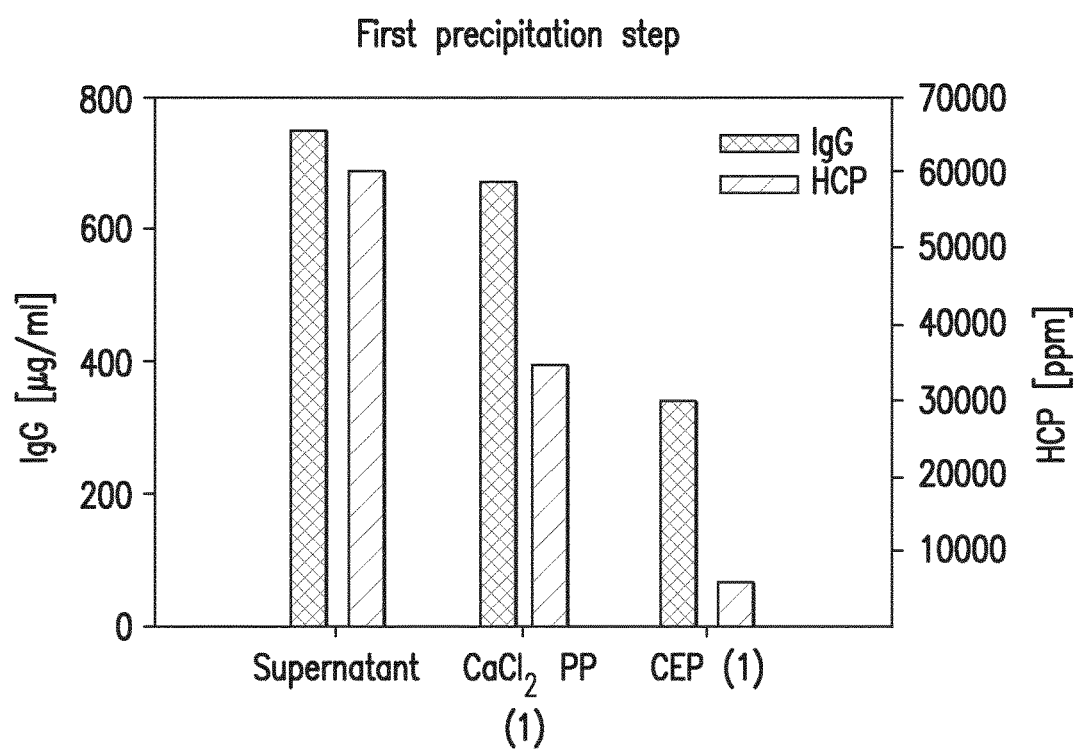
FIG. 32. IgG purity following first precipitation step (A), second precipitation step (B), second precipitation step ($CaCl_2$ addition (C)), and second precipitation step (NaCl addition (D)).
Figure 32B:
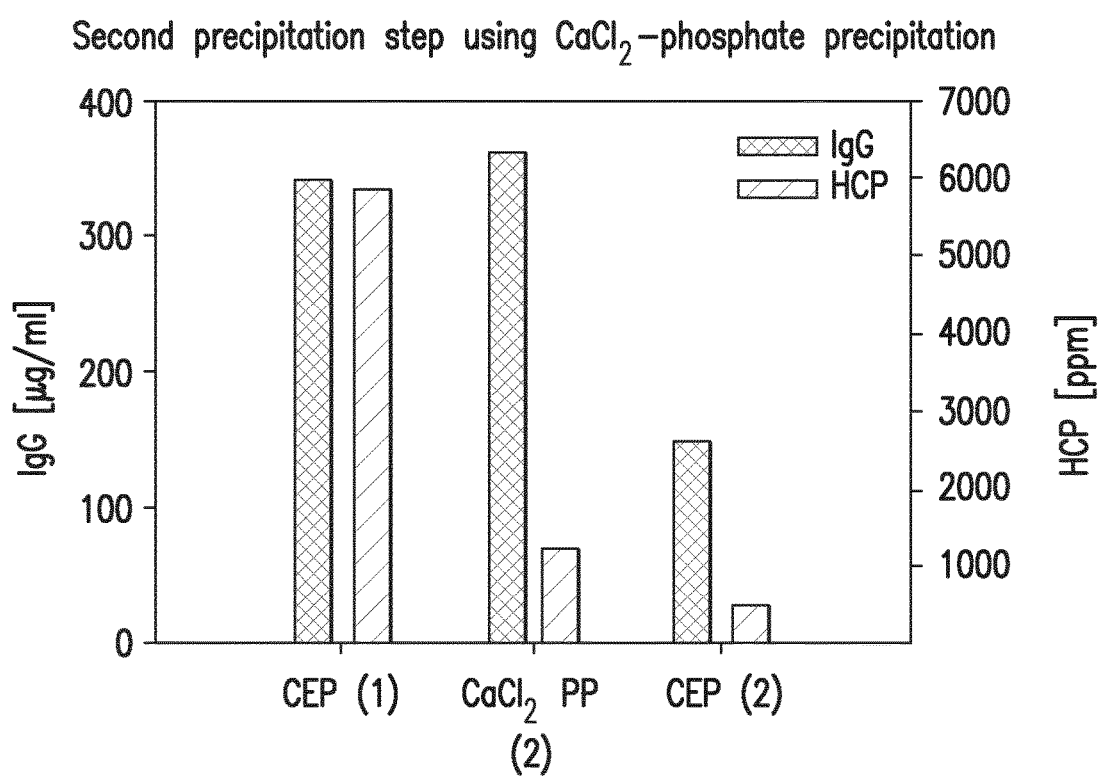
Figure 32C:
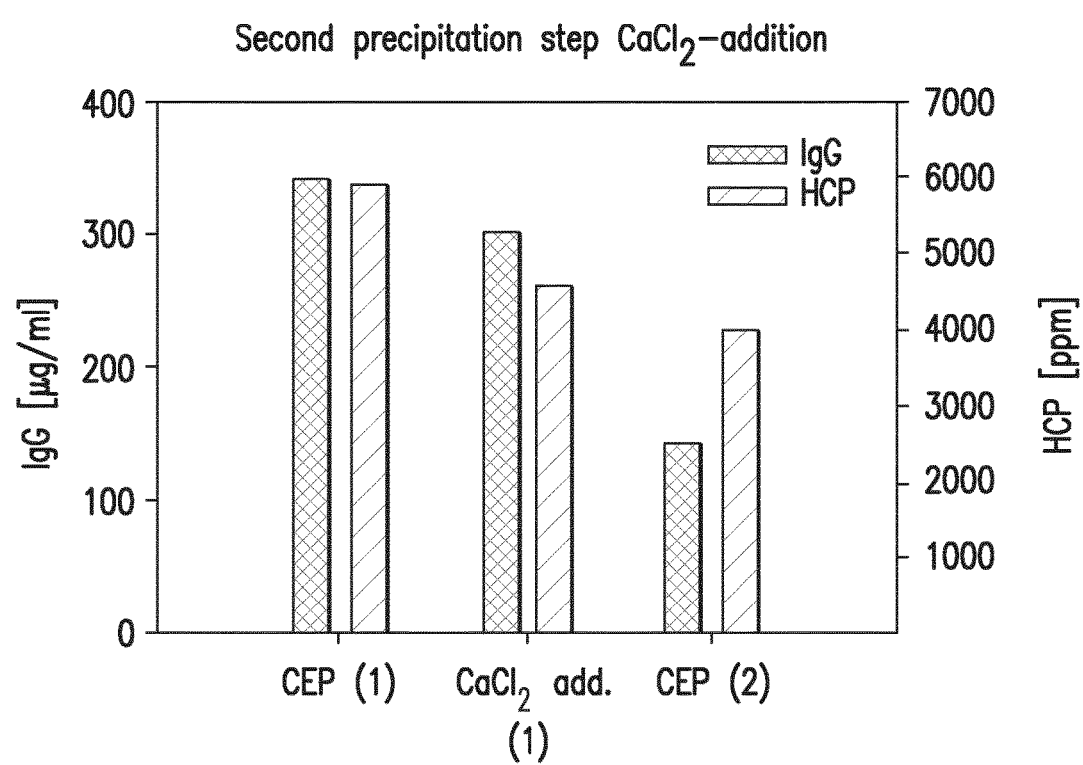
Figure 32D:
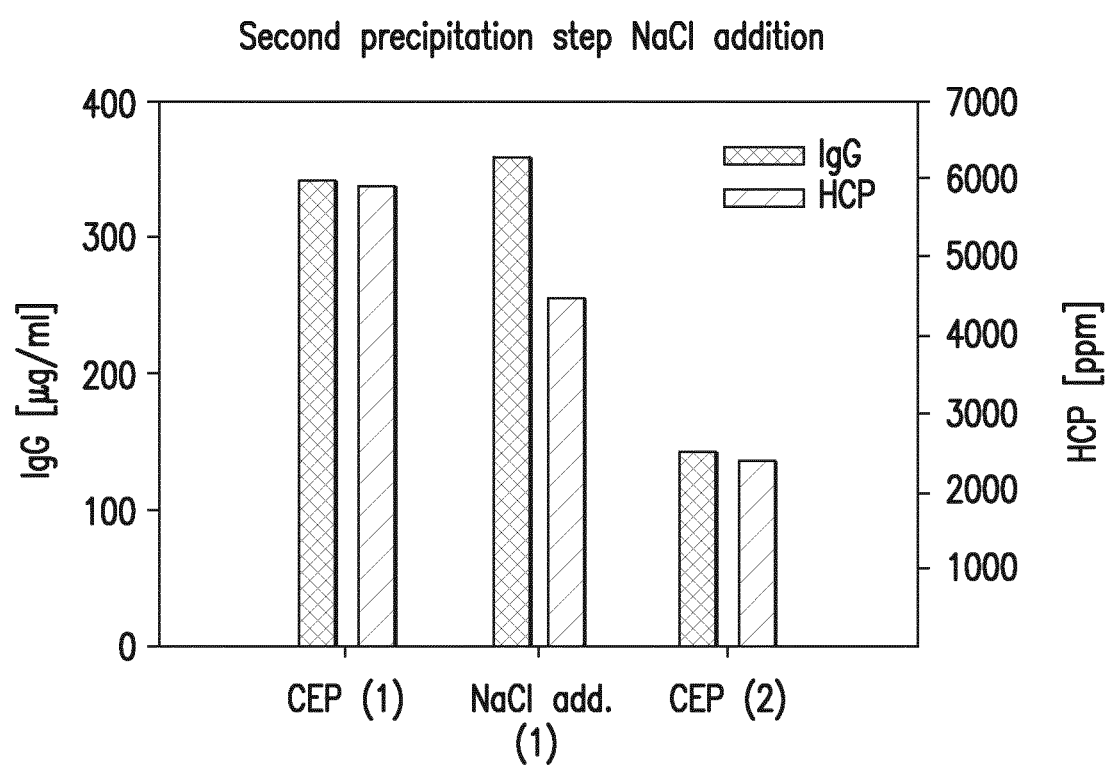

As shown below, phosphate concentration may improve isolation of monoclonal antibodies from cell culture supernatant. The phosphate concentration of supernatant A is higher than for supernatant C, which could result in a stronger influence of $CaCl_2$ on HCP removal. The isolation of monoclonal antibody from supernatant C by $CaCl_2$ precipitation and cold ethanol precipitation (CEP) in the presence of elevated phosphate concentrations was therefore tested. Phosphate was added to a final concentration of 4.0 mM to the supernatant, and then $CaCl_2$ precipitation and CEP were carried out. The results were compared with supernatant containing the "original" phosphate concentration of about 0.2 mM phosphate. As shown in FIG. 31, the addition of phosphate did not significantly change the results.

To determine if the effect on HCP reduction is due to $CaCl_2$-phosphate precipitation or the high conductivity caused by $CaCl_2$, the following purification strategies were compared for supernatant A. As the supernatant contains the IgG in a rather complex matrix, the first $CaCl_2$ precipitation and CEP aimed to obtain a relatively pure IgG in a defined matrix (20 mM histidine, 150 mM NaCl, pH 6.0). Therefore, impurities were first removed by addition of $CaCl_2$ to a final concentration of 250 mM. The supernatant was subsequently subjected to CEP using 25% (v/v) ethanol (final concentration) (−10° C., 2 h). The dissolved precipitate was then divided into three parts. To one part, first 300 mM $Na_2HPO_4$ was added to a final concentration of 4 mM phosphate followed by 4000 mM $CaCl_2$ to a final concentration of 250 mM $CaCl_2$. The other two parts were mixed with $CaCl_2$ to a final concentration of 250 mM or NaCl to a final concentration of 500 mM. NaCl required a higher concentration to obtain a similar conductivity as for 250 mM $CaCl_2$ (~50 mS/cm). As shown in FIG. 32, reduction of impurities is more effective when repeating $CaCl_2$ precipitation and CEP (FIG. 32(A)) than by increasing the conductivity of the second CEP step (FIG. 32(C,D)). And when (only) salt is added to increase the conductivity before the second CEP step, NaCl may be more efficient (~2500 ppm) than $CaCl_2$ (~4000 ppm). While it is possible to increase conductivity to improve HCP reduction during CEP, it may be more advisable to perform a second $CaCl_2$ precipitation.

4. Isolation of Monoclonal Antibodies from Monoclonal Antibody-containing Cell Culture "Supernatant A".

Six different purification strategies were compared (Table 5) to determine the optimal conditions for purification of monoclonal antibody from monoclonal antibody-containing supernatant A ("supernatant A" containing monoclonal antibody having a pI~9.2) from cell-free culture supernatant.

TABLE 5

| Purification strategy | Salt type | Conductivity [mS/cm] | pH | Ethanol [%(v/v)] | Temperature [° C.] | IgG [µg/ml] | Predicted solubility (Jungbauer et al. 2010c) Protein impurities [µg/ml' | DNA [ng/ml] |
|---|---|---|---|---|---|---|---|---|
| A | $CaCl_2$ | 20 | 8.5 | 5 | 4.0 | 23350 | 11 | 3 |
|   | $CaCl_2$ | 20 | 8.5 | 30 | −10.0 | 98 | 98 | 17 |
| B | $CaCl_2$ | 20 | 7.5 | 5 | 4.0 | 8545 | 31691 | 3 |
|   | $CaCl_2$ | 20 | 7.5 | 30 | −10.0 | 98 | 519 | 50 |
| C | $CaCl_2$ | 20 | 8.5 | 0 | 4.0 | 22756 | 2759 | 37 |
|   | $CaCl_2$ | 20 | 6.5 | 25 | −10 | 9 87 | 1460 | 127 |
| D | NaCl | 10 | 6.5 | 25 | −10.0 | 64 | 1330 | 105 |
| E | Clarified cell culture supernatant |  |  | 25 | −10 |  | Not available. |  |
| F | 1:4 diluted |  |  | 25 | −10 |  | Not available |  |

The first two purification strategies, "A" and "B" use $CaCl_2$ to precipitate impurities. "A" operates at a high pH and the initial $CaCl_2$ precipitation coupled with ethanol should allowing removal of DNA and also protein impurities in the first step. In the second step the ethanol concentration is increased and the temperature decreased for precipitation of the antibody. In case of "B" the same conditions are applied only the pH is lower, 7.5 instead of 8.5. This should result in less removal of the protein impurities. However, this method might be advantageous as the higher pH in method "A" could result in unwanted modifications of the antibody. Strategy "C" is also similar, though slightly different ethanol concentrations are used. The initial precipitation using $CaCl_2$ is performed at pH 8.5 while the second precipitation is then performed at pH 6.5 As the first precipitation step is a fast reaction (~10 minutes), the high pH should not lead to antibody modification.

Strategy "D" uses NaCl instead of $CaCl_2$ and aims at keeping the impurities soluble while the antibody is selectively precipitated. The two remaining precipitation strategies, "E" and "F", are used as reference methods where the clarified cell culture supernatant is used without further adjustments except a 1:4 dilution in case of strategy "F". For simplicity we analysed only the dissolved precipitates (Table 6).

TABLE 6

|  | A | B | C | D | E | F |
|---|---|---|---|---|---|---|
| IgG [µg/ml] | 589 ± 6 | 639 ± 36 | 643 ± 47 | 569 ± 213 | 591 ± 96 | 136 ± 14 |
| Protein impurities [µg/ml] | 51 ± 23 | 7 ± 16 | 1 ± 28 | 310 ± 63 | 324 ± 170 | 276 ± 24 |
| DNA[ng/ml] | 109 ± 8 | 99 ± 42 | 120 ± 16 | 140 ± 45 | 220 ± 50 | 58 ± 42 |
| Yield (overall) | 68% | 71% | 77% | 59% | 59% | 54% |
| Purity | 92% | 99% | 100% | 65% | 65% | 33% |
| DNA [ppm] | 185 | 155 | 187 | 246 | 372 | 426 |

The antibody concentration is quite similar for all fractions except the method "F", which is likely because the supernatant used for method "F" was diluted 1:4. Strategies "B" and "C" are advantageous over the other methods with respect to purity. Compared to "A" this is not unexpected as "A" results in a significant precipitation of protein impurities. The large amount of precipitated protein impurity resulting from strategy D was rather surprising. The amount of DNA recovered using strategies "A", "B", "C" and "D" was quite similar, which was unexpected considering the predicted solubility. The overall yield of the different purification strategies was about 59-80%. This was found to be due to the temperature difference of the precipitate suspension (−10° C.) and the syringes and filters (room temperature). Additionally, also a rather high stirrer speed was used (1000 rpm) and this might have also affected the recovery. The purity for the capture step was determined by Bradford and analytical protein A chromatography. For strategies "A", "B", and "C", rather high purities were observed. DNA removal may be improved using, for example, additional precipitation steps.

Comparison of the analytical SEC chromatograms of the different purification strategies are given in FIG. 5. As shown therein, strategies "A", "B" and "C" result in higher purity than strategies "D", "E", and "F". These strategies provided for the removal of high molecular weight impurities, presumably consisting mainly of DNA. Low yields may be improved using depth filters. Strategy "A" may be replaced by strategy "B", with no significant loss in purity or recovery.

5. Isolation of Monoclonal Antibodies from Monoclonal Antibody-containing Cell Culture "Supernatant B".

Five different purification strategies were evaluated to determine the optimal conditions for purifying monoclonal antibody from monoclonal antibody-containing cell culture supernatant B ("supernatant B" containing the same antibody as A, but produced using a different cell line; pI~9.2), as summarized in Table 7.

TABLE 7

| Purification strategy | Salt type | Conductivity [mS/cm] | pH | Ethanol [%(v/v)] | Temperature [° C.] | IgG [µg/ml] | Predicted solubility (Jungbauer et al. 2010c) Protein impurities [µg/ml'] | DNA [ng/ml] |
|---|---|---|---|---|---|---|---|---|
| G | CaCl$_2$ | 20 | 6.5 | 5 | −0.5 | 25528 | 1 | 41694 |
|  | CaCl$_2$ | 70 | 6.5 | 10 | −3.4 | 10870 | 1066 | 266 |
|  | CaCl$_2$ | 70 | 6.5 | 40 | −10 | 129 | 184 | 2516 |
| H | CaCl$_2$ | 28 | 7.5 | 5 | 4.0 | 126321 | 0 | 44328 |
|  | CaCl$_2$ | 28 | 7.5 | 5 | −5.3 | 33426 | 7 | 113 |
|  | CaCl$_2$ | 28 | 7.5 | 40 | −10 | 357 | 75 | 1836 |
| I | NaCl | 20 | 7.5 | 40 | −10.0 | 79 | 442 | 18 |
| J | Clarified cell culture supernatant |  |  | 40 | −10 |  | Not available |  |
| K | 1:4 diluted |  |  | 40 | −10 |  | Not available. |  |

Purification from supernatant B could be performed at medium to low pH. The two initial purification steps of the strategy "G" aim at the removal of protein impurities and DNA and the third step is for the final precipitation of antibody. Strategy "H" may be more efficient in removal of protein impurities or DNA but may be less efficient in the precipitation of antibody in the third step. Strategy "I" aims at the selective precipitation of antibody while keeping the protein impurities and the DNA in solution. The overall yield of the different purification strategies is about 25-50% (Table 8).

TABLE 8

|  | G | H | I | J | K |
|---|---|---|---|---|---|
| IgG [µg/ml] | 885 ± 116 |  | 1211 ± 719 | 785 ± 64 | 462 ± 18 |
| Protein impurities [µg/ml] | 1 ± 31 | IgG was not | 313 ± 33 | 112 ± 78 | 85 ± 108 |
| DNA [ng/ml] | 122 ± 23 | precipitated | 379 ± 262 | 173 ± 20 | 327 ± 300 |
| Yield (step/overall) | 47% |  | 41% | 24% | 25% |
| Purity | 100% |  | 79% | 88% | 57% |
| DNA [ppm] | 138 |  | 313 | 220 | 708 |

In particular, the unmodified and diluted supernatant only 25% yield was obtained. Again we assumed that this was due to the temperature difference of the precipitate suspension (−10° C.) and the syringes and filters (room temperature) and the rather high stirrer speed (1000 rpm). Besides the low yield, strategy "G" seems already quite promising; the dissolved precipitate is of high purity and compared to the other methods the DNA concentration is low. Surprisingly, precipitation was not observed using strategy "H". This may be due to a pH shift upon temperature reduction, perhaps because the buffering capacity of the cell culture supernatant is lower at pH 7.5 than at 6.5. Strategy "I", which aims to selectively precipitate antibody while keeping protein impurities and DNA in solution, resulted in low purity and low yield. The reference strategies using the pure ("J") and diluted ("K") cell culture supernatant also resulted in low yield. Comparing the SEC chromatograms (FIG. 6) all strategies except strategy "G" seem to give dissolved precipitates of high purity. Even the dissolved precipitates of the strategies "J" and "I" have, in contrast to the measured purity given in Table 8, a rather high purity.

A modified Strategy C was also used to isolation monoclonal antibody from supernatant B (Tables 9 and 10). It was surprisingly found that the solubility of the resulting monoclonal antibody was different from that isolated from supernatant A using the same procedures (e.g., as the monoclonal antibodies in A and B differ only in that each is prepared using a different cell line).

TABLE 9

| Purification strategy | Salt type | Conductivity [mS/cm] | pH | Ethanol [%(v/v)] | Temperature [° C.] | IgG [µg/ml] | Predicted solubility (Jungbauer et al. 2010c) Protein impurities [µg/ml'] | DNA [ng/ml] |
|---|---|---|---|---|---|---|---|---|
| C | $CaCl_2$ | 29 | 8.5 | 0 | 4.0 | 1865316 | 80406.0 | 0.0 |
|   | $CaCl_2$ | 29 | 6.5 | 25 | -10 | 1228.6 | 436.8 | 9.9 |
| G | $CaCl_2$ | 29 | 6.5 | 5 | -0.5 | 25528 | 1 | 41694 |
|   | $CaCl_2$ | 79 | 6.5 | 10 | -3.4 | 10870 | 1066 | 266 |
|   | $CaCl_2$ | 70 | 6.5 | 40 | -10 | 129 | 184 | 2516 |
| I | NaCl | 20 | 7.5 | 40 | -10.0 | 79 | 442 | 18 |
| J | Clarified cell culture supernatant | | | 40 | -10 | | Not available | |
| K | 1:4 diluted | | | 40 | -10 | | Not available. | |

TABLE 10

|   | C | G | I | J | K |
|---|---|---|---|---|---|
| IgG (µg/ml) | 1084 ± 45 | 310 ± 8 | 940 ± 140 | 625 ± 16 | 345 ± 3 |
| Protein impurities (µg/ml) | 103 ± 16 | 13 ± 6 | 256 ± 2 | 86 ± 3 | 239 ± 16 |
| DNA (ng/ml) | 308 ± 101 | 28 ± 2 | 409 ± 76 | 206 ± 3 | 83 ± 18 |
| Yield (overall) | 70% | 22% | 60% | 96% | 99% |
| Purity | 92% | 92% | 79% | 92% | 59% |
| DNA (ppm) | 283 | 92 | 434 | 553 | 296 |

In Table 2-9, purity is calculated as IgG content by protein A chromatography and Bradford assay. As shown in Table 2-9, strategy C provided a monoclonal antibody B product with high solubility. Strategy G provided significant reduction in DNA but also a significant loss of IgG. The overall yield was between 22 and 99%. Modification of the culture supernatant (e.g, Strategies J and K) provided higher yields. SEC chromatograms are provided in FIG. 8. This data demonstrates that the highest purity and yield result from Strategy C.

6. Isolation of Monoclonal Antibodies from Monoclonal Antibody-containing Cell Culture "Supernatant C".

Five different purification strategies were evaluated to determine the optimal conditions for purifying monoclonal antibody from monoclonal antibody-containing cell culture supernatant C ("supernatant C" containing monoclonal antibody having a pI~6.8), as summarized in Table 12.

TABLE 12

| Purification strategy | Salt type | Conductivity [mS/cm] | pH | Ethanol [%(v/v)] | Temperature [° C.] | IgG [µg/ml] | Predicted solubility (Jungbauer et al. 2010c) Protein impurities [µg/ml'] | DNA [ng/ml] |
|---|---|---|---|---|---|---|---|---|
| L | $CaCl_2$ | 10 | 6.5 | 10 | -5.3 | 37231 | 29 | 181 |
|   | $CaCl_2$ | 40 | 6.5 | 20 | -10 | 190 | 253 | 1218 |

TABLE 12-continued

| Purification strategy | Salt type | Conductivity [mS/cm] | pH | Ethanol [%(v/v)] | Temperature [° C.] | IgG [µg/ml] | Predicted solubility (Jungbauer et al. 2010c) Protein impurities [µg/ml'] | DNA [ng/ml] |
|---|---|---|---|---|---|---|---|---|
| M | CaCl$_2$ | 10 | 7.5 | 5 | −2.4 | 6902 | 59 | 158 |
|  | CaCl$_2$ | 20 | 7.5 | 40 | −2.4 | 46 | 292 | 380 |
| N | NaCl | 40 | 6.5 | 15 | −5.3 | 292 | 1557 | 976 |
| O | No modification |  |  | 15 | −5.3 |  | Not available |  |
| P | 1:4 diluted |  |  | 15 | −5.3 |  | Not available. |  |

The first two precipitation strategies focus again on initial precipitation of the impurities, followed by precipitation of the antibody. Strategy "L" can be performed at low pH (6.5) while strategy "M" at medium pH (7.5). Strategy "N" aims again at the selective precipitation of the antibody whereas the protein impurities and DNA are kept in solution. Again, reference purification strategies using unmodified and diluted supernatant, "O" and "P", were performed. For strategy "L" an initial precipitation was observed after the first precipitation step. This fraction is given in Table 13 as "L Precipitate 1" whereas "L Precipitate 2" refers to the second precipitation observed.

TABLE 13

|  | L Precipitate 1 | L Precipitate 2 | M | N | O | P |
|---|---|---|---|---|---|---|
| IgG [µg/ml] | 1274 ± 56 | 67 ± 12 | 728 ± 4 | 394 ± 23 | 1095 ± 6 | 333 ± 49 |
| Protein impurities [µg/ml] | 531 ± 191 | 1 ± 17 | 251 ± 218 | 10 ± 102 | 482 ± 80 | 33 ± 54 |
| DNA[ng/ml] | 4880 ± 2026 | 34 ± 11 | 516 ± 51 | 219 ± 7 | 765 ± 9 | 227 ± 50 |
| Yield (stepoverall) | 81% | 16% | 46% | 25% | 65% | 77% |
| Purity | 71% | 99% | 74% | 98% | 69% | 91% |
| DNA [ppm] | 3830 | 507 | 709 | 556 | 699 | 682 |

The calculated yield (81%), almost all IgG, was found in this first fraction. However, DNA removal as well as protein impurity removal was insufficient. Again this unexpected precipitation could be due to changes in the pH upon temperature change. Insufficient DNA precipitation may be due to insufficient phosphate in the supernatant. It can be assumed that the DNA precipitation mechanism is based on a calcium-phosphate precipitation. Strategy "L" could be improved upon addition of phosphate and simultaneous decrease of ethanol addition and increase of temperature. Strategy "M" also resulted in high levels of DNA, probably due to the lack of phosphate, but also in low yield and low purity. Further temperature decrease might increase the efficiency of the antibody precipitation. The use of less ethanol may also increase purity. Surprisingly strategy "N", where the antibody is selectively precipitated, provided good purity and DNA removal. However, yield was less than satisfactory (25%). Further decrease of temperature and/or increase of ethanol concentration may improve the yield. The best result was obtained with strategy "P" which used the diluted supernatant: purity was around 90% and yield around 77% (e.g., high yield). Furthermore, in the purifications described in Table 15, an improved method for precipitate recovery was used: the pre-cooling of syringes and filters. This resulted in even higher yield and purity (99%, and 99% respectively for strategy P). This strategy employed a total of a 1:8 dilution of the supernatant. Considering the SEC chromatograms of the precipitates of the different precipitation strategies, the large molecular weight fraction could not be removed by ethanol precipitation. This may be due to the incomplete DNA precipitation caused by the low phosphate concentration in the supernatant, or these may be antibody aggregates. Calcium was determined to be less efficient in the removal of DNA from supernatant C than supernatant A or B. Further addition of phosphate may assist with DNA removal.

The modified Strategy C (conductivity of 29 mS/cm) was also tested on supernatant C (Table 14). It was not expected that Strategy C would provide a sufficiently pure "C" preparation considering the predicted low solubility thereof. One would have predicted that DNA would co-precipitate and the monoclonal antibody yield would be low. Table 15 provides an overview of the composition of the various dissolved pellets. As shown therein, despite the addition of phosphate prior to calcium chloride, DNA removal was not complete.

TABLE 14

| Purification strategy | Salt type | Conductivity [mS/cm] | pH | Ethanol [%(v/v)] | Temperature [° C.] | IgG [µg/ml] | Predicted solubility (Jungbauer et al. 2010c) Protein impurities [µg/ml'] | DNA [ng/ml] |
|---|---|---|---|---|---|---|---|---|
| C | CaCl$_2$ | 29 | 8.5 | 0 | 4.0 | 35932 | 88 | 4809.4 |
|  | CaCl$_2$ | 29 | 6.5 | 25 | −10 | 330.1 | 112.2 | 425.9 |
| L | CaCl$_2$ | 10 | 6.5 | 10 | −5.3 | 37231 | 29 | 181 |
|  | CaCl$_2$ | 40 | 6.5 | 20 | −10 | 190 | 253 | 1218 |

TABLE 14-continued

| Purification strategy | Salt type | Conductivity [mS/cm] | pH | Ethanol [%(v/v)] | Temperature [° C.] | IgG [µg/ml] | Predicted solubility (Jungbauer et al. 2010c) Protein impurities [µg/ml'] | DNA [ng/ml] |
|---|---|---|---|---|---|---|---|---|
| M | CaCl$_2$ | 10 | 7.5 | 5 | −2.4 | 6902 | 59 | 158 |
|   | CaCl$_2$ | 20 | 7.5 | 40 | −2.4 | 46 | 292 | 380 |
| N | NaCl | 40 | 6.5 | 15 | −5.3 | 292 | 1557 | 976 |
| O | No modification | | | 15 | −5.3 | | Not available | |
| P | 1:4 diluted | | | 15 | −5.3 | | Not available. | |

TABLE 15

|  | C | L | M | N | P | O |
|---|---|---|---|---|---|---|
| IgG [µg/ml] | 931 ± 207 | 801 ± 53 | 1074 ± 68 | 385 ± 55 | 1098 ± 233 | 500 ± 87 |
| Protein impurities [µg/ml] | 27 ± 77 | 8 ± 34 | 10 ± 43 | 6 ± 13 | 10 ± 17 | 26 ± 82 |
| DNA [ng/ml] | 577 ± 116 | 2908 ± 1340 | 538 ± 49 | 939 ± 269 | 790 ± 134 | 3024 ± 604 |
| Yield (overall) | 92% | 60% | 60% | 24% | 99% | 95% |
| Purity | 96% | 99% | 99% | 99% | 99% | 99% |
| DNA [ppm] | 623 | 3637 | 443 | 2470 | 760 | 6296 |

Based on the results presented in Table 2-13 and FIGS. 2-7B, strategies C and P (1:4 dilution of supernatant in H$_2$O followed by the addition of 15% (v/v) ethanol) are optimal. According to the SEC data, Strategy M may provide the highest purity but the yield provided by Strategy C is significantly higher.

7. Further Modified Strategy C (Addition of Phosphate)

Figure 10:
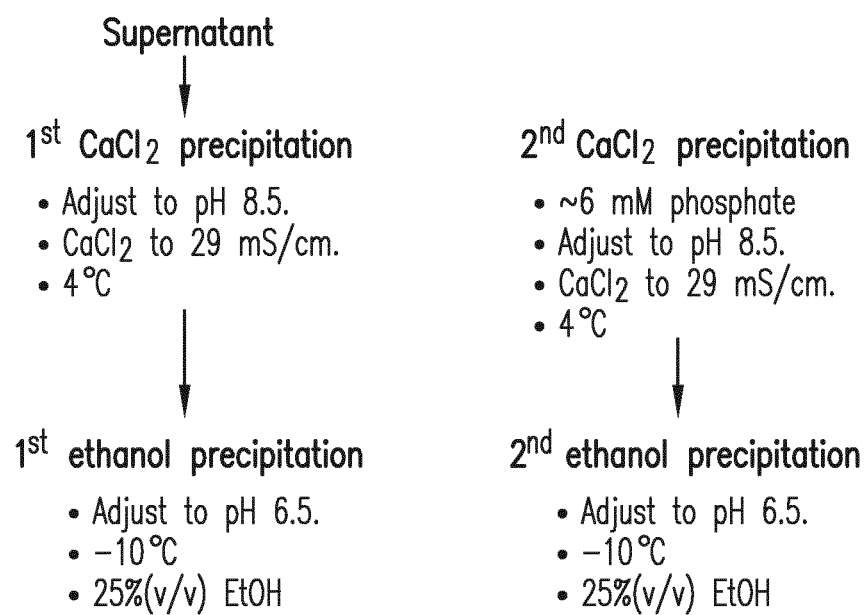
FIG. 10. Second exemplary method.
Figure 11A:
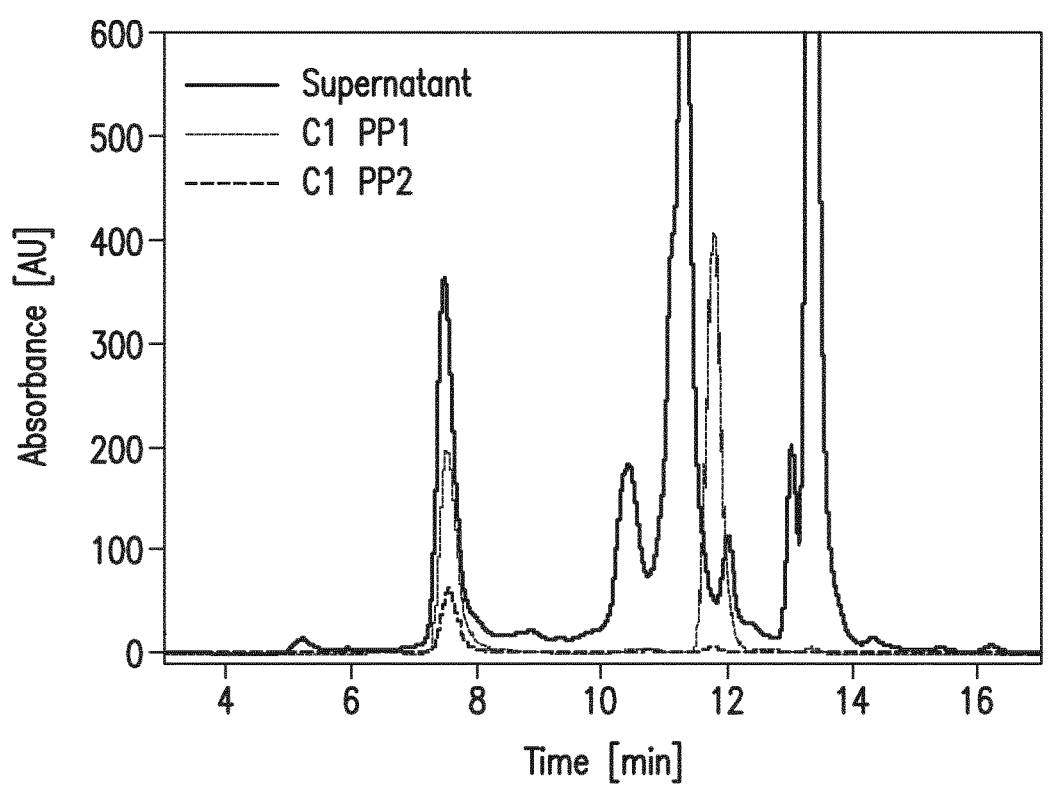
FIG. 11. Exemplary results.
Figure 11B:
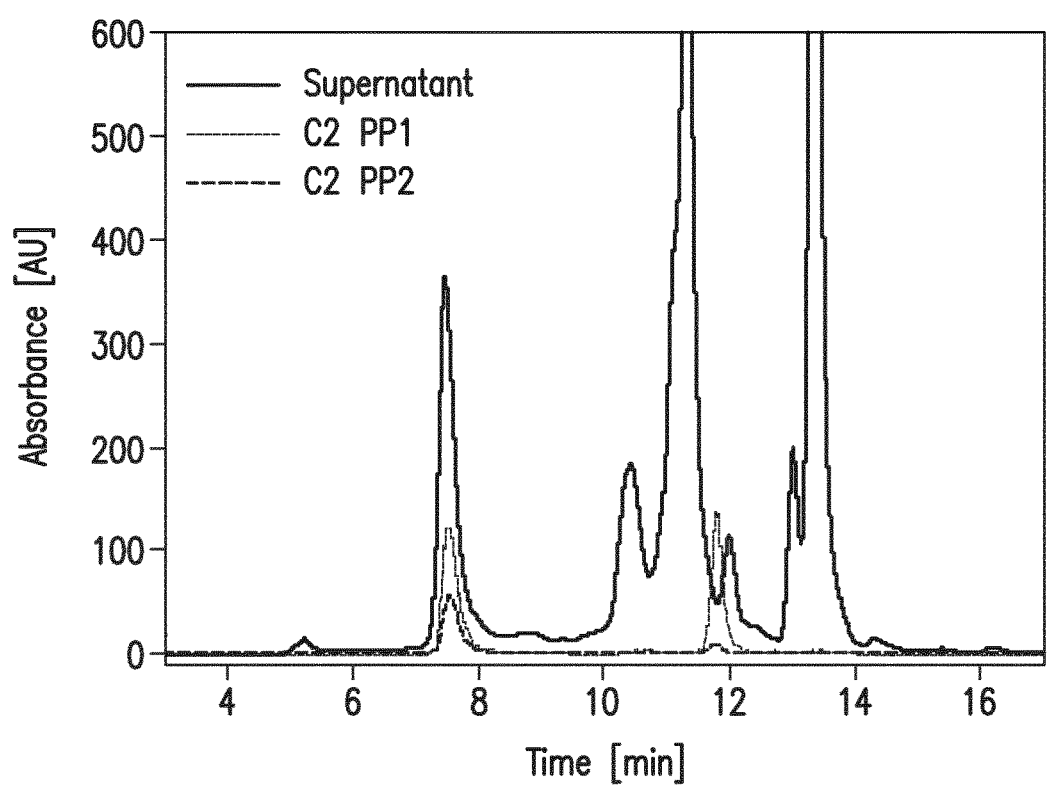
Figure 11C:
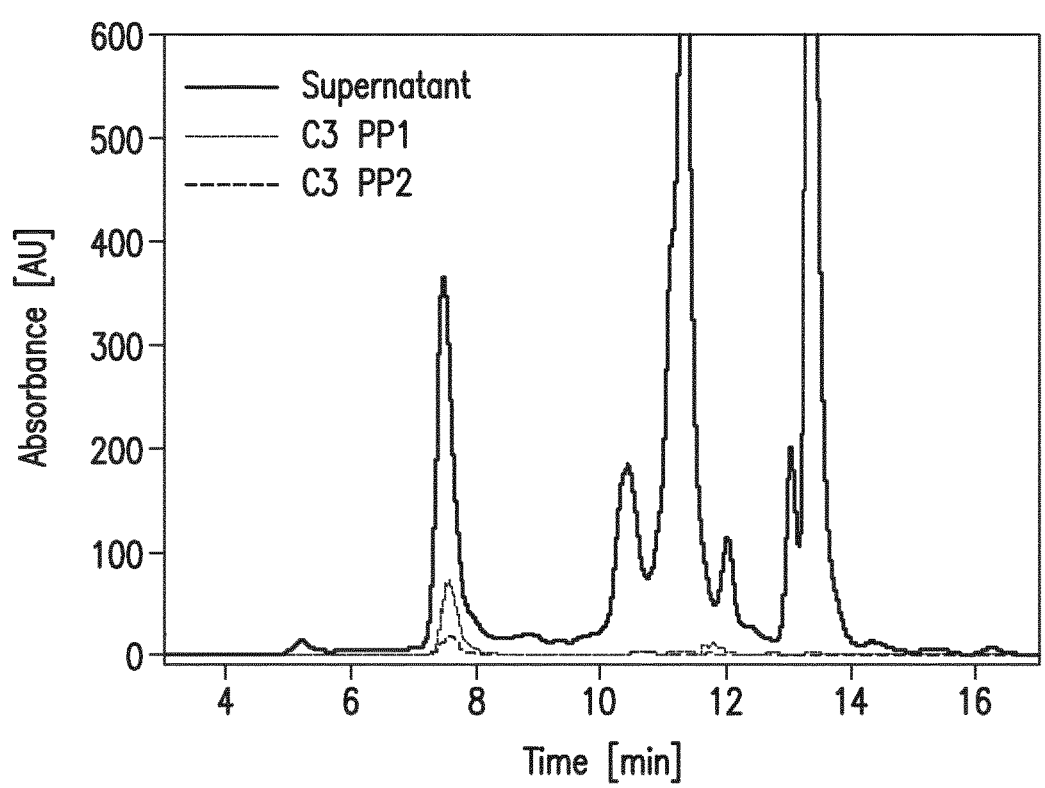
Figure 11D:
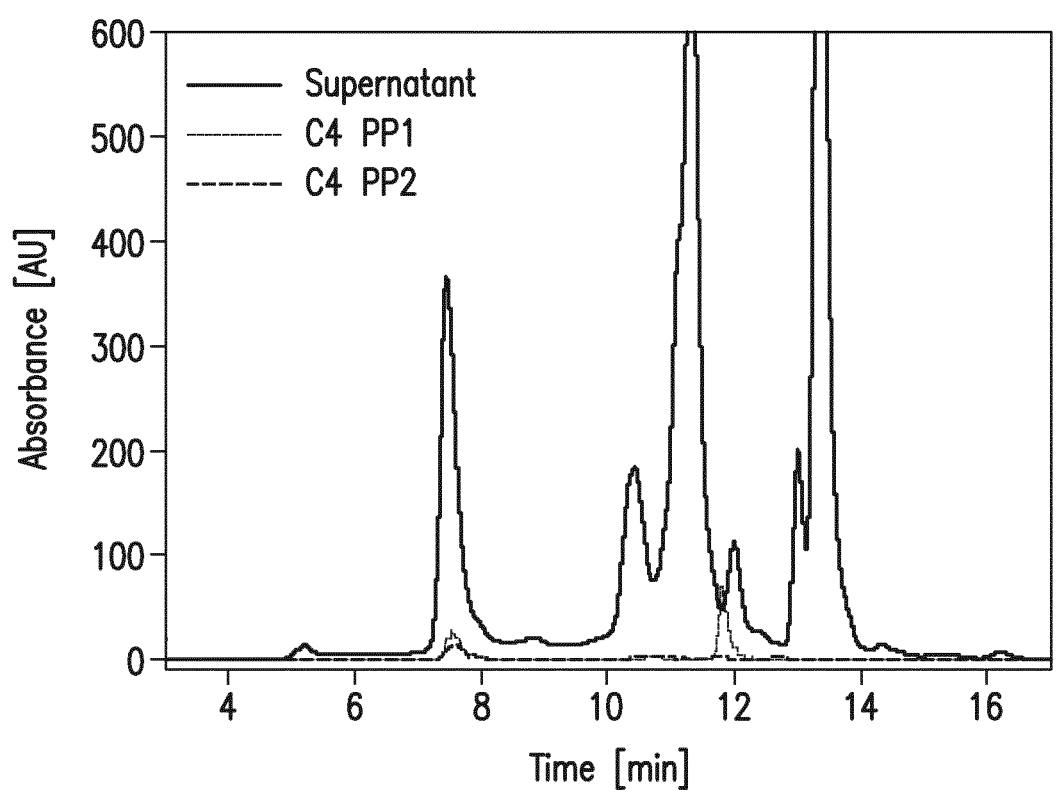

Supernatants A, B and C were separately evaluated using a modified strategy involving the addition of phosphate. The method included an initial CaCl$_2$ precipitation followed by a first ethanol precipitation. The pellet from the first ethanol precipitation was then dissolved in 20 mM histidine, 100 mM NaCl, pH 6.5. Sodium phosphate was then added to a final concentration of 4 mM to assist in the second CaCl$_2$ precipitation. All experiments were performed in quadruplets and the precipitates recovered by centrifugation. This purification procedure is illustrated in FIG. 10.

Figure 12A:
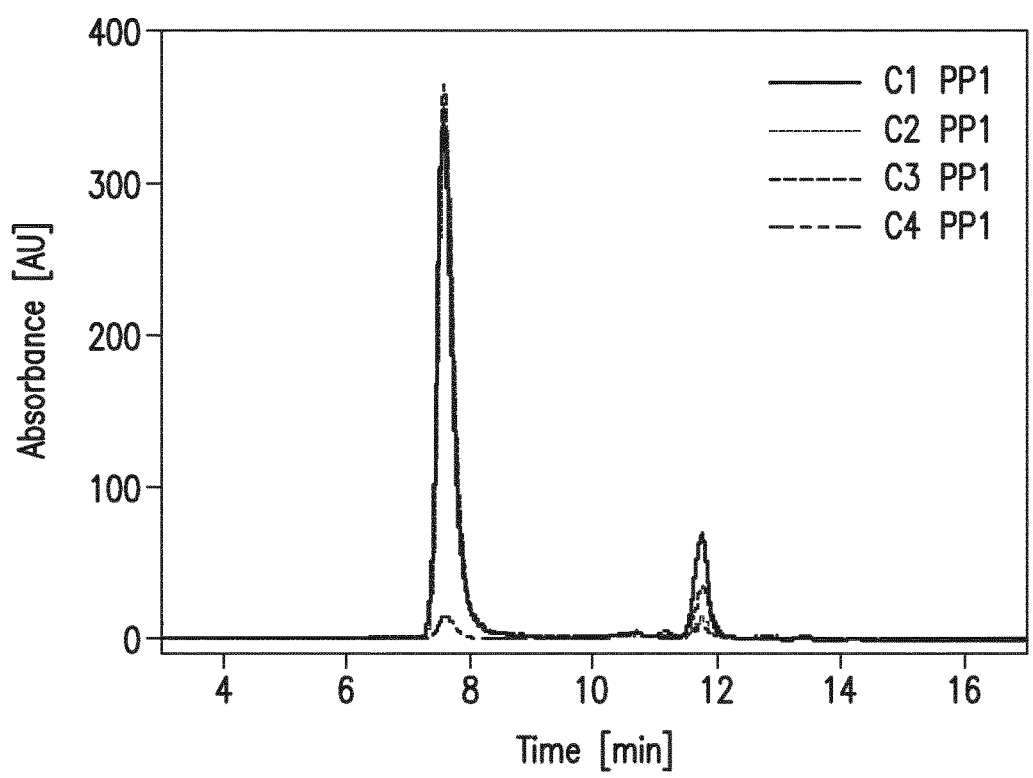
FIG. 12. Purified samples.
Figure 12B:
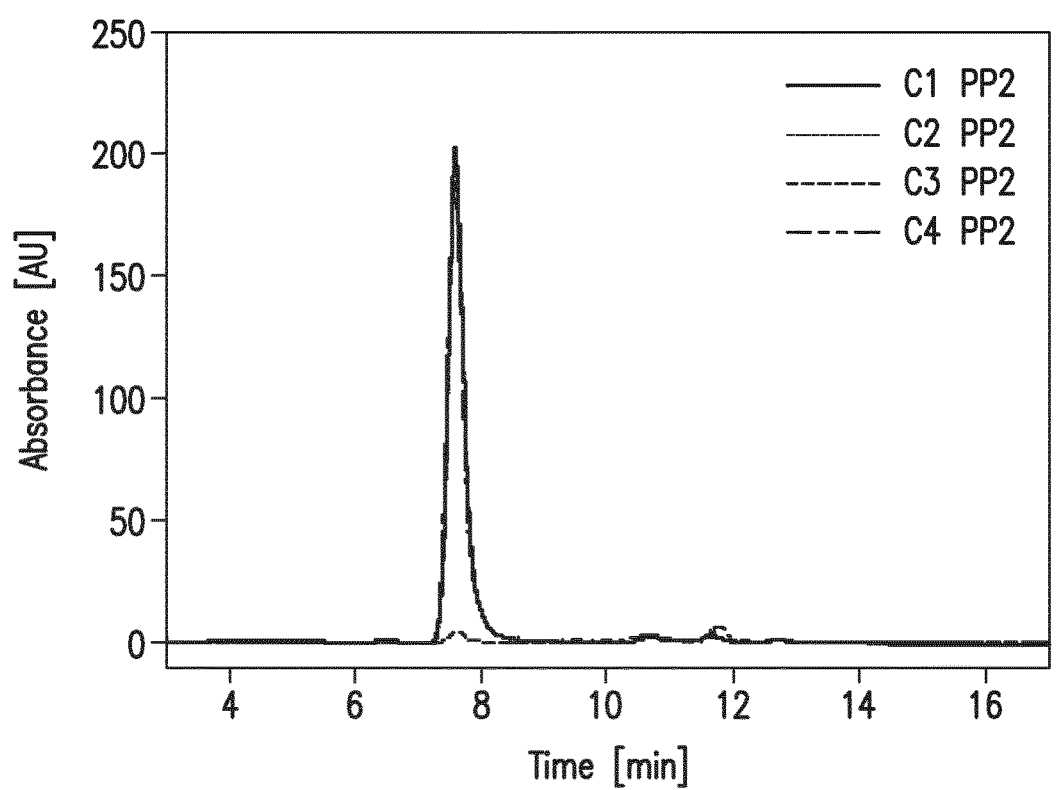
Figure 13A:
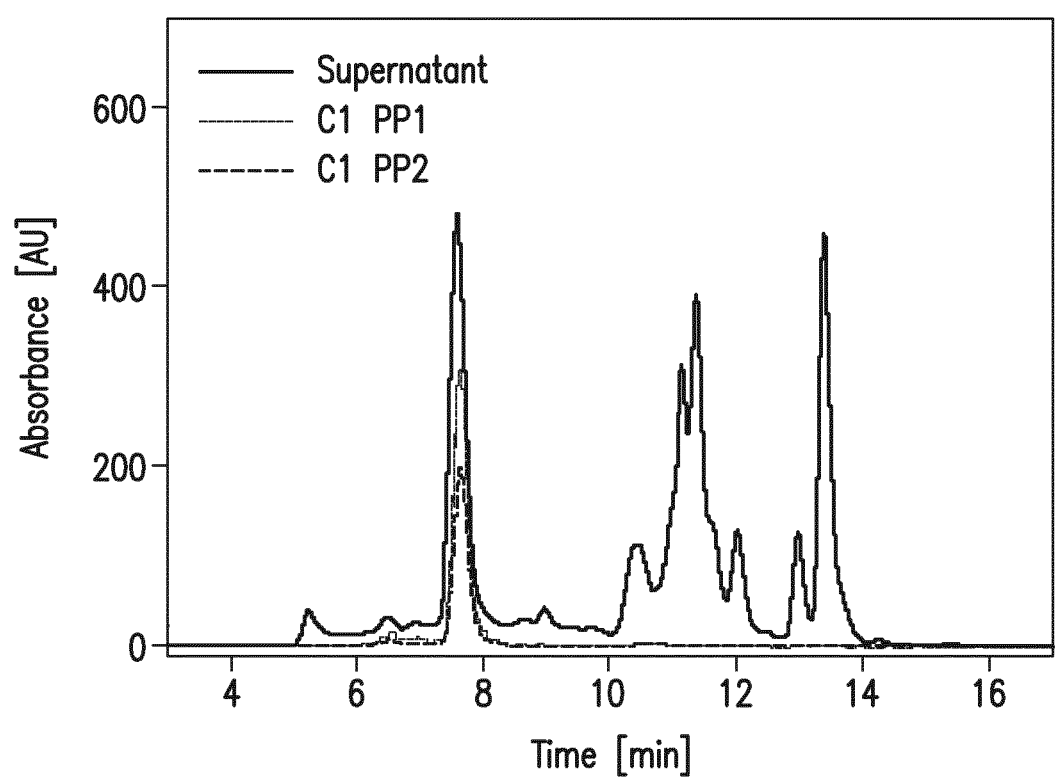
FIG. 13. Additional purified samples.
Figure 13B:
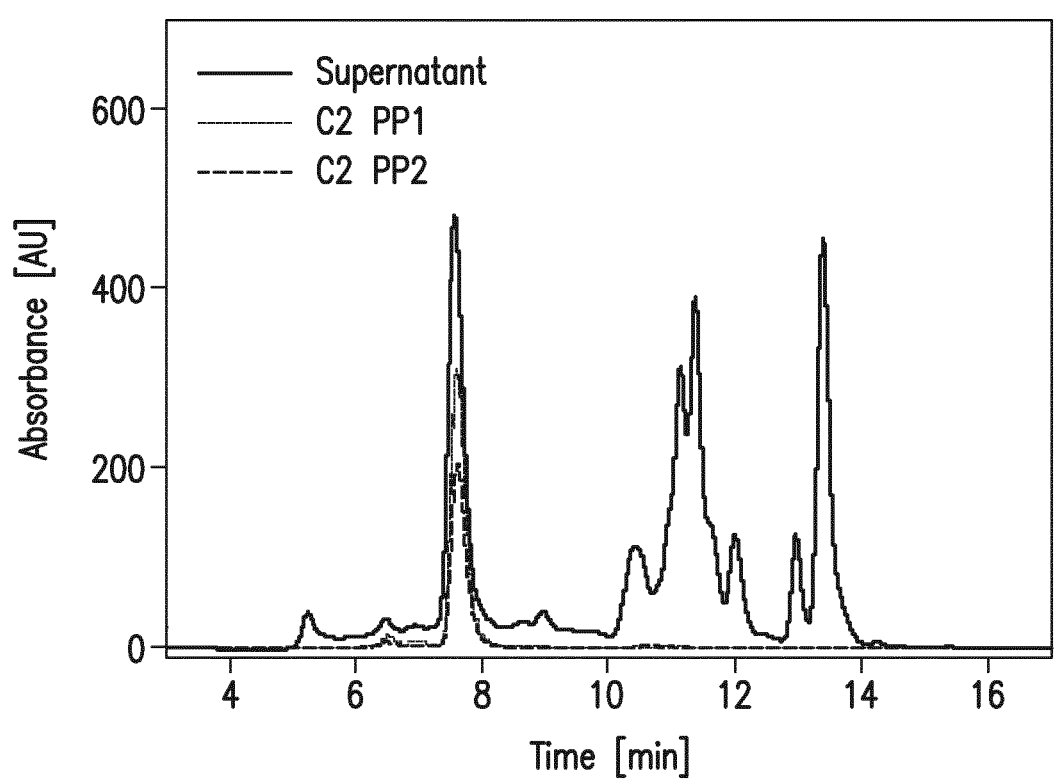
Figure 13C:
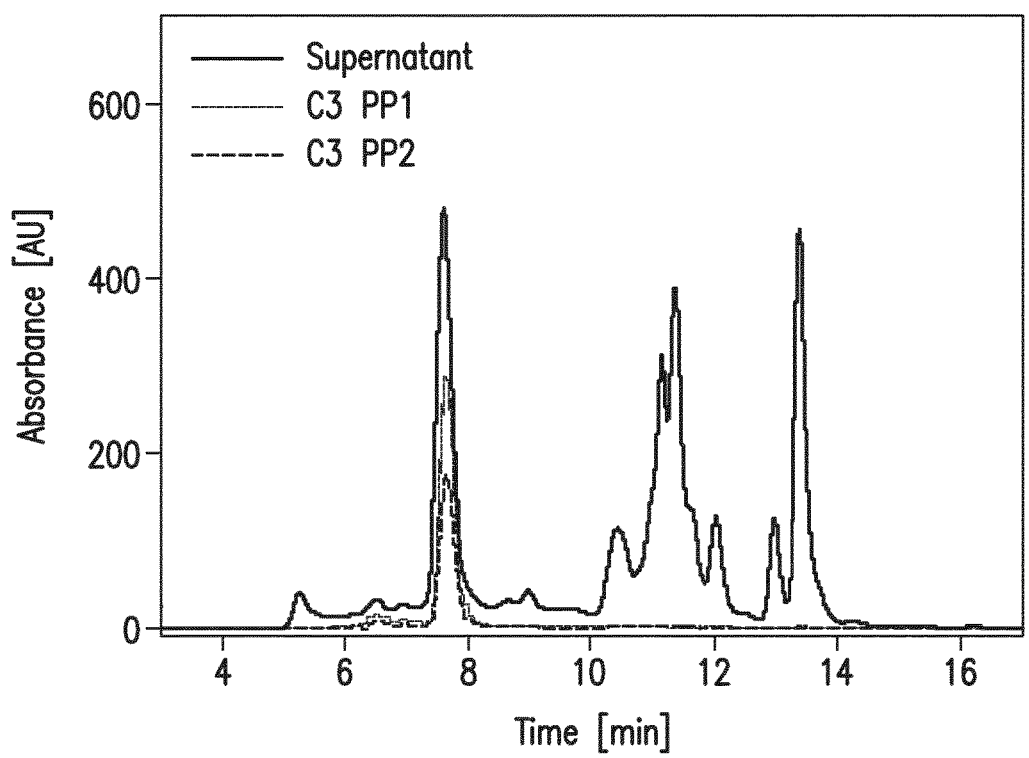
Figure 13D:
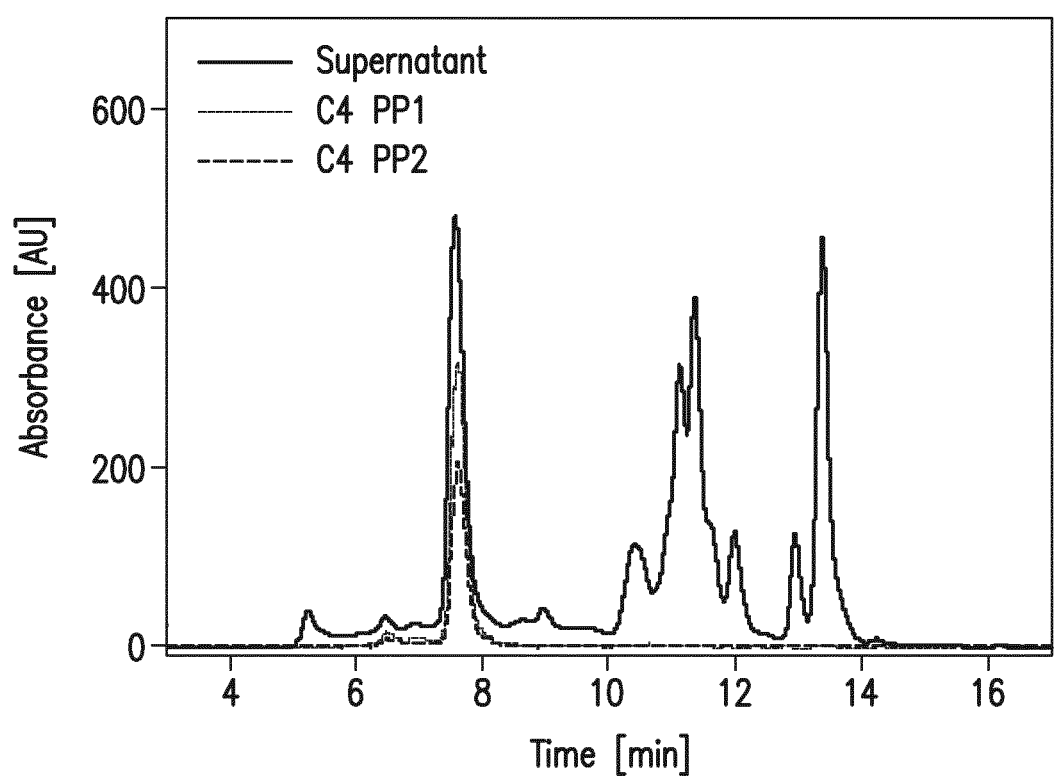

Table 16 provides the mass balance for the small-scale purification of IgG from supernatant B using this further modified strategy C. The required purity (100-fold HCP reduction) is achieved after the second ethanol precipitation. However, additional precipitation steps resulted in a significant loss of IgG over the course of the purification. Each step provided a yield of 64-77%, resulting in an overall yield of 26%. This is evident from the SEC chromatograms (FIG. 11; note: "C3" results not represented in Table 16). SEC chromatograms for the ethanol and CaCl$_2$ precipitates were compared. As shown in FIG. 12, the impurities eluting at about 12 minutes in the precipitates of step 1 are removed in the precipitates of step 2 (except C3).

TABLE 16

|  | IgG (µg/ml) | HCP (ppm) | DNA (ppm) | Purity | Yield (step/overall) | HCP reduction factor |
|---|---|---|---|---|---|---|
| Supernatant | 1383 | 44792 | 752 | 12% | | |
| 1$^{st}$ CaCl$_2$ precipitation | 1020 | ND | ND | 14% | 75%/75% | |
| 1$^{st}$ ethanol precipitation | 680 | 4505 | 83 | >90% | 77%/58% | 9.9 |
| 2$^{nd}$ CaCl$_2$ precipitation | 531 | ND | ND | >90% | 71%/41% | |
| 2$^{nd}$ ethanol precipitation | 250 | 289 | 149 | >95% | 64%/26% | 155 |

Figure 14A:
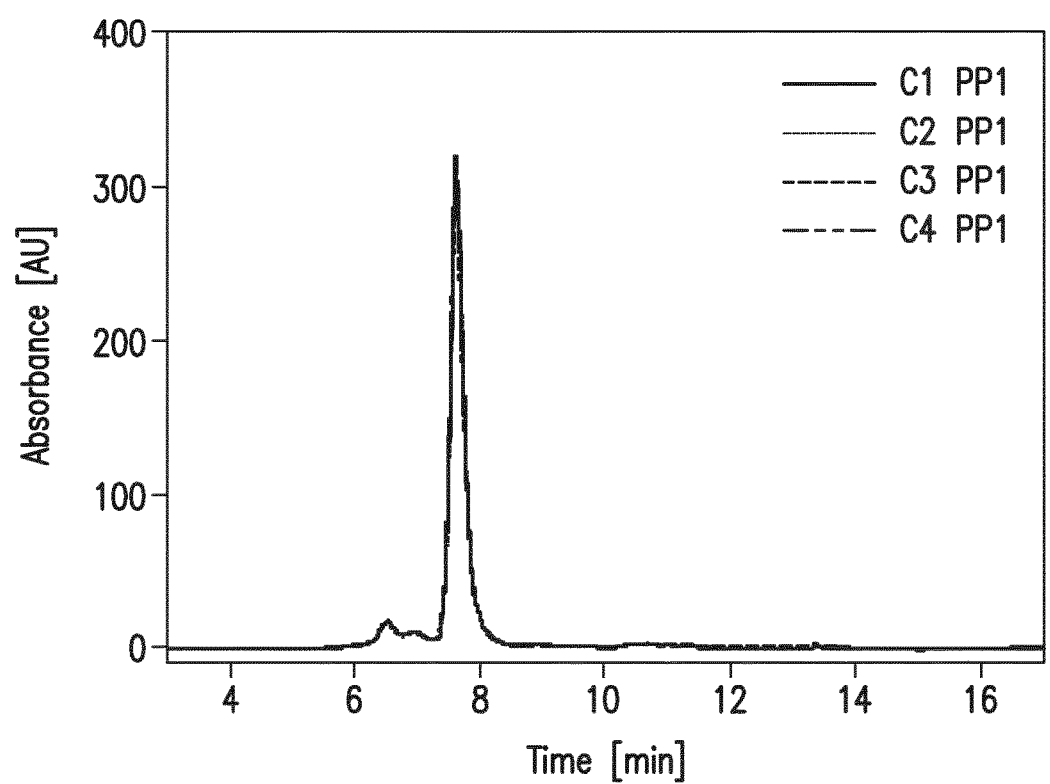
FIG. 14. Purified samples.
Figure 14B:
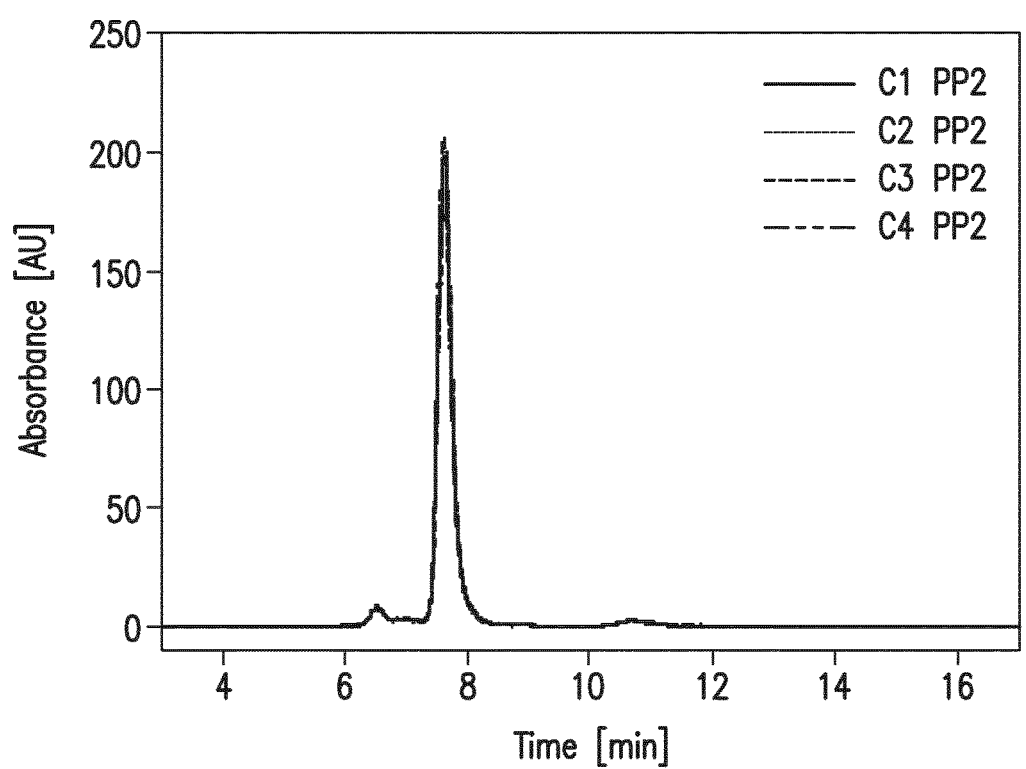

This process was also used to purify antibody from supernatant C. The results are summarized in Table 17. The overall HCP reduction was about 80-fold. Recovery data is presented in FIG. 13. As shown in FIG. 14, the impurities eluting at about 12 minutes (e.g., typically between about ten to 12 minutes) in the precipitates of step 1 are removed in the precipitates of step 2 (except C3).

TABLE 17

|  | IgG (µg/ml) | HCP (ppm) | DNA (ppm) | Purity | Yield (step/overall) | HCP reduction factor |
|---|---|---|---|---|---|---|
| Supernatant | 1825 | 145561 | 9161 | ~25% | | |
| 1$^{st}$ CaCl$_2$ precipitation | 1573 | ND | ND | 24% | 88%/88% | |
| 1$^{st}$ ethanol precipitation | 1196 | 17201 | 126 | >90% | 81%/71% | 8.5 |
| 2$^{nd}$ CaCl$_2$ precipitation | 820 | ND | ND | >90% | 92%/65% | |
| 2$^{nd}$ ethanol precipitation | 703 | 1732 | 204 | >95% | 87%/57% | 84 |

Mass balance data resulting from purification of monoclonal antibody from supernatant A, B, C, or D using modified strategy C (FIG. 17) is presented in Tables 18, 19, 20, and 21:

TABLE 18

|  | IgG [µg/ml] | HCP [ppm] | DNA [ppm] | Purity | Yield (step/overall) | HCP reduction factor |
|---|---|---|---|---|---|---|
| Supernatant | 1508 | 32949 | 642 | 29% | | |
| 1$^{st}$ CaCl$_2$ precipitation | 1400 | n.d. | n.d. | 29% | 94%/94% | |

TABLE 18-continued

| | IgG [µg/ml] | HCP [ppm] | DNA [ppm] | Purity | Yield (step/overall) | HCP reduction factor |
|---|---|---|---|---|---|---|
| 1st Ethanol precipitation | 817 | 4000 | 131 | >90% | 77%/72% | 10 |
| 2nd CaCl₂ precipitation | 306 | n.d. | n.d. | >90% | 78%/56% | |
| 2nd Ethanol precipitation | 209 | 752 | 54 | >90% | 33%/18% | 43 |

TABLE 19

| | IgG [µg/ml] | HCP [ppm] | DNA [ppm] | Purity | Yield (step/overall) | HCP reduction factor |
|---|---|---|---|---|---|---|
| Supernatant | 789 | 174538 | 3335 | ~12% | | |
| 1st CaCl2 precipitation | 534 | n.d. | n.d. | 11% | 95%/95% | |
| 1st Ethanol precipitation | 394 | 53345 | 492 | >90% | 69%/66% | 3 |
| 2nd CaCl₂ precipitation | 297 | n.d. | n.d. | >90% | 79%/52% | |
| 2nd Ethanol precipitation | 170 | 1825 | 302 | >95% | 58%/30% | 95 |

TABLE 20

| | IgG [µg/ml] | HCP [ppm] | DNA [ppm] | Purity | Yield (step/overall) | HCP reduction factor |
|---|---|---|---|---|---|---|
| Supernatant | 1997 | 386702 | 22131 | ~23% | | |
| 1st CaCl₂ precipitation | 1960 | n.d. | n.d. | 26% | 95%/95% | |
| 1st Ethanol precipitation | 1265 | 256657 | 739 | >90% | 98%/93% | 3 |
| 2nd CaCl₂ precipitation | 1128 | n.d. | n.d. | >90% | 93%/86% | |
| 2nd Ethanol precipitation | 899 | 5362 | 398 | >99% | 80%/67% | 72 |

TABLE 21

| | IgG [µg/ml] | HCP [ppm] | DNA [ppm] | Purity | Yield (step/overall) | HCP reduction factor |
|---|---|---|---|---|---|---|
| Supernatant | 2948 | 90755 | 217 | ~30% | | |
| 1st CaCl₂ precipitation | 2544 | n.d. | n.d. | 29% | 86%/86% | |
| 1st Ethanol precipitation | 1593 | 122503 | 101 | >90% | 84%/72% | 1 |
| 2nd CaCl₂ precipitation | 1345 | n.d. | n.d. | >90% | 86%/62% | |
| 2nd Ethanol precipitation | 998 | 8254 | 36 | >95% | 74%/46% | 11 |

8. Large-scale Isolation Procedures

Figure 18A:
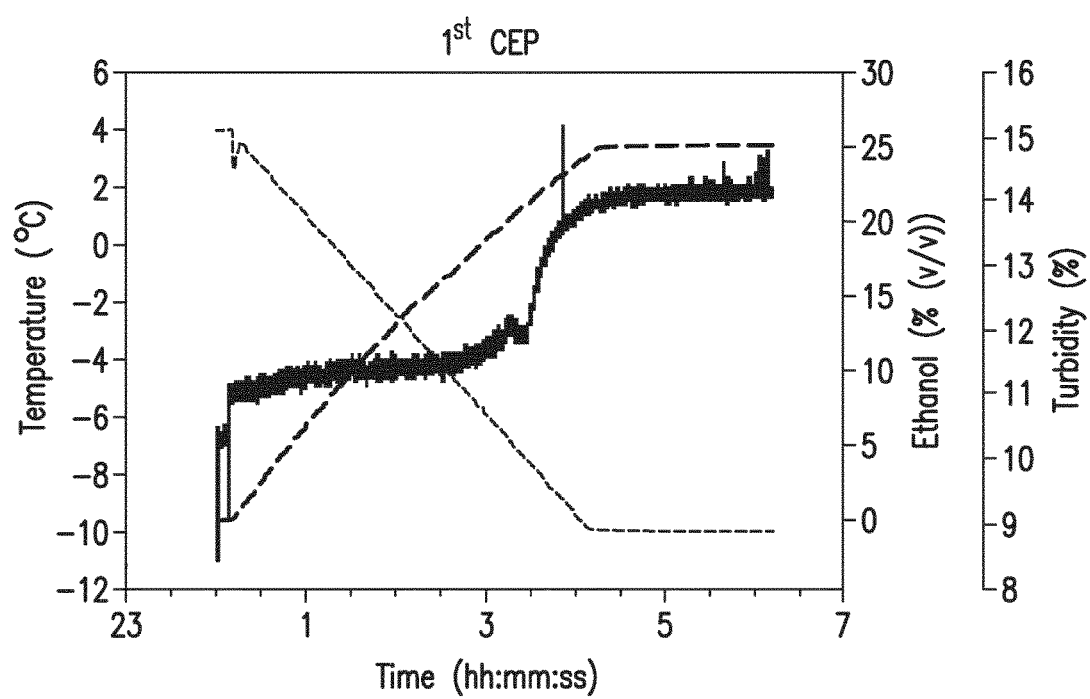
FIG. 18. A. First cold ethanol precipitation. B. Second cold ethanol precipitation.
Figure 18B:
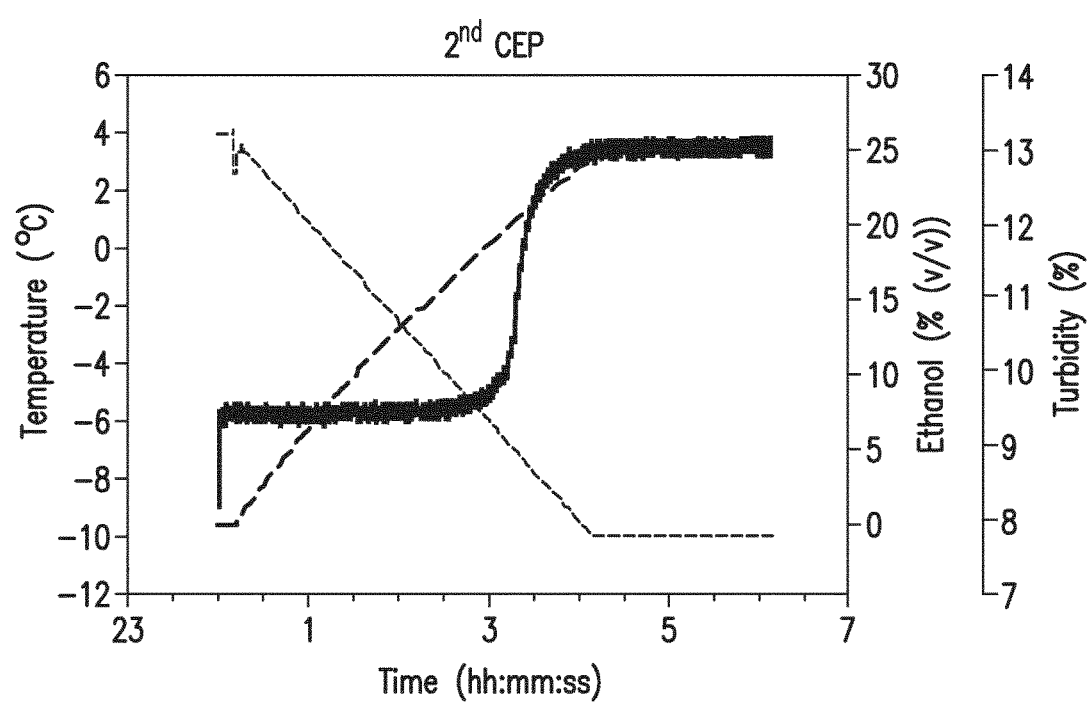
Figure 19A:
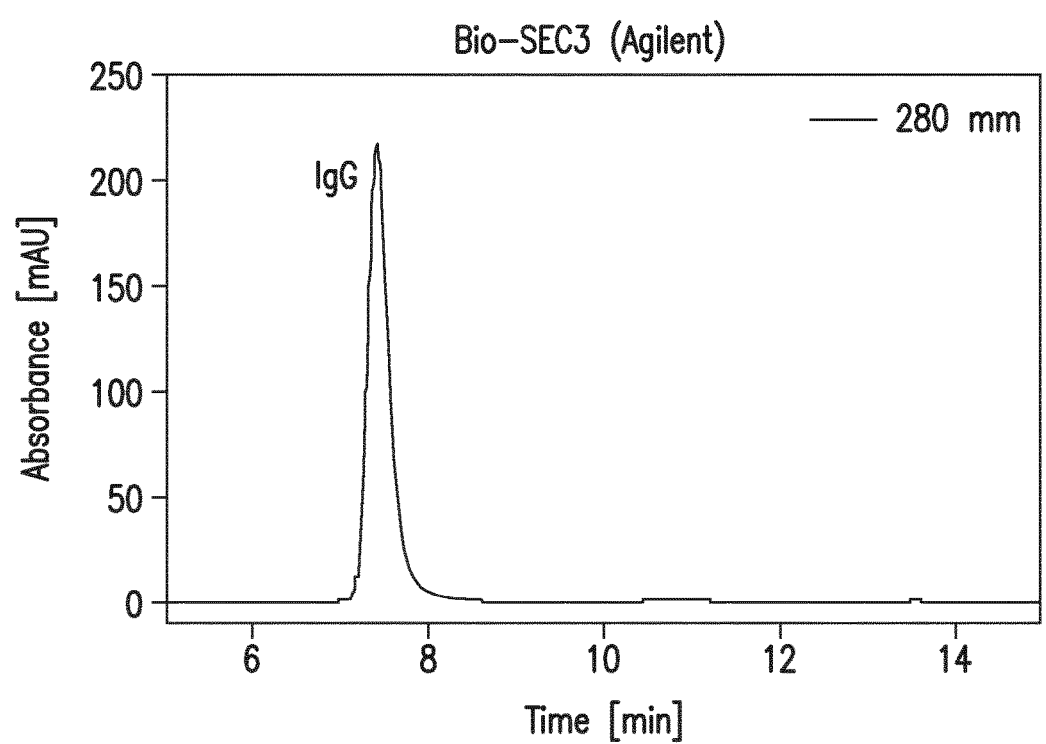
FIG. 19. A. Isolated antibody (Bio-SEC3). B. Isolated antibody (TSK G3000Wx1).
Figure 19B:
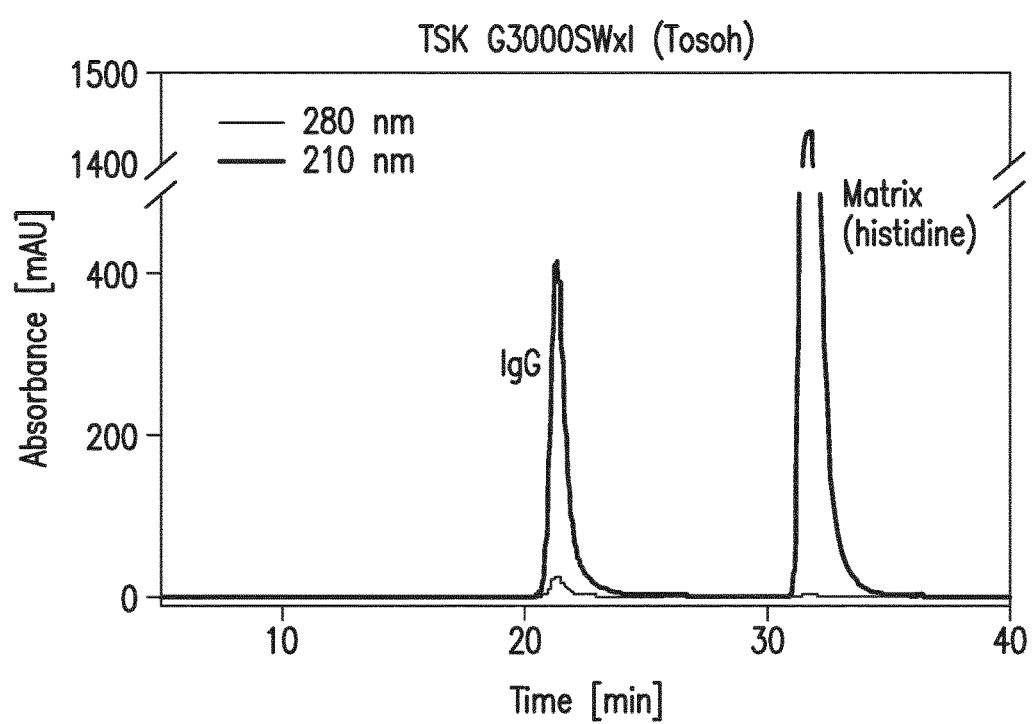

In some smaller scale embodiments, the use of 50 mM CaCl₂ for the CaCl₂ precipitation step provided a yield of only about 18% and a HCP reduction of only about 43-fold. At higher CaCl₂ concentrations (added up to 29 mS/cm), significantly higher HCP reduction (159-fold) and yield (26%) were observed. In the large-scale isolation procedures described here, 250 mM CaCl₂ (~50 mS/cm) was selected as providing high HCP reduction and good yield. The CEP step was maintained at −10° C., 2 h, and 25% (v/v) ethanol. The CaCl₂ precipitation was performed at room temperature using a beaker and a magnetic stirrer. For adjustment of pH, CaCl₂ and phosphate concentrations a 25% HCl, 10.0 M NaOH, 5.0 M CaCl₂ and a 0.3 M N₂HPO₄ solution were used. For CEP, the solutions were transferred to an EasyMax reactor. FIG. 18 describes the temperature profile, the IR probe response, and the ethanol concentration of the first (A) and second (B) CEP precipitation in the EasyMax reactor. Ethanol was added over 4 h while simultaneously decreasing the temperature from 4° C. to −10° C. where it was then kept for 2 h to reach precipitation equilibrium. As shown in FIG. 18, the first and second CEP precipitation begins at about three hours (−6° C., >20% (v/v) ethanol). The turbidity reaches quickly its equilibrium, suggesting that the precipitation is a rather fast reaction. During the purification, samples were drawn after each precipitation step and analysed by analytical protein A chromatography, SEC, and CHO HCP ELISA (Table 22). As shown therein, the yield increased to 64% and a high HCP reduction (83-fold) was observed. As shown in FIG. 19, the final dissolved precipitate is of high purity and the IgG obtained is highly monomeric.

Figure 20A:
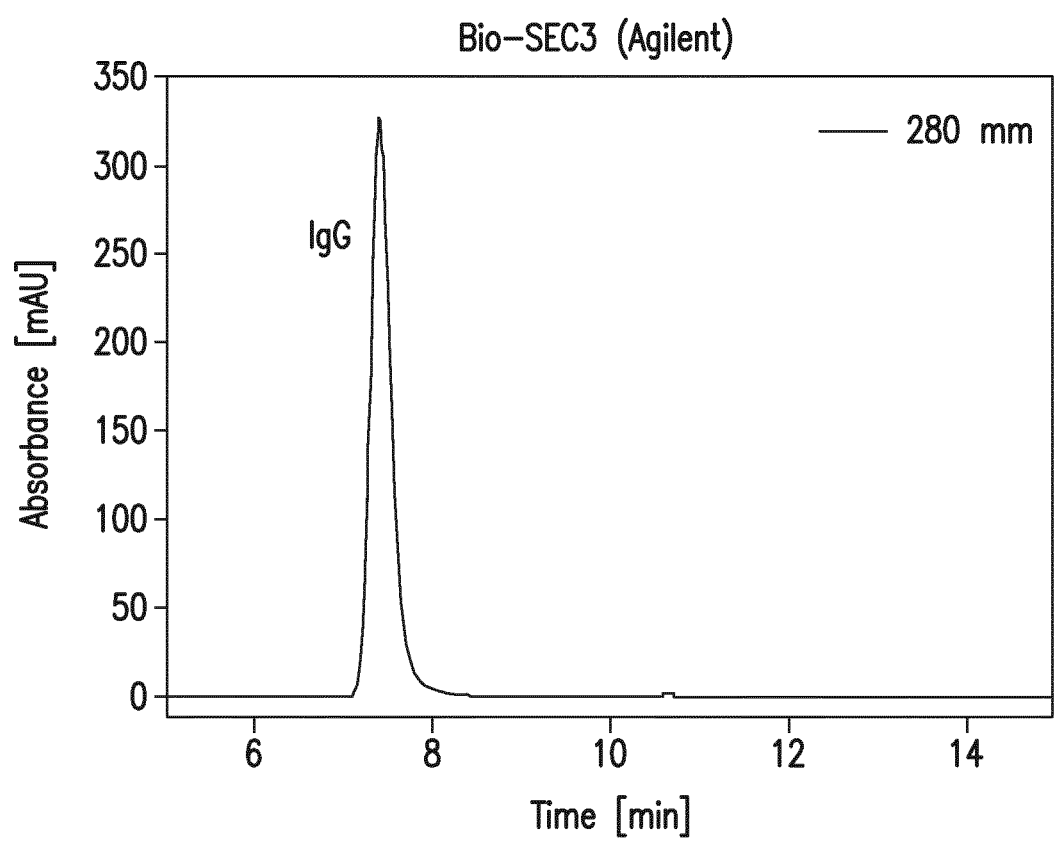
FIG. 20. A. Isolated antibody (Bio-SEC3). B. Isolated antibody (TSK G3000Wx1).
Figure 20B:
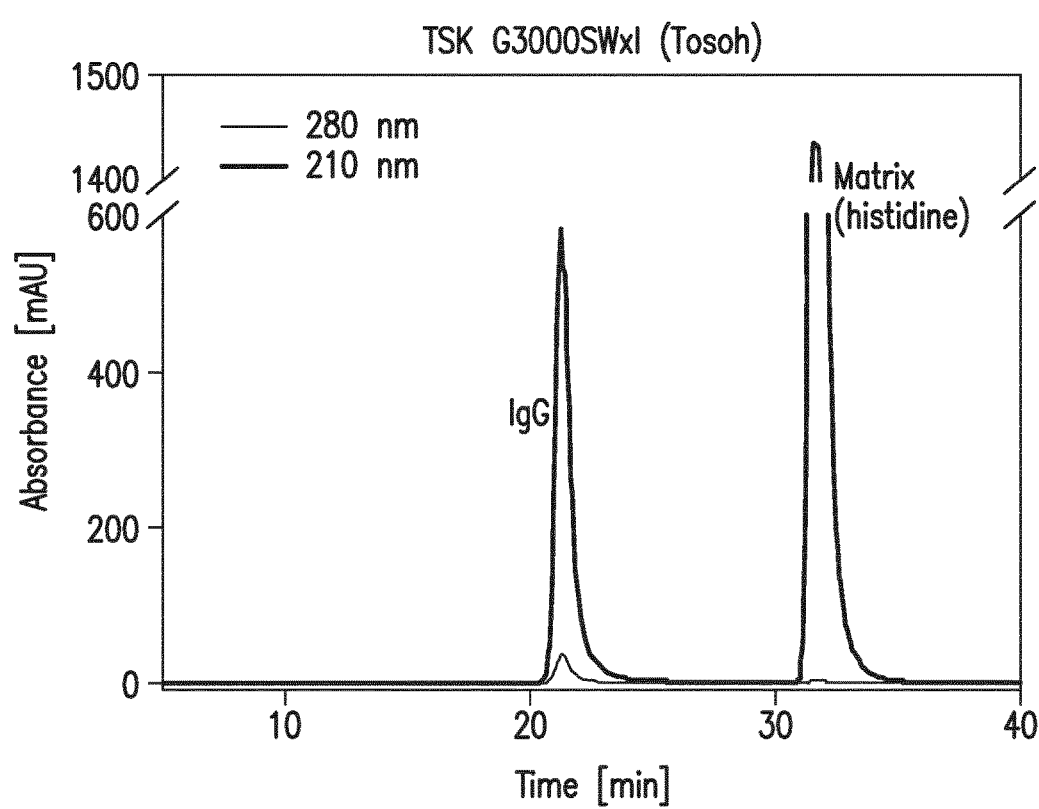
Figure 21A:
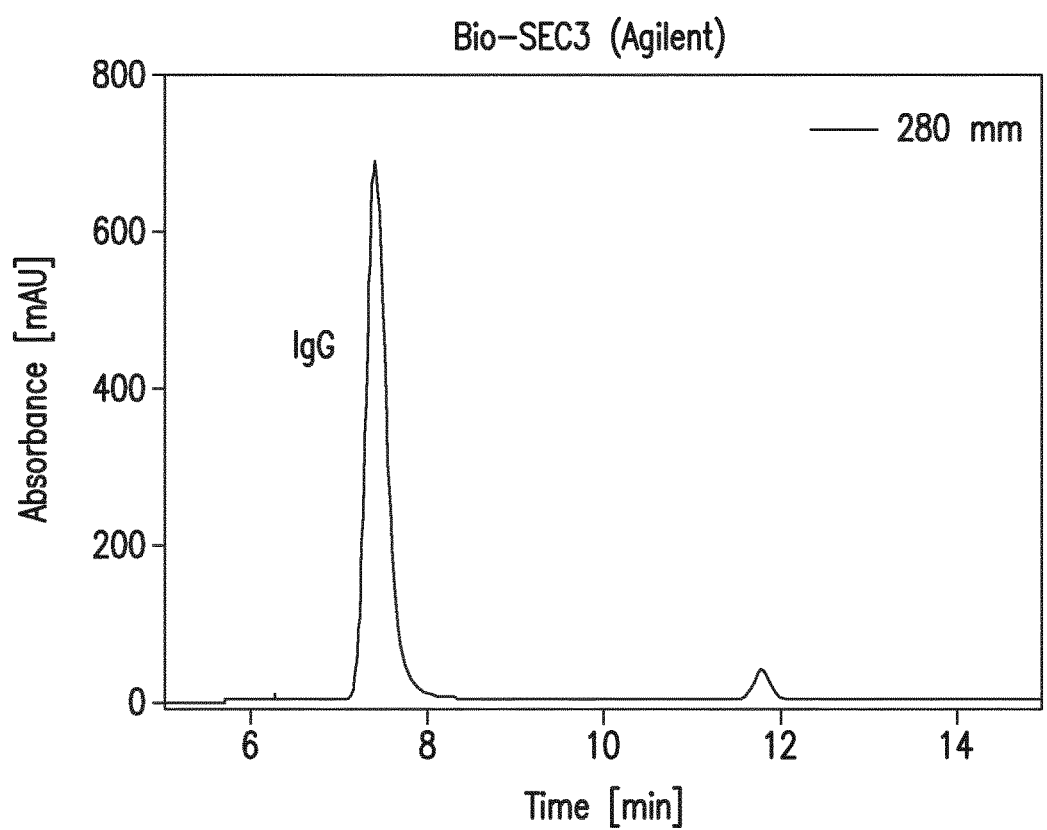
FIG. 21. A. Isolated antibody (Bio-SEC3). B. Isolated antibody (TSK G3000Wx1).
Figure 21B:
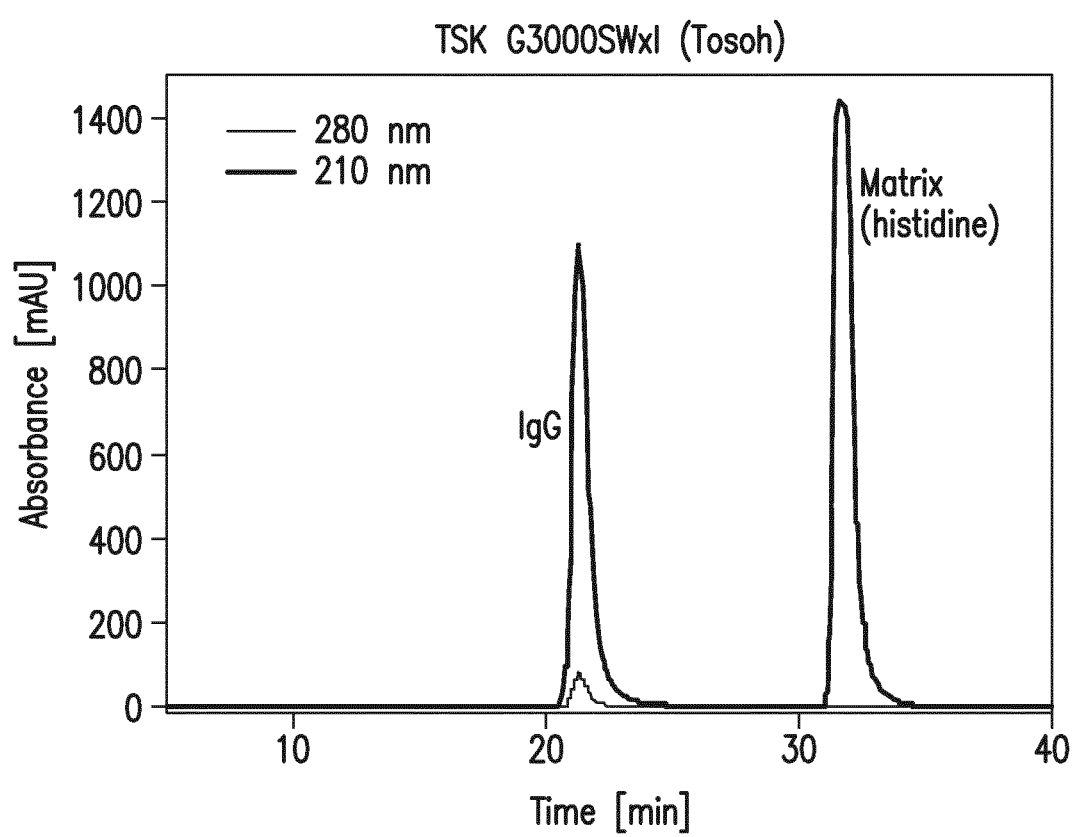

In another embodiment, the precipitate was isolated after the second CaCl₂ precipitation using a syringe filter (Whatman, 0.2 µm) instead of centrifugation. The samples were drawn after each precipitation step and analysed by analytical protein A chromatography, SEC and CHO HCP ELISA (Table 23). As shown therein, yield increased to 71% and HCP reduction remained high (128-fold). However, due to the longer exposure to room temperature, the precipitate collected by filtration (2$^{nd}$ CEP) partially dissolved and the soluble IgG fraction found in the supernatant was higher (167 mg/l) than expected (64 mg/l) resulting in a lower step yield for the 2$^{nd}$ CEP (84%) than for the 1$^{st}$ CEP (94%). Assuming a similar concentration of the soluble fraction of the 2$^{nd}$ CEP as for the 1$^{st}$ CEP, the step yield as well as the overall yield would have been higher (step yield ~95%; overall yield ~80.5%). As seen in FIG. 20, the final dissolved precipitate is of high purity and the IgG obtained is highly monomeric. This procedure was repeated with another supernatant sample and similar results were observed (91-fold HCP reduction; Table 24, FIG. 21). As shown in FIG. 21, the resulting precipitate is of high purity and the IgG obtained is highly monomeric.

Figure 22A:
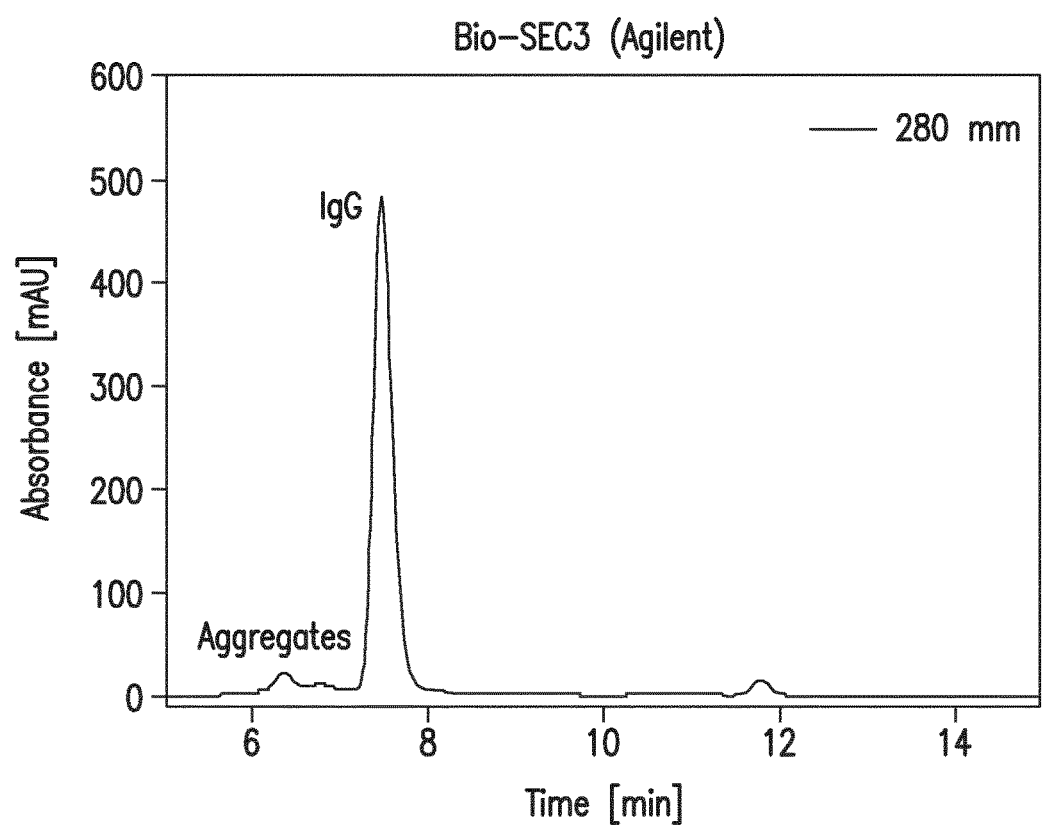
FIG. 22. A. Isolated antibody (Bio-SEC3). B. Isolated antibody (TSK G3000Wx1).
Figure 22B:
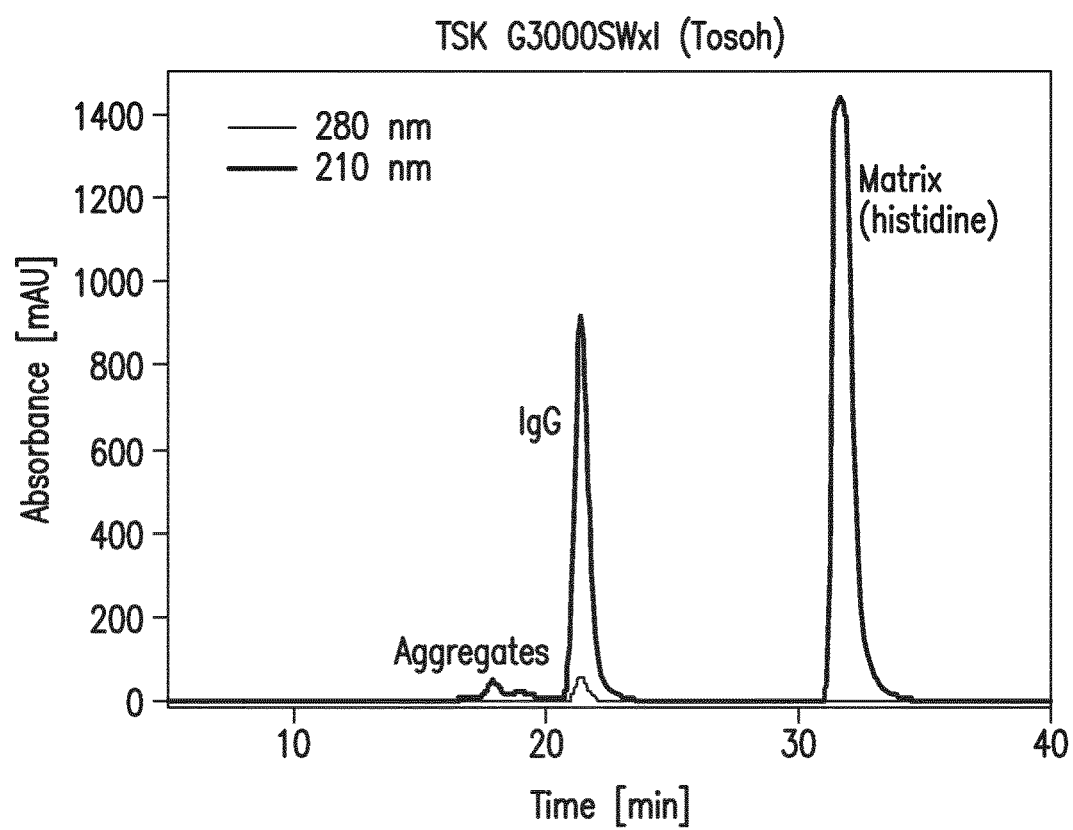

This procedure was also carried out using supernatant C (Table 25). As shown therein, the yield increased to 91% but the HCP reduction was only 23-fold. As can also be seen in FIG. 22, the final dissolved precipitate is of high purity but contained a larger amount of IgG aggregates.

Figure 23:
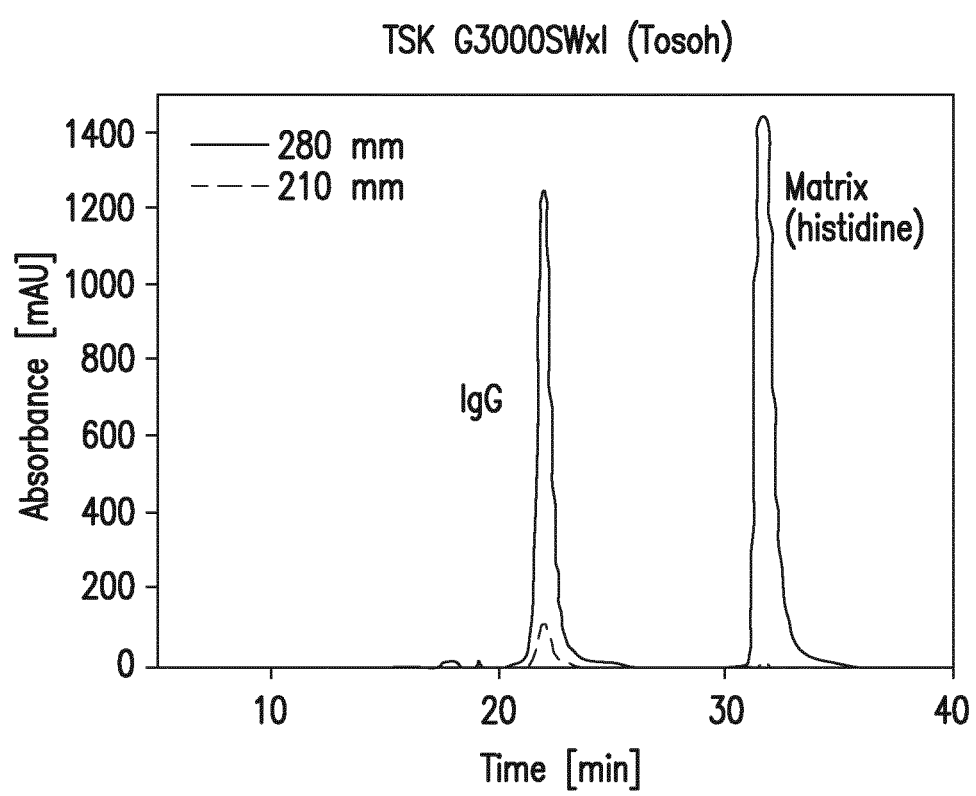
FIG. 23. A. Isolated antibody (TSK G3000Wx1)
FIG. 24. Influence of stirring velocity, washing, and temperature/syringe temperature on yield.

This procedure was also carried out on Supernatant D. The precipitation was performed as previously and the samples drawn after each precipitation step analysed by analytical protein A chromatography, SEC and CHO HCP ELISA (Table 26). The yield increased to 76% but the HCP reduction was only 48-fold. As shown in FIG. 23, the final dissolved precipitate is high purity IgG.

TABLE 22

Purification of monoclonal antibody from supernatant A at large scale (70 ml) using the EasyMax reactor

| | Dilution factor | IgG [µg/ml] | IgG yield step | IgG yield overall | Monomer * | Monomer ** | Purity * | Purity ** | HCP [ppm] | HCP Reduction step | HCP Reduction overall |
|---|---|---|---|---|---|---|---|---|---|---|---|
| Supernatant | 1.00 | 1222 | | | | | | | 54212 | 0 | 0 |
| 1st CaCl₂ supernatant | 1.12 | 1029 | 94% | 94% | | | | | 44641 | 1.2 | 1.2 |
| 1st CEP precipitate | 1.00 | 874 | 85% | 80% | | | | | 6922 | 6.5 | 7.8 |
| 2nd CaCl₂ supernatant | 1.07 | 684 | 86% | 69% | | | | | 3157 | 2.3 | 17.2 |
| 2nd CEP precipitate | 1.00 | 636 | 93% | 64% | >99.9% | >99.9% | >99.9% | 95.3% | 650 | 4.9 | 83.4 |

TABLE 23

Purification of monoclonal antibody from supernatant A at large scale (70 ml) using the EasyMax reactor

| | Dilution factor | IgG [µg/ml] | IgG yield step | IgG yield overall | Monomer * | Monomer ** | Purity * | Purity ** | HCP [ppm] | HCP Reduction step | HCP Reduction overall |
|---|---|---|---|---|---|---|---|---|---|---|---|
| Supernatant | 1.00 | 1521 | | | | | | | 135336 | 0 | 0 |
| 1st CaCl₂ supernatant | 1.10 | 1379 | 99% | 99% | | | | | 69877 | 1.8 | 1.8 |
| 1st CEP precipitate | 1.00 | 1249 | 91% | 90% | | | | | 15829 | 4 | 7.1 |
| 2nd CaCl₂ supernatant | 1.07 | 1065 | 94% | 95% | | | | | 2615 | 4.7 | 36.2 |
| 2nd CEP precipitate | 1.00 | 894 | 84% | 71% | >99.9% | 99.9% | >99.9% | 96.0% | 620 | 3.5 | 128.3 |

TABLE 24

Purification of monoclonal antibody from supernatant A at large scale (70 ml) using the EasyMax reactor

| | Dilution factor | IgG [µg/ml] | IgG yield step | IgG yield overall | Monomer * | Monomer ** | Purity * | Purity ** | HCP [ppm] | HCP Reduction step | HCP Reduction overall |
|---|---|---|---|---|---|---|---|---|---|---|---|
| Supernatant | 1.00 | 2563.4 | | | | | | | 109231 | | |
| 1st CaCl₂ supernatant | 1.00 | 2379.4 | 98.0% | 98.0% | | | | | 26773 | 4.1 | 4.1 |
| 1st CEP precipitate | 1.13 | 2172.4 | 91.3% | 89.3% | | 98.7% | | 88.4% | 15224 | 1.8 | 7.2 |
| 2nd CaCl₂ supernatant | 1.00 | 1991.7 | 98.1% | 87.6% | | | | | 3865 | 3.9 | 28.3 |
| 2nd CEP precipitate | 1.35 | 1816.4 | 91.2% | 79.9% | 99.9% | 99.7% | 99.9% | 96.7% | 1202 | 3.2 | 90.9 |

TABLE 25

Purification of monoclonal antibody from supernatant C at large scale (70 ml) using the EasyMax reactor

| | Dilution factor | IgG [µg/ml] | IgG yield step | IgG yield overall | Monomer * | Monomer ** | Purity * | Purity ** | HCP [ppm] | HCP Reduction step | HCP Reduction overall |
|---|---|---|---|---|---|---|---|---|---|---|---|
| Supernatant | | 1953 | 0 | 0 | | | | | 180099 | | |
| 1st CaCl₂ supernatant | 1.07 | 1808 | 99% | 99% | | | | | | | |
| 1st CEP precipitate | 1.00 | 1649 | 89% | 88% | | 90.1% | | 80.1% | 86824 | 2.13 | 2.13 |
| 2nd CaCl₂ supernatant | 1.07 | 1487 | >99% | 97% | | | | | | | |

TABLE 25-continued

Purification of monoclonal antibody from supernatant C at large scale (70 ml) using the EasyMax reactor

|  | Dilution factor | IgG [μg/ml] | IgG yield step | IgG yield overall | Monomer * | Monomer ** | Purity * | Purity ** | HCP [ppm] | HCP Reduction step | HCP Reduction overall |
|---|---|---|---|---|---|---|---|---|---|---|---|
| $2^{nd}$ CEP precipitate | 1.00 | 1391 | 94% | 91% | 89.5% | 91.8% | 89.5% | 87.5% | 8276 | 9.37 | 23.16 |

TABLE 26

Purification of monoclonal antibody from supernatant D at large scale (70 ml) using the EasyMax reactor

|  | Dilution factor | IgG [μg/ml] | IgG yield step | IgG yield overall | Monomer * | Monomer ** | Purity * | Purity ** | HCP [ppm] | HCP Reduction step | HCP Reduction overall |
|---|---|---|---|---|---|---|---|---|---|---|---|
| Supernatant |  | 3322 |  |  |  |  |  |  | 81752 |  |  |
| $1^{st}$ CaCl$_2$ supernatant | 1.09 | 2826 | 92% | 92% |  |  |  |  |  |  |  |
| $1^{st}$ CEP precipitate | 1.00 | n.a. | n.a. | n.a. |  |  |  |  | n.a. | n.a. | n.a. |
| $2^{nd}$ CaCl$_2$ supernatant | 1.08 | 2337 | 89% | 82% |  |  |  |  |  |  |  |
| $2^{nd}$ CEP precipitate | 1.00 | 2162 | 93% | 76% | 99.4% | n.a. | 99.4% | n.a. | 3702 | 22.09 | 48.65 |

9. Modified Method Including a Single CaCl$_2$ Precipitation

It was concluded that the first ethanol precipitation step had the most significant impact on impurity (HPC) removal. In some cases, the first CaCl$_2$ precipitation was observed to only slightly influence impurity removal and result in significant IgG loss (e.g., 25%). A modified strategy in which the first CaCl$_2$ precipitation step was removed while the first and second ethanol precipitation steps and the second CaCl$_2$ precipitation maintained was therefore developed.

Figure 15A:
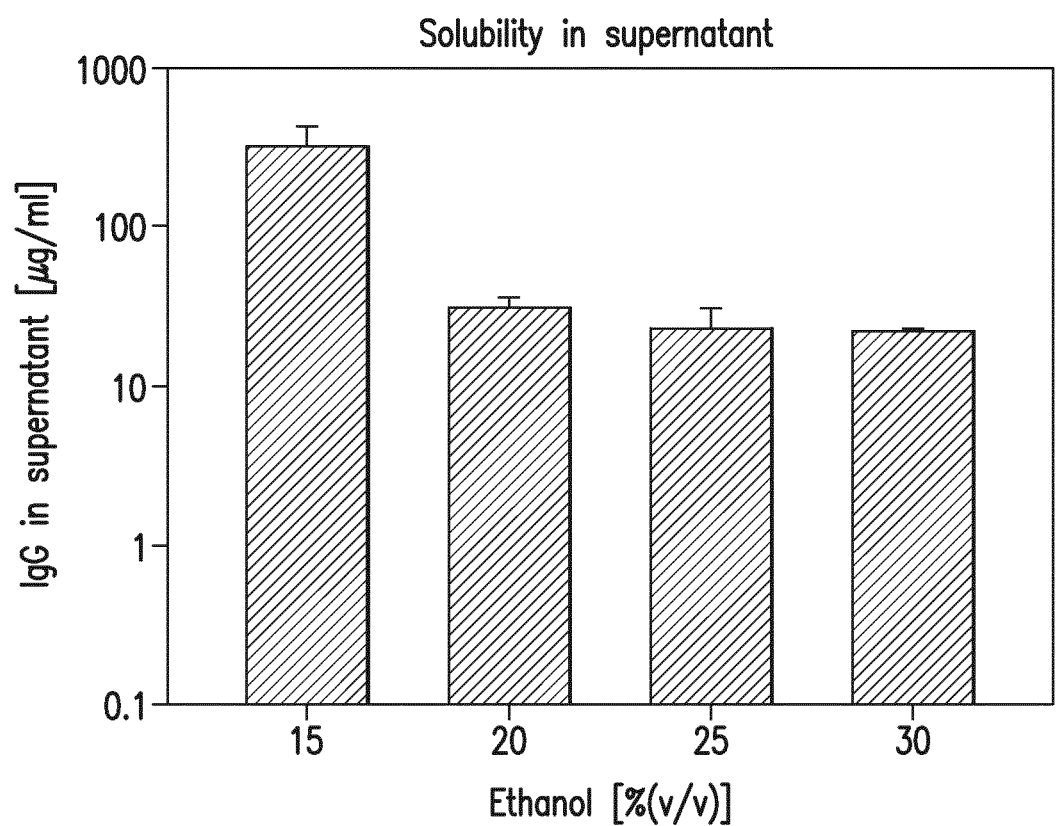
FIG. 15. Effects of ethanol concentration on solubility (A) and composition (B).
Figure 15B:
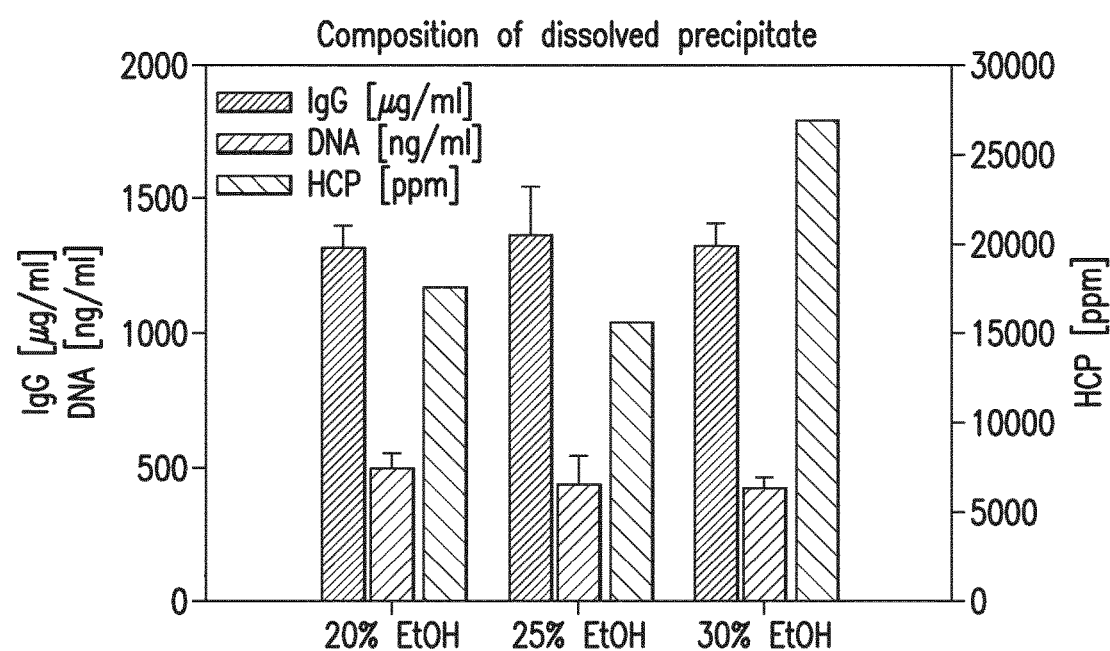
Figure 16A:
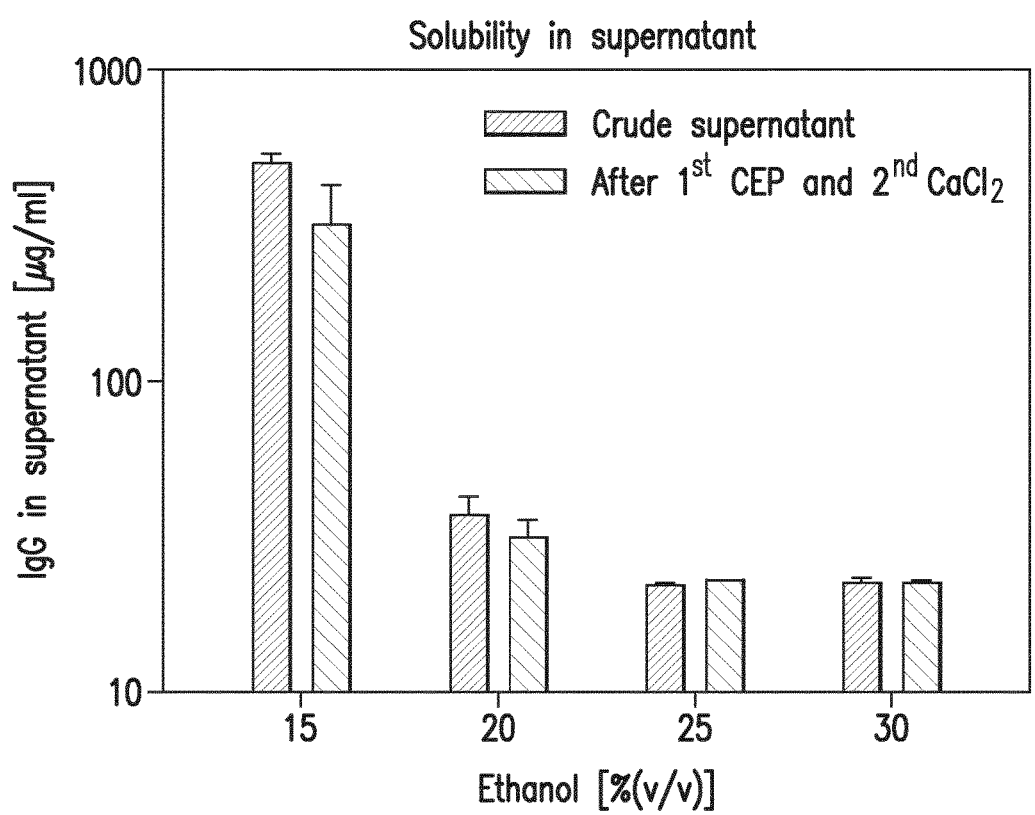
FIG. 16. Additional effects of ethanol concentration on solubility (A) and composition (B).
Figure 16B:
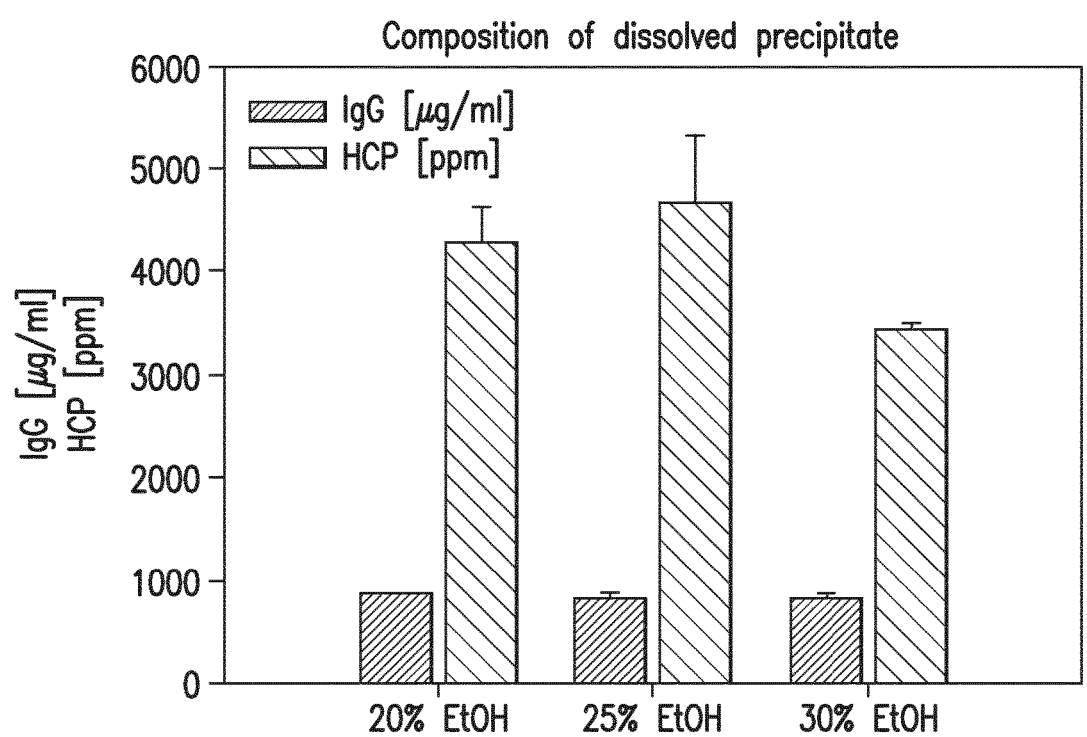

To optimize the first ethanol precipitation step, crude supernatant A was mixed with ethanol to a final ethanol concentration of 10%, 15%, 20%, 25%, or 30%. The solubility of IgG in each preparation is shown in FIG. 15(A). As shown therein, IgG is not precipitated in the presence of 10% ethanol but begins to precipitate with 15% ethanol and reaches equilibrium at 25% ethanol. FIG. 15(B) shows no difference between IgG and DNA for 20%, 25%, and 30% but a significant difference in HCP (30% ethanol significantly higher). A final concentration of 25% was therefore selected as optimal for the first ethanol precipitation step.

The effect of washing after the first ethanol precipitation step was also examined. The precipitate from ethanol precipitation was collected by centrifugation and immediately dissolved in histidine buffer (20 mM histidine, 100 mM NaCl, pH 6.0) or washed three times with 25% ethanol before being dissolved in the histidine buffer. As shown in Table 27, washing resulted in a significantly reduced yield (60%) without a significant improvement in HCP reduction (from 2.9-fold without wash to 3.6-fold with wash).

TABLE 27

|  | No wash | Wash (3-times) |
|---|---|---|
| IgG (μg/ml) | 1109 | 778 |
| Yield | 85% | 60% |
| HCP (ppm) | 12351 | 9893 |
| HCP reduction factor | 2.9 | 3.6 |

As mentioned above, the CaCl$_2$ precipitation step preceding the first ethanol precipitation step was excluded. However, the CaCl$_2$ precipitation following the first ethanol precipitation was retained and optimized as described herein. A variety of conditions were evaluated as shown in Table 28:

TABLE 28

(<q = below quantification; <d. = below detection)

| Phosphate [mM] | CaCl2 [mM] | pH | Temp [° C.] | DNA [ng/ml] | Yield [%] | Purity [%] |
|---|---|---|---|---|---|---|
| 1 | 50 | 6.5 | 4 | 881.0 | 102% | 65% |
| 1 | 50 | 6.5 | 20 | 901.7 | 103% | 66% |
| 1 | 50 | 8.5 | 4 | <q. | 100% | 69% |
| 1 | 50 | 8.5 | 20 | <q. | 101% | 70% |
| 1 | 150 | 6.5 | 4 | 374.0 | 100% | 58% |
| 1 | 150 | 6.5 | 20 | 160.5 | 100% | 57% |
| 1 | 150 | 8.5 | 4 | <d. | 98% | 59% |
| 1 | 150 | 8.5 | 20 | <d. | 99% | 60% |
| 4 | 50 | 6.5 | 4 | 53.7 | 108% | 76% |
| 4 | 50 | 6.5 | 20 | <q. | 88% | 71% |
| 4 | 50 | 8.5 | 4 | <q. | 98% | 71% |
| 4 | 50 | 8.5 | 20 | <q. | 100% | 72% |
| 4 | 150 | 6.5 | 4 | <d. | 97% | 62% |
| 4 | 150 | 6.5 | 20 | <d. | 75% | 52% |
| 4 | 150 | 8.5 | 4 | <d. | 96% | 63% |
| 4 | 150 | 8.5 | 20 | <d. | 98% | 61% |

As shown in Table 28, DNA flocculation is optimum at basic pH (pH 8.5). DNA is not detected in the remaining supernatant when 150 mM CaCl$_2$ is utilized. The yield is typically sufficiently high (96-100%). Yield was low under conditions of 20° C., pH 6.4, 4 mM phosphate (75% using 150 mM CaCl$_2$ or 88% using 50 mM CaCl$_2$). The optimal conditions for this step were determined to be 20° C., pH 8.5, 4 mM phosphate, 50 mM CaCl$_2$ because DNA was below quantifiable levels and both yield and purity were high.

The second ethanol precipitation step, which followed the first ethanol precipitation step (−10° C., 25% ethanol) and CaCl$_2$ precipitation steps (20° C., pH 8.5, 4 mM phosphate, 50 mM CaCl$_2$) described above, was also optimized. Ethanol was added to a final concentration of 10%, 15%, 20%, 25%, or 30%. After incubation for two hours at −10° C., the precipitate was collected by centrifugation and dissolved in histidine buffer (20 mM histidine, 100 mM NaCl, pH 6.0). The soluble and precipitated fractions were then analyzed, as presented in FIG. 2-7I. As shown therein, no significant difference between these conditions was observed. Twenty-five percent ethanol was therefore selected as optimal.

The HCP concentration in the dissolved pellet resulting from this modified method was significantly higher than that produced by the original method (e.g., FIGS. 1, 10). While the presence of CaCl$_2$ appeared not to influence HCP concentration, the presence of CaCl$_2$ improved HCP removal in the subsequent ethanol precipitation (Table 29).

TABLE 29

|  | Original method | No wash | Wash (3-times) |
|---|---|---|---|
| Supernatant A | 36071 | 36071 | 36071 |
| 1$^{st}$ CaCl$_2$ precipitation | 32863 |  |  |
| 1$^{st}$ ethanol precipitation | 2530 | 12351 | 9893 |

Figure 17:
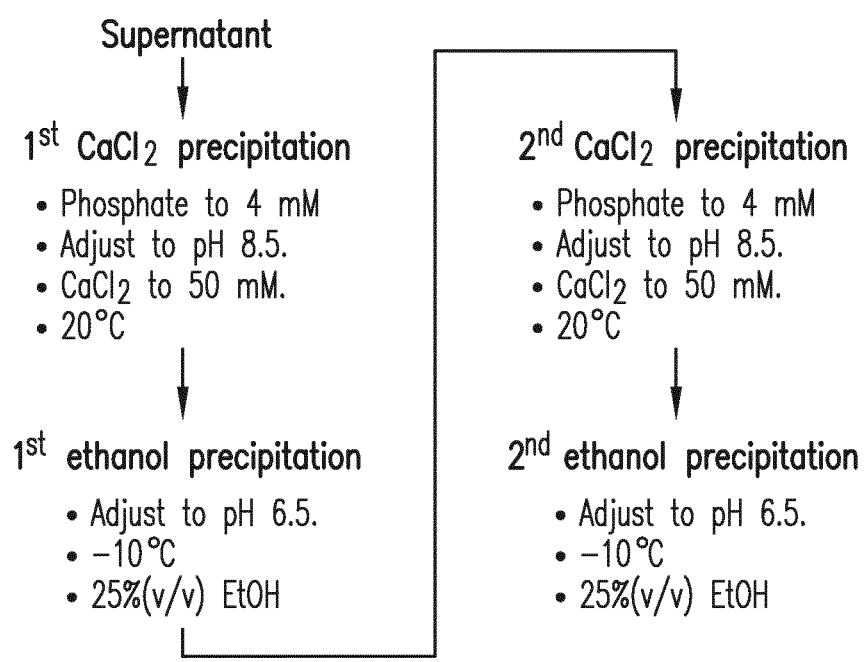
FIG. 17. Third exemplary method.

Based on these results, the optimal CaCl$_2$ precipitation step may be: 1) 4 mM phosphate (e.g., supernatant may be adjusted to this level); 2) 50 mM CaCl$_2$; and, 3) −20° C. (FIG. 17).

As shown herein, variations in the ethanol precipitation steps did not typically provide improvements in HCP content or yield although 25% ethanol and −10° C. were determined to be optimal. Washing had a beneficial effect on purity but also resulted in lower yield. Typically, then, the washing steps may not be necessary. And, while the CaCl$_2$ step may have little effect on HCP removal, it was found to be an important (e.g., critical) precursor step to the ethanol precipitation step. The use of 50 mM CaCl$_2$ was also found to be optimal (e.g., as compared to 120-150 mM CaCl$_2$ in the original method). While yield was typically comparable, lower concentrations of CaCl$_2$ typically led to greater HCP reduction.

10. Influence of Filtration Conditions on Recovery and Purity after Precipitation at −10° C.

The yields observed for the purification strategies evaluated were sometimes significantly lower than expected. Comparing the experimental set-up of the filter screening to the conditions of the real purifications, significant differences resulted from changes in stirrer speed and temperature. The filter screening was performed in the cold room at 4° C. in a 400 ml vessel with a stirrer speed of 400 rpm. The purifications were performed at ambient temperature. Only the precipitate and the washing solution were at the required temperature (e.g., −10° C.). The stirrer speed may be significantly higher (1000 rpm for a volume of 10 ml). Three parameters were selected for screening: stirrer speed, washing conditions, and the storage temperature of syringes and filters. As the lab reactor used for the precipitation method screening is at ambient temperature, all handling had to be performed at that temperature. In order to evaluate if these parameters resulted in the low recovery, a second filter screening was performed, as summarized in Table 30.

TABLE 30

| Parameters | Variation |
|---|---|
| Stirrer speed | 400 rpm |
|  | 1000 rpm |
| Washing | Wash |
|  | No Wash |
| Storage temperature of syringes and filter | Room temperature (RT) |
|  | 4° C. (fridge) |
|  | −20° C. (freeaer) |

For each experiment, 96% (v/v) ethanol was added to 5 ml of supernatant (e.g., supernatant A) to a final concentration of ~40% (v/v) ethanol. The suspensions were equilibrated for 2 h at −10° C. and collected by filtration using the depth filter. If required, the precipitate was washed by rinsing the filter with a tempered 40% (v/v) ethanol solution. The syringes and filters were stored at the respective temperature until used. The obtained samples are given in Table 31.

TABLE 31

| Run # | Stirrer speed | Washing | Storage temperature |
|---|---|---|---|
| 1 | 400 | Wash | RT |
| 2 | 400 | No Wash | RT |
| 3 | 400 | Wash | 4° C. |
| 4 | 400 | No Wash | 4° C. |
| 5 | 400 | Wash | −20° C. |
| 6 | 400 | No Wash | −20° C. |
| 7 | 1000 | Wash | RT |
| 8 | 1000 | No Wash | RT |
| 9 | 1000 | Wash | 4° C. |
| 10 | 1000 | No Wash | 4° C. |
| 11 | 1000 | Wash | −20° C. |
| 12 | 1000 | No Wash | −20° C. |

Figure 24:
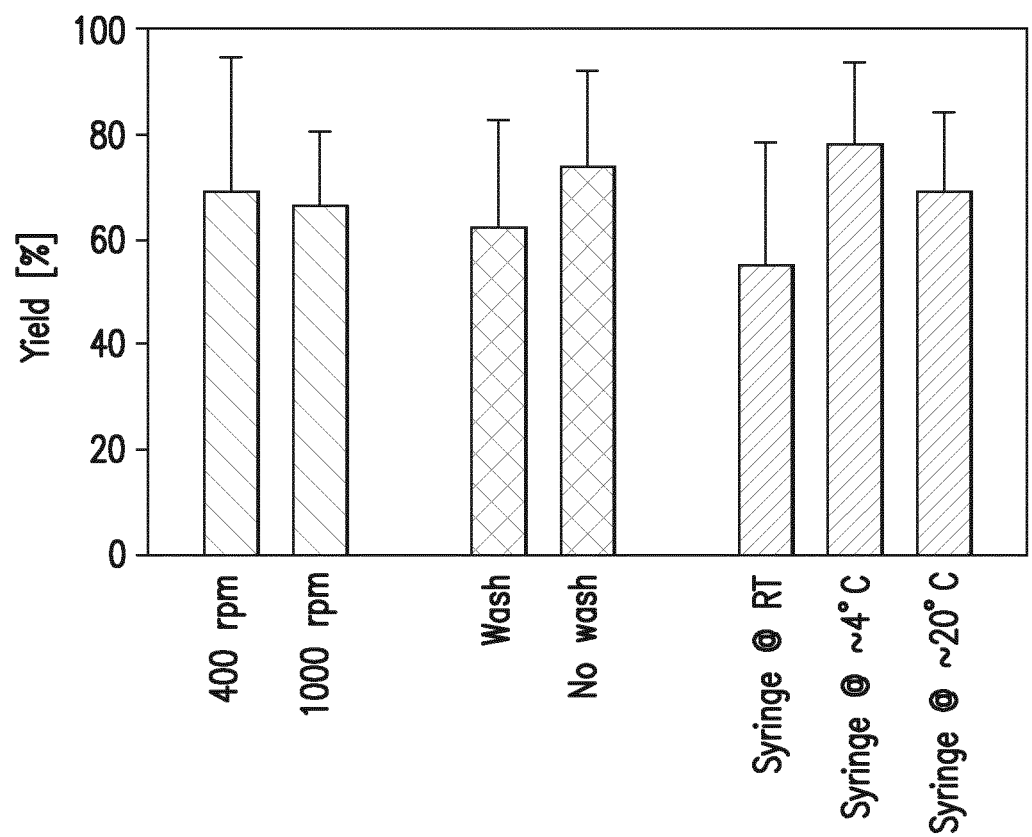

The concentration of IgG in the precipitation supernatant, the washing fraction, and the dissolved precipitate was determined by analytical protein A chromatography. The IgG present in the precipitation supernatant and the washing fraction was below the lower limit of quantification of the method used. It was therefore concluded that the yield is only negligible different from the mass balance. For a first estimation of the impact of the three main factors the average yield was calculated (FIG. 24). The stirrer speed had no significant impact on the average yield (~70%) but the standard deviation of the yield is for a stirrer speed of 400 rpm significantly higher than for 1000 rpm (likely due to differences in the particle size and density). The energy input, in our case due to the mechanical stirring, is an important parameter for the particle size and density: In general, particle size decreases and particle density increases with energy input. Also, a certain energy input is required to form homogenous particles. It was assumed that the particles obtained at a stirrer speed of 400 rpm are large, not that dense and of inhomogeneous size. Therefore, significant differences in yield can be observed. On the other hand, the particles obtained at a stirrer speed of 1000 rpm are smaller but denser and should be of a homogenous size distribution. It was determined that washing results in a loss of about 10% IgG as compared to no washing. The standard deviation is similar for either case. It was observed that storage at room temperature results in a lower yield (60%) as compared to storage at 4° C. (80%) and −20° C. (70%).

Figure 25:
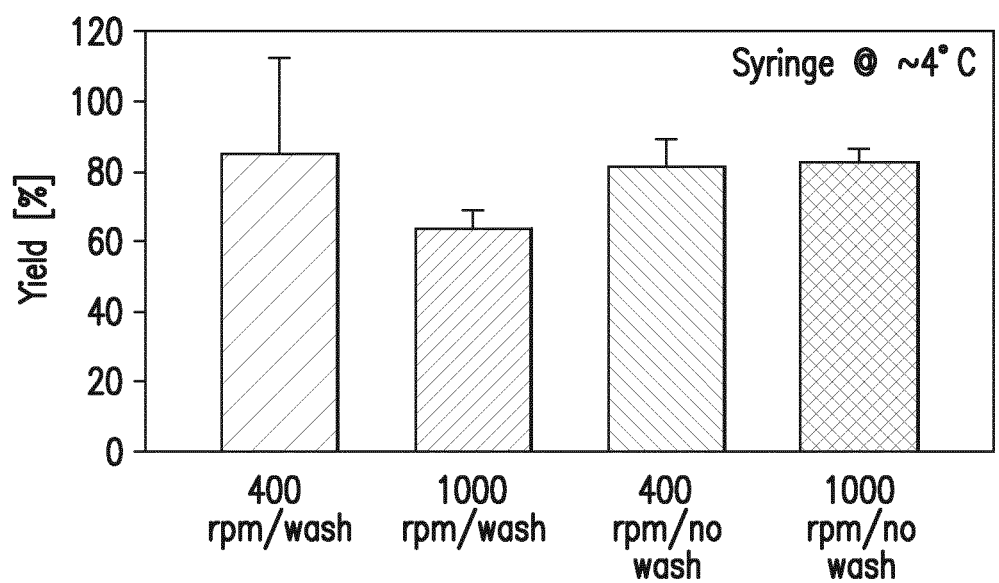
FIG. 25. Comparison of different conditions using syringe and filter maintained at 4° C.
Figure 26A:
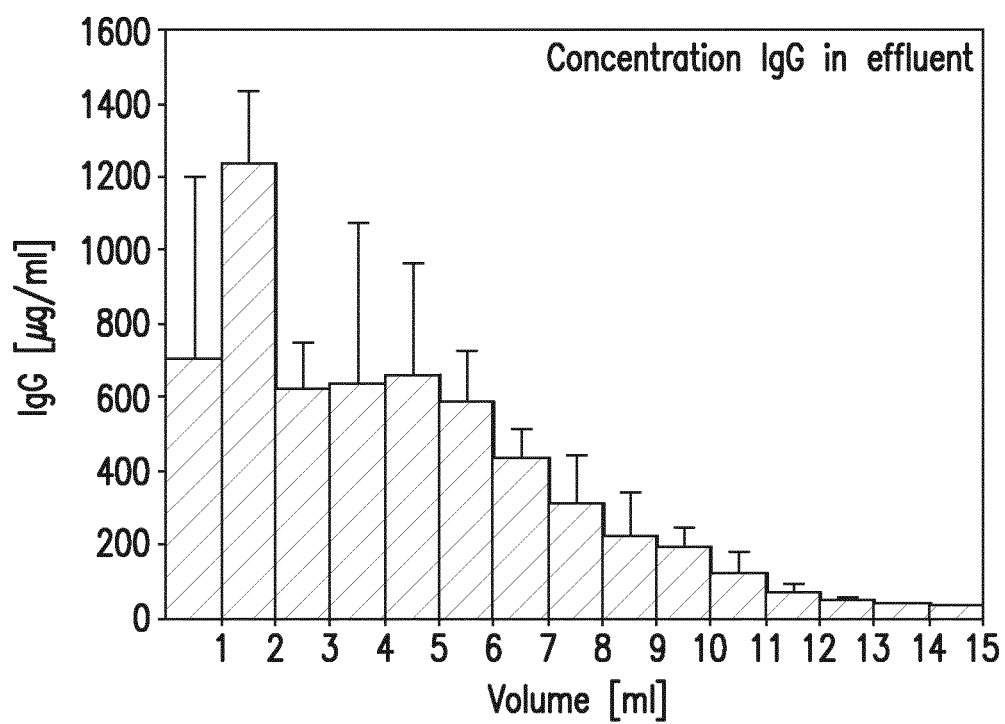
FIG. 26. Dissolution experiments following precipitation at −10° C.
Figure 26B:
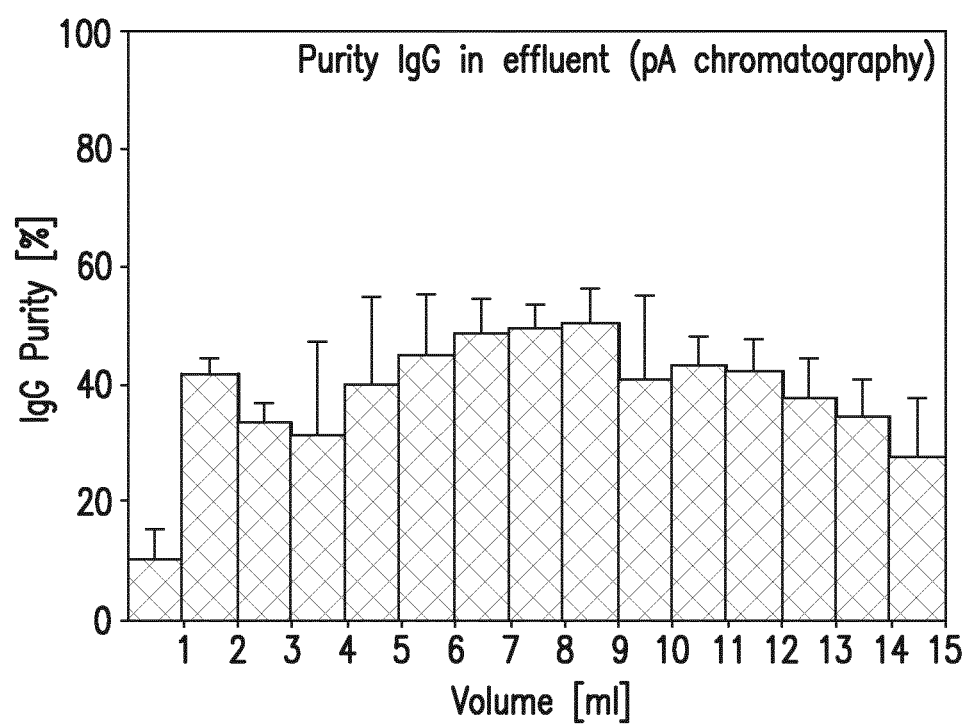
Figure 26C:
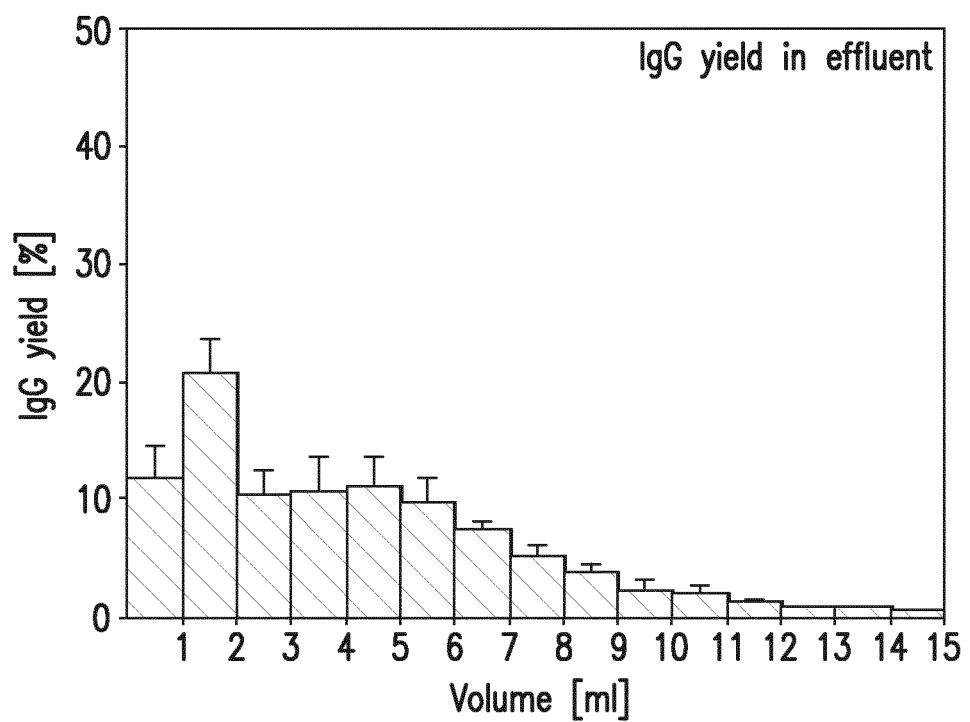
Figure 26D:
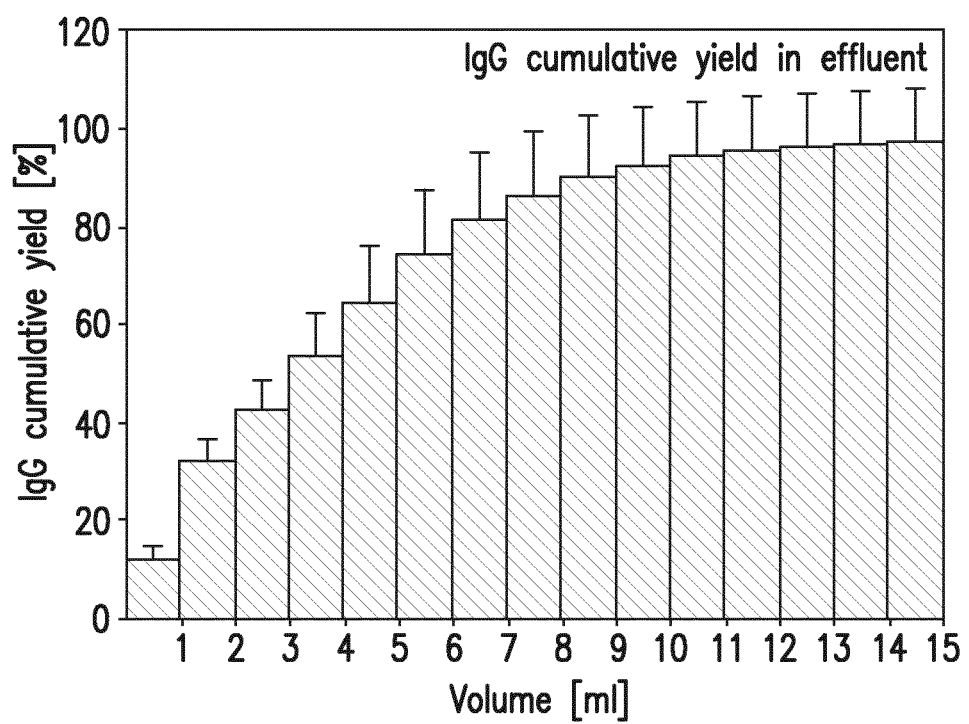

A more detailed analysis of the influence of stirrer speed and washing is provided in FIG. 25. The precipitates obtained at a stirrer speed of 400 rpm show a similar average yield when washed or when not washed. Only the standard deviation of the samples which were washed is larger than the samples which were not washed. In case of the higher stirrer speed, the standard deviation of the washed precipitates and the unwashed precipitates is similar but the average of the washed precipitates is lower. It was assumed that the smaller particles formed at 1000 rpm were more easily dissolved than the particles at 400 rpm. Therefore, washing of particles formed at 1000 rpm has more impact. In contrast the particles formed at 400 rpm are not homogenous, therefore the large standard deviation is observed in case of the washed precipitate. Depending on the sample a part of the precipitate can be easily dissolved during washing. A stirrer speed of about 600 rpm was found optimal in these experiments. Lower speed may lead to non-homogeneous particle size and varying yield. A higher stirring speed will result in small particles which can easily dissolve during washing. The syringes and filters may also be stored at 4° C., which should also significantly reduce loss of precipitate during collection. With these conditions, the evaluation of the precipitation strategies will be repeated. After up-scaling, collection may be performed by centrifugation.

11. Elution Profile of Dissolved Precipitate—Recovery and Purity

The wash-out effect of the depth filters used for recovery collection and dissolution was also studied. Monoclonal antibody A supernatant was precipitated using 40% (v/v) ethanol and dissolved with aliquots of 1 ml histidine buffer (20 mM histidine, 100 mM NaCl, pH 6.0). The effluent was collected and analyzed by analytical protein A chromatography. The purity of the effluent fractions was also determined by comparison of the area of the IgG peak and the total peak areas. This method was found sufficient for monitoring the purity trend of the effluent fraction. In FIG. 26, the concentration and purity of the effluent fraction is depicted. As shown therein, the first fraction is of low purity due to the precipitation supernatant still present in the filter. Purity increases in the second fraction and also a concentration spike is observed. In the following fractions, no trend regarding purity was observed (although it varied between 40-50%). This is not too high and may be ascribed to unspecific precipitation conditions and the rather simple method of purity determination. The concentration was stable in the first five fractions before an exponential wash-out was observed. From the calculated yield of each fraction, and the cumulative yield, a dissolution volume of approximately 10 ml was estimated to be sufficient for obtaining a suitable, though not complete, recovery of precipitated IgG. Precipitation collection by filtration is typically most useful at smaller scale (<20 ml). With up-scaling, centrifugation may be used as it allows faster and easier handling of larger volumes.

C. Conclusions

The comparison of the purification strategies for the monoclonal antibody-containing supernatants A, B and C surprisingly showed that the purification strategies presented here may be used to selectively separate IgG from protein impurities and DNA directly from cell culture supernatant with exceptional purity and yield. For example, for supernatant A, purification strategies B and C may be optimal. For supernatant B, strategies C and K may be optimal. And for supernatant C, purification strategies C, M and O may be optimal. Purification strategy C provides good results for all supernatants and may therefore be the most generally optimal strategy. In addition, in some instances, it may be optimal to perform two precipitations to obtain a satisfactory purity (HCP). Modified strategy C (e.g., FIG. 17) may also be optimal and generally applicable to the isolation of many different monoclonal antibodies (e.g., of different pIs) from different sources (e.g., supernatant of various types of cells). Decreased yield may result from the method of precipitate recovery (e.g., washing and dissolution). In particular, reducing the temperature difference between the precipitate and the syringes and filters by using tempered syringes and filters (4° C.) provides increased yield. Comparison of the different alcohols for their effect on antibody precipitation led to the conclusion that ethanol could be replaced by methanol or isopropanol with no obvious change in the precipitation behaviour of the antibody.

While the present invention has been described in terms of the preferred embodiments, it is understood that variations and modifications will occur to those skilled in the art. Therefore, it is intended that the appended claims cover all such equivalent variations that come within the scope of the invention as claimed.

The invention claimed is:

1. A method for isolating a protein from a cell culture supernatant, the method comprising:
   a) combining a cell culture supernatant with a divalent cation salt under conditions suitable for the precipitation of impurities in the supernatant to produce a primary supernatant;
   b) combining the primary supernatant with an aliphatic alcohol under conditions suitable for forming a protein-containing precipitate and isolating the protein-containing precipitate;
   c) re-suspending the protein-containing precipitate in a buffer comprising a divalent cation salt under conditions suitable for the precipitation of impurities therefrom to produce a protein-containing solution; and,
   d) combining the protein-containing solution with an aliphatic alcohol under conditions suitable for forming a purified protein-containing precipitate and isolating the purified protein-containing precipitate.

2. The method of claim 1 wherein the aliphatic alcohol is ethanol.

3. The method of claim 1 wherein the conditions of step a) comprise a phosphate concentration of less than or equal to about 6 mM.

4. The method of claim 1 wherein the conditions of step c) comprise a phosphate concentration of less than about 6 mM.

5. The method of claim 1 wherein the conditions in each of the steps comprise a pH of about 6.5 to about 8.5.

6. The method of claim 1 wherein the divalent cation salt is $CaCl_2$.

7. The method of claim 1 wherein the conditions of steps a) and c) comprise a conductivity of about 8-80 mS/cm.

8. The method of claim 1 carried out at a temperature of from about −10° C. to about 4° C.

9. The method of claim 1 wherein the conditions of steps b) and d) are selected from the group consisting of a pH of about 6.5, a final concentration (v/v) of aliphatic alcohol of about 25%, and a temperature of about −10° C.

10. The method of claim 1 wherein the protein is an antibody.

11. The method of claim 10, the method comprising:
   a) combining a cell-free culture supernatant with $CaCl_2$ at about pH 8.5 and removing any resulting precipitate to produce a primary supernatant;

b) combining the primary supernatant with ethanol from a stock solution of less than about 50% over a time period of about 60 minutes or a feeding rate of about 30 µl/min or less at about pH 6.5 and isolating the antibody-containing precipitate;

c) re-suspending the antibody-containing precipitate in a buffer comprising $CaCl_2$ at about pH 8.5 and removing any resulting precipitate to produce an antibody-containing solution; and, d) combining the antibody-containing solution with ethanol from a stock solution of less than about 50% over a time period of about 60 minutes or a feeding rate of about 30 µl/min or less at about pH 6.5 and isolating the purified antibody-containing precipitate.

12. The method of claim 1 wherein the cell culture supernatant is a cell-free culture supernatant.

13. A method for isolating a protein from a cell culture supernatant, the method comprising:
   a) combining a cell culture supernatant comprising the protein with an aliphatic alcohol under conditions suitable for forming a protein-containing precipitate and isolating the protein-containing precipitate;
   b) re-suspending the protein-containing precipitate in a buffer comprising a divalent cation salt under conditions suitable for the precipitation of impurities therefrom to produce a protein-containing solution; and,
   c) combining the protein-containing solution with an aliphatic alcohol under conditions suitable for forming a purified protein-containing precipitate and isolating the purified protein-containing precipitate.

14. The method of claim 13 wherein the protein is an antibody.

15. The method of claim 14, the method comprising:
   a) combining a primary supernatant derived from a cell-free culture supernatant with ethanol from a stock solution of less than about 50% over a time period of about 60 minutes or a feeding rate of about 30 µl/min or less at about pH 6.5 and isolating the antibody-containing precipitate;
   b) re-suspending the antibody-containing precipitate in a buffer comprising $CaCl_2$ at about pH 8.5 and removing any resulting precipitate to produce an antibody-containing solution; and,
   c) combining the antibody-containing solution with ethanol from a stock solution of less than about 50% over a time period of about 60 minutes or a feeding rate of about 30 µl/min or less at about pH 6.5 and isolating the purified antibody-containing precipitate.

16. The method of claim 13 wherein the cell culture supernatant is a cell-free culture supernatant.

17. The method of claim 13 wherein the aliphatic alcohol is ethanol.

18. The method of claim 13 wherein the divalent cation salt is $CaCl_2$.

19. The method of claim 13 wherein the conditions of step b) comprise a phosphate concentration of less than 6 mM.

20. The method of claim 13 wherein the conditions in each of the steps comprise a pH of about 6.5 to about 8.5.

* * * * *